US007811573B2

(12) United States Patent
Ensoli

(10) Patent No.: US 7,811,573 B2
(45) Date of Patent: Oct. 12, 2010

(54) COMPOSITIONS OF ANTIGENS BOUND TO HIV-1 TAT, FRAGMENTS OR DERIVATIVES THEREOF

(75) Inventor: Barbara Ensoli, Rome (IT)

(73) Assignee: Istituto Superiore di Sanita', Rome (IT)

( * ) Notice: Subject to any disclaimer, the term of this patent is extended or adjusted under 35 U.S.C. 154(b) by 551 days.

(21) Appl. No.: 10/485,180

(22) PCT Filed: Jul. 26, 2002

(86) PCT No.: PCT/EP02/08377

§ 371 (c)(1),
(2), (4) Date: Aug. 23, 2004

(87) PCT Pub. No.: WO03/009867

PCT Pub. Date: Feb. 6, 2003

(65) Prior Publication Data
US 2005/0036985 A1    Feb. 17, 2005

(30) Foreign Application Priority Data
Jul. 26, 2001    (EP)    ................... 01118114

(51) Int. Cl.
*A61K 39/38*   (2006.01)
*A61K 39/12*   (2006.01)
*A61K 39/21*   (2006.01)
*A61K 39/00*   (2006.01)
*A61K 39/385*  (2006.01)

(52) U.S. Cl. .............. 424/184.1; 424/185.1; 424/186.1; 424/187.1; 424/188.1; 424/192.1; 424/193.1; 424/194.1; 424/196.11

(58) Field of Classification Search ........................ None
See application file for complete search history.

(56) References Cited

U.S. PATENT DOCUMENTS

2005/0063978 A1 * 3/2005 Fritz et al. ............... 424/184.1

FOREIGN PATENT DOCUMENTS

| CA | 2 426 490 A1 | 4/2002 |
|---|---|---|
| WO | WO 99/27958 | 6/1999 |
| WO | WO 00/78969 A1 | 12/2000 |
| WO | WO 01/00232 A2 | 1/2001 |
| WO | WO 01/12220 A1 | 2/2001 |
| WO | WO 01/19393 A1 | 3/2001 |
| WO | WO 01/54717 A1 | 8/2001 |
| WO | WO 01/54719 A2 | 8/2001 |
| WO | WO 01/91536 A2 | 12/2001 |
| WO | WO 02/32451 A1 | 4/2002 |

OTHER PUBLICATIONS

Salfeld et al. A tripartite HIV-1 tat-env-rev fusion protein. The EMBO journal 1990, vol. 9, No. 3, pp. 965-970.*

Schiller et al. Papillomavirus-like particle based vaccines: cervical cancer and beyond. Expert Opinion on Biological Therapy Jul. 2001, vol. 1, No. 4, pp. 571-581.*

Gerotto et al. Effect of Retreatment with Interferon Alone or Interferon plus Ribavirin on Hepatitis C Virus Quasispecies Diversification in Nonresponder Patients with Chronic Hepatitis C. Journal of Virology, Sep. 1999, vol. 73, No. 9, p. 7241-7247.*

Huang et al. Recent development of therapeutics for chronic HCV infection. Antiviral Research 2006, vol. 71, p. 351-362.*

Navas-Martin et al. Coronavirus replication and pathogenesis: Implications for the recent outbreak of severe acute respiratory syndrome (SARS), and the challenge for vaccine development. Journal of Neurology 2004, vol. 10, p. 75-85.*

Tonini et al. Current approaches to developing a preventative HIV vaccine. Current Opinion in Investigational Drugs 2005, vol. 6, No. 2, pl. 155-162.*

Yin et al. Overcoming HIV drug resistance through rational drug design based on molecular, biochemical, and structural profiles of HIV resistance. Cellular and Molecular Life Sciences 2006, vol. 63, p. 1706-1724.*

Addo M.M. et al. The HIV-1 regulatory proteins Tat and Rev are frequently targeted by cytotoxic T lymphocytes derived from HIV-1-infected individuals. Proc Natl Acad Sci U S A. Feb. 13, 2001;98(4):1781-6.

Barillari G. et al. The Tat protein of human immunodeficiency virus type-1 promotes vascular cell growth and locomotion by engaging the alpha5beta1 and alphavbeta3 integrins and by mobilizing sequestered basic fibroblast growth factor. Blood. Jul. 15, 1999;94(2):663-72.

(Continued)

*Primary Examiner*—Jeffrey S Parkin
*Assistant Examiner*—Louise Humphrey
(74) *Attorney, Agent, or Firm*—Jones Day

(57) ABSTRACT

The present invention concerns a method for prophylactic and/or therapeutic vaccination and/or treatment and/or diagnosis of HIV/AIDS, other infectious diseases, inflammatory and angiogenic diseases and tumours which utilizes a biologically active HIV-1 Tat protein, fragments or derivates thereof, as a module with one or more of the following features: antigen, adjuvant and targeting-delivery system to specific antigen-presenting cells including dendritic cells, endothelial cells and macrophages. In particular, it is claimed that Tat can be used only in its biologically active form as an antigen combined with one or more other antigens, to prime or to boost protective immune responses against itself as well as other antigens and/or to selectively deliver these antigen(s) as well as active compounds to dendritic cells, endothelial cells and macrophages, due to its capability of targeting these APC and of activating their maturation and functions and of increasing Th-1 type immune responses as an adjuvant. Therefore, due to these characteristics and to the distribution of these cells in the body (during physiological and pathological disorders), biologically active Tat, fragments or derivates thereof containing the RGD region, can be used for preventive, therapeutic and/or diagnostic purposes for HIV/AIDS, other infectious diseases, inflammatory and angiogenic diseases and tumors.

37 Claims, 30 Drawing Sheets

OTHER PUBLICATIONS

Fanales-Belasio E. et al. Native HIV-1 Tat protein targets monocyte-derived dendritic cells and enhances their maturation, function, and antigen-specific T cell responses. J Immunol. Jan. 1, 2002;168(1):197-206.

Kim D.T. et al. Introduction of soluble proteins into the MHC class I pathway by conjugation to an HIV tat peptide. J Immunol. Aug. 15, 1997;159(4):1666-8.

Albini, A. et al., "Angiogenic properties of human immunodeficiency virus type 1 Tat protein", Proc. Natl. Acad. Sci. USA 92:4838-4842 (1995).

Albini, A. et al., "The angiogenesis induced by HIV-1 tat protein is mediated by the Flk-1/KDR receptor on vascular endothelial cells", Nature Med. 2:1371-1375 (1996).

Albini, A. et al., "HIV-1 Tat protein mimicry of chemokines", Proc. Natl. Acad. Sci. USA 95:13153-13158 (1998).

Albini, A. et al., "Identification of a novel domain of HIV tat involved in monocyte chemotaxis", J. Biol. Chem. 273:15895-15900 (1998).

Allen, T. et al., "Tat-specific cytotoxic T lymphocytes select for SIV escape variants during resolution of primary viraemia", Nature 407:386-390 (2000).

Badou, A. et al., "Tat protein of human immunodeficiency virus type 1 induces interleukin-10 in human peripheral blood monocytes: implication of protein kinase C-dependent pathway", J. Virol. 74:10551-10562 (2000).

Barillari, G. et al., "Effects of cytokines from activated immune cells on vascular cell growth and HIV-1 gene expression. Implications for AIDS-Kaposi's sarcoma pathogenesis", J. Immunol. 149:3727-3734 (1992).

Barillari, G. et al., "The Tat protein of human immunodeficiency virus type 1, a growth factor for AIDS Kaposi sarcoma and cytokine-activated vascular cells, induces adhesion of the same cell types by using integrin receptors recognizing the RGD amino acid sequence", Proc. Natl. Acad. Sci USA 90:7941-7945 (1993).

Barillari, G. et al., "Inflammatory cytokines synergize with the HIV-1 Tat protein to promote angiogenesis and Kaposi's sarcoma via induction of basic fibroblast growth factor and the alpha v beta 3 integrin", J. Immunol. 163:1929-1935(1999).

Benelli, R. et al., "Monocyte-derived dendritic cells and monocytes migrate to HIV-Tat RGD and basic peptides", AIDS 12:261-268 (1998).

Benjouad, A. et al., "Cytotoxic effect on lymphocytes of Tat from human immunodeficiency virus (HIV-1)", FEBS Lett. 319:119-124 (1993).

Boykins, R. et al., "Cutting edge: a short polypeptide domain of HIV-1-Tat protein mediates pathogenesis", J. Immunol. 163:15-20 (1999).

Cafaro, A. et al, "Control of SHIV-89.6P-infection of cynomolgus monkeys by HIV-1 Tat protein vaccine", Nature Med. 5:643-650 (1999).

Cafaro, A. et al., "SHIV89.6P pathogenicity in cynomolgus monkeys and control of viral replication and disease onset by human immunodeficiency virus type 1 Tat vaccine", J. Med. Primatol. 29:193-208 (2000).

Cafaro, A. et al., "Vaccination with DNA containing tat coding sequences and unmethylated CpG motifs protects cynomolgus monkeys upon infection with simian/human immunodeficiency virus (SHIV89.6P)", Vaccine 19:2862-2877 (2001).

Chang, H. C. et al., "HIV-1 Tat protein exits from cells via a leaderless secretory pathway and binds to extracellular matrix-associated heparan sulfate proteoglycans through its basic region", AIDS 11:1421-1431 (1997).

Chang H.-K. et al., "Regulation of Cellular Gene Expression and Function by the Human Immunodeficiency Virus Type 1 Tat Protein", J. Biomed. Sci. 2:189-202 (1995).

Chirmule, N. et al., "Human immunodeficiency virus Tat induces functional unresponsiveness in T cells", J. Virol. 69:492-498 (1995).

Cohen, S. et al., "Pronounced acute immunosuppression in vivo mediated by HIV Tat challenge", Proc. Natl. Acad. Sci. USA 96:10842-10847 (1999).

Derossi, D. et al., "Trojan peptides: the penetratin system for intracellular delivery", Trends Cell. Biol. 8:84-87 (1998).

Ensoli, B. et al., "Tat protein of HIV-1 stimulates growth of cells derived from Kaposi's sarcoma lesions of AIDS patients", Nature 345:84-86 (1990).

Ensoli, B. et al., "Release, uptake, and effects of extracellular human immunodeficiency virus type 1 Tat protein on cell growth and viral transactivation", J. Virol. 67:277-287 (1993).

Ensoli, B. et al., "Synergy between basic fibroblast growth factor and HIV-1 Tat protein in induction of Kaposi's sarcoma", Nature 371:674-680 (1994).

Fawell, S. et al.; "Tat-mediated delivery of heterologous proteins into cells", Proc. Natl. Acad. Sci. USA 91:664-668 (1994).

Fiorelli, V. et al., "IFN-gamma induces endothelial cells to proliferate and to invade the extracellular matrix in response to the HIV-1 Tat protein: implications for AIDS-Kaposi's sarcoma pathogenesis", J. Immunol. 162:1165-1170 (1999).

Frankel, A. and Pabo, C., "Cellular uptake of the tat protein from human immunodeficiency virus", Cell 55:1189-1193 (1988).

Frankel, A. et al., "Activity of synthetic peptides from the Tat protein of human immunodeficiency virus type 1", Proc. Natl. Acad. Sci. USA 86:7397-7401 (1989).

Froebel, K. et al., "Cytotoxic T lymphocyte activity in children infected with HIV", AIDS Res. Hum. Retroviruses 10(suppl. 2):S83-S88 (1994).

Gallo, R., "Tat as one key to HIV-induced immune pathogenesis and Tat (correction of Pat) toxoid as an important component of a vaccine", Proc. Natl. Acad. Sci. USA 96:8324-8326 (1999).

Ganju, R. et al., "Human immunodeficiency virus tat modulates the Flk-1/KDR receptor, mitogen-activated protein kinases, and components of focal adhesion in Kaposi's sarcoma cells", J. Virol. 72:6131-6137 (1998).

Goldstein, G. et al., "Minimization of chronic plasma viremia in rhesus macaques immunized with synthetic HIV-1 Tat peptides and infected with a chimeric simian/human immunodeficiency virus (SHIV33)", Vaccine 18:2789-2795 (2000).

Gutheil, W. et al., "Human immunodeficiency virus 1 Tat binds to dipeptidyl aminopeptidase IV (CD26): a possible mechanism for Tat's immunosuppressive activity", Proc. Natl. Acad. Sci. USA 91:6594-6598 (1994).

Huang. L. et al., "Tat protein induces human immunodeficiency virus type 1 (HIV-1) coreceptors and promotes infection with both macrophage-tropic and T-lymphotropic HIV-1 strains", J. Virol. 72:8952-8960 (1998).

Ito, M. et al., "HIV type 1 Tat protein inhibits interleukin 12 production by human peripheral blood mononuclear cells", AIDS Res. Hum. Retroviruses 14:845-849 (1998).

Kolson, D. et al., "HIV-1 Tat alters normal organization of neurons and astrocytes in primary rodent brain cell cultures: RGD sequence dependence", AIDS Res. Hum. Retroviruses 9:677-685 (1993).

Lafrenie, R. et al., "HIV-1-Tat protein promotes chemotaxis and invasive behavior by monocytes", J. Immunol. 157:974-977 (1996).

Li, C. et al., "Induction of apoptosis in uninfected lymphocytes by HIV-1 Tat protein", Science 268:429-431 (1995).

Li, C. et al., "Tat protein induces self-perpetuating permissivity for productive HIV-1 infection", Proc. Natl. Acad. Sci. USA 94:8116-8120 (1997).

Mann, D. and Frankel, A., "Endocytosis and targeting of exogenous HIV-1 Tat protein", EMBO J. 10:1733-1739 (1991).

Masood, R. et al., "IL-10 inhibits HIV-1 replication and is induced by tat", Biochem. Biophys. Res. Comm. 202:374-383(1994).

McCloskey, T. et al., "Dual role of HIV Tat in regulation of apoptosis in T cells", J. Immunol. 158:1014-1019 (1997).

Mei, H. et al., "Discovery of selective, small-molecule inhibitors of RNA complexes. I. The tat protein/TAR RNA complexes required for HIV-1 transcription", Bioorg. Med. Chem. 5:1173-1184.

Milani, D. et al., "Extracellular human immunodeficiency virus type-1 Tat protein activates phosphatidylinositol 3-kinase in PC12 neuronal cells", J. Biol. Chem. 271:22961-22964 (1996).

Mitola, S. et al., "Tat-human immunodeficiency virus-1 induces human monocyte chemotaxis by activation of vascular endothelial growth factor receptor-1", Blood 90:1365-1372 (1997).

Mitola, S. et al., "Identification of specific molecular structures of human immunodeficiency virus type 1 Tat relevant for its biological effects on vascular endothelial cells", J. Virol. 74:344-353 (2000).

Morini, M. et al., "Kaposi's sarcoma cells of different etiologic origins respond to HIV-Tat through the Flk-1/KDR (VEGFR-2): relevance in AIDS-KS pathology", Biochem. Biophys. Res. Comm. 273:267-271 (2000).
Moy, P. et al., "Tat-mediated protein delivery can facilitate MHC class I presentation of antigens", Mol. Biotechnol. 6:105-113 (1996).
Osterhaus, A. et al., "Vaccination with Rev and Tat against AIDS", Vaccine 17:2713-2714 (1999).
Ott, M. et al., "Immune hyperactivation of HIV-1-infected T cells mediated by Tat and the CD28 pathway", Science 275:1481-1485 (1997).
Pauza, C. et al., "Vaccination with tat toxoid attenuates disease in simian/HIV-challenged macaques", Proc. Natl. Acad. Sci. USA 97:3515-3519 (2000).
Pittis, M. et al., "Recombinant human immunodeficiency virus type 1 (HIV-1) Tat protein inhibits phagolysosomal fusion in human peripheral blood monocytes", Viral Immunol. 9:169-174 (1996).
Purvis, S. et al., "HIV type 1 Tat protein induces apoptosis and death in Jurkat cells", AIDS Res. Hum. Retroviruses 11:443-450 (1995).
Raines and Ross, "Compartmentalization of PDGF on extracellular binding sites dependent on exon-6-encoded sequences". J. Cell Biol. 116:533-543 (1992).
Re, M. et al., "Effect of antibody to HIV-1 Tat protein on viral replication in vitro and progression of HIV-1 disease in vivo", J. Acquir. Immune Defic. Syndr. Hum. Retrovirol. 10:408-416 (1995).
Reiss, P. et al., "Speed of progression to AIDS and degree of antibody response to accessory gene products of HIV-1". J. Med. Virol. 30:163-168 (1990).
Rodman, T. et al., "Epitopes for natural antibodies of human immunodeficiency virus (HIV)-negative (normal) and HIV-positive sera are coincident with two key functional sequences of HIV Tat protein", Proc. Natl. Acad. Sci. USA 90:7719-7723 (1993).
Rubartelli, A. et al., "The selective engulfment of apoptotic bodies by dendritic cells is mediated by the alpha(v)beta3 integrin and requires intracellular and extracellular calcium", Eur. J. Immunol. 27:1893-1900 (1997).
Rusnati, M. et al., "The basic domain in HIV-1 Tat protein as a target for polysulfonated heparin-mimicking extracellular Tat antagonists", J. Biol. Chem. 273:16027-16030 (1998).
Sabatier J. et al., "Evidence for neurotoxic activity of tat from human immunodeficiency virus type 1", J. Virol. 65:961-967 (1991).
Samaniego, F. et al., "Vascular endothelial growth factor and basic fibroblast growth factor present in Kaposi's sarcoma (KS) are induced by inflammatory cytokines and synergize to promote vascular permeability and KS lesion development", Am. J. Pathol. 152:1433-1443 (1998).
Secchiero, P. et al, "Extracellular HIV-1 tat protein up-regulates the expression of surface CXC-chemokine receptor 4 in resting CD4+ T cells", J. Immunol. 162:2427-2431 (1999).
Subramanyam, M. et al., "Mechanism of HIV-1 Tat induced inhibition of antigen-specific T cell responsiveness". J. Immunol. 150:2544-2553 (1993).
Tyagi, M. et al., "Internalization of HIV-1 tat requires cell surface heparan sulfate proteoglycans", J. Biol. Chem. 276:3254-3261 (2001) (Epub Oct. 6, 2000).
Van Baalen, C. et al., "Human immunodeficiency virus type 1 Rev- and Tat-specific cytotoxic T lymphocyte frequencies inversely correlate with rapid progression to AIDS", J. Gen. Virol. 78:1913-1918 (1997).
Venet, A. et al., "Cytotoxic T lymphocyte response against multiple simian immunodeficiency virusA (SIV) proteins in SIV-infected macaques", J. Immunol. 148:2899-2908 (1992).
Viscidi, R. et al., "Inhibition of antigen-induced lymphocyte proliferation by Tat protein from HIV-1", Science 246:1606-1608 (1989).
Vogel, B. et al., "A novel integrin specificity exemplified by binding of the alpha v beta 5 integrin to the basic domain of the HIV Tat protein and vitronectin", J. Cell Biol.121:461-468 (1993).
Weeks, B. et al., "Identification of a novel cell attachment domain in the HIV-I Tat protein and its 90-kDa cell surface binding protein", J. Biol. Chem. 268:5279-5284 (1993).
Wender, P. et al., "The design, synthesis, and evaluation of molecules that enable or enhance cellular uptake: peptoid molecular transporters", Proc. Natl. Acad. Sci. USA 97:13003-13008 (2000).
Westendorp, M. et al., "Sensitization of T cells to CD95-mediated apoptosis by HIV-1 Tat and gp120", Nature 375:497-500 (1995).
Wrenger, S. et al., "The N-terminal X-X-Pro sequence of the HIV-1 Tat protein is important for the inhibition of dipeptidyl peptidase IV (DP IV/CD26) and the suppression of mitogen-induced proliferation of human T cells", FEBS Lett. 383:145-149 (1996).
Wrenger, S. et al., "The N-terminal structure of HIV-1 Tat is required for suppression of CD26-dependent T cell growth", J. Biol. Chem. 272:30283-30288 (1997).
Wu M. and Schlossman, F. "Decreased ability of HIV-1 tat protein-treated accessory cells to organize cellular clusters is associated with partial activation of T cells". Proc. Natl. Acad. Sci. USA 94:13832-13837 (1997).
Zagury D. et al., "Interferon alpha and Tat involvement in the immunosuppression of uninfected T cells and C-C chemokine decline in AIDS", Proc. Natl. Acad. Sci. USA 95:3851-3856 (1998).
Zagury J. et al., "Antibodies to the HIV-1 Tat protein correlated with nonprogression to AIDS: a rationale for the use of Tat toxoid as an HIV-1 vaccine", J. Hum. Virol. 1:282-292 (1998).
Zauli, G. et al., "Human immunodeficiency virus type 1 Tat protein protects lymphoid, epithelial, and neuronal cell lines from death by apoptosis", Cancer Res. 53:4481-4485 (1993).
Zauli, G. et al., "An autocrine loop of HIV type-1 Tat protein responsible for the improved survival/proliferation capacity of permanently Tat-transfected cells and required for optimal HIV-1 LTR transactivating activity", J. Acquir. Immune Defic. Syndr. Hum. Retrovirol. 10:306-316 (1995).
Zauli, G. et al., "The human immunodeficiency virus type-1 Tat protein upregulates Bcl-2 gene expression in Jurkat T-cell lines and primary peripheral blood mononuclear cells", Blood 86:3823-3834 (1995).
Zocchi, M. et al., "The RGD-containing domain of exogenous HIV-1 Tat inhibits the engulfment of apoptotic bodies by dendritic cells", AIDS 11:1227-1235 (1997).
Albini, A. et al., "Angiogenic properties of human immunodeficiency virus type 1 Tat protein", Proc. Natl. Acad. Sci. USA 92:4838-4842 (1995).
Albini, A. et al., "The angiogenesis induced by HIV-1 tat protein is mediated by the Flk-1/KDR receptor on vascular endothelial cells", Nature Med. 2:1371-1375 (1996).
Albini, A. et al., "HIV-1 Tat protein mimicry of chemokines", Proc. Natl. Acad. Sci. USA 95:13153-13158 (1998).
Albini, A. et al., "Identification of a novel domain of HIV tat involved in monocyte chemotaxis", J. Biol. Chem. 273:15895-15900 (1998).
Allen, T. et al., "Tat-specific cytotoxic T lymphocytes select for SIV escape variants during resolution of primary viraemia", Nature 407:386-390 (2000).
Badou, A. et al., "Tat protein of human immunodeficiency virus type 1 induces interleukin-10 in human peripheral blood monocytes: implication of protein kinase C-dependent pathway", J. Virol. 74:10551-10562 (2000).
Barillari, G. et al., "Effects of cytokines from activated immune cells on vascular cell growth and HIV-1 gene expression. Implications for AIDS-Kaposi's sarcoma pathogenesis", J. Immunol. 149:3727-3734 (1992).
Barillari, G. et al., "The Tat protein of human immunodeficiency virus type 1, a growth factor for AIDS Kaposi sarcoma and cytokine-activated vascular cells, induces adhesion of the same cell types by using integrin receptors recognizing the RGD amino acid sequence", Proc. Natl. Acad. Sci USA 90:7941-7945 (1993).
Barillari, G. et al., "Inflammatory cytokines synergize with the HIV-1 Tat protein to promote angiogenesis and Kaposi's sarcoma via induction of basic fibroblast growth factor and the alpha v beta 3 integrin", J. Immunol. 163:1929-1935 (1999).
Benelli, R. et al., "Monocyte-derived dendritic cells and monocytes migrate to HIV-Tat RGD and basic peptides", AIDS 12:261-268 (1998).
Benjouad, A. et al., "Cytotoxic effect on lymphocytes of Tat from human immunodeficiency virus (HIV-1)", FEBS Lett. 319:119-124 (1993).
Boykins, R. et al., "Cutting edge: a short polypeptide domain of HIV-1-Tat protein mediates pathogenesis", J. Immunol. 163:15-20 (1999).

Cafaro, A. et al., "Control of SHIV-89.6P-infection of cynomolgus monkeys by HIV-1 Tat protein vaccine", Nature Med. 5:643-650 (1999).

Cafaro, A. et al., "SHIV89.6P pathogenicity in cynomolgus monkeys and control of viral replication and disease onset by human immunodeficiency virus type 1 Tat vaccine", J. Med. Primatol. 29:193-208 (2000).

Cafaro, A. et al., "Vaccination with DNA containing tat coding sequences and unmethylated CpG motifs protects cynomolgus monkeys upon infection with simian/human immunodeficiency virus (SHIV89.6P)", Vaccine 12:2862-2877 (2001).

Chang, H. C. et al., "HIV-1 Tat protein exits from cells via a leaderless secretory pathway and binds to extracellular matrix-associated heparan sulfate proteoglycans through its basic region", AIDS 11:1421-1431 (1997).

Chang H.-K. et al., "Regulation of Cellular Gene Expression and Function by the Human Immunodeficiency Virus Type 1 Tat Protein", J. Biomed. Sci. 2:189-202 (1995).

Chirmule, N. et al., "Human immunodeficiency virus Tat induces functional unresponsiveness in T cells", J. Virol. 69:492-498 (1995).

Cohen, S. et al., "Pronounced acute immunosuppression in vivo mediated by HIV Tat challenge", Proc. Natl. Acad. Sci. USA 96:10842-10847 (1999).

Derossi, D. et al., "Trojan peptides: the penetratin system for intracellular delivery", Trends Cell. Biol. 8:84-87 (1998).

Ensoli, B. et al., "Tat protein of HIV-1 stimulates growth of cells derived from Kaposi's sarcoma lesions of AIDS patients", Nature 345:84-86 (1990).

Ensoli, B. et al., "Release, uptake, and effects of extracellular human immunodeficiency virus type 1 Tat protein on cell growth and viral transactivation", J. Virol. 67:277-287 (1993).

Ensoli, B. et al., "Synergy between basic fibroblast growth factor and HIV-1 Tat protein in induction of Kaposi's sarcoma", Nature 371:674-680 (1994).

Fawell, S. et al., "Tat-mediated delivery of heterologous proteins into cells", Proc. Natl. Acad. Sci. USA 91:664-668 (1994).

Fiorelli, V. et al., "IFN-gamma induces endothelial cells to proliferate and to invade the extracellular matrix in response to the HIV-1 Tat protein: implications for AIDS-Kaposi's sarcoma pathogenesis", J. Immunol. 162:1165-1170 (1999).

Frankel, A. and Pabo, C., "Cellular uptake of the tat protein from human immunodeficiency virus", Cell 55:1189-1193 (1988).

Frankel, A. et al., "Activity of synthetic peptides from the Tat protein of human immunodeficiency virus type 1", Proc. Natl. Acad. Sci. USA 86:7397-7401 (1989).

Froebel, K. et al., "Cytotoxic T lymphocyte activity in children infected with HIV", AIDS Res. Hum. Retroviruses 10(suppl. 2):S83-S88 (1994).

Gallo, R., "Tat as one key to HIV-induced immune pathogenesis and Tat (correction of Pat) toxoid as an important component of a vaccine", Proc. Natl. Acad. Sci. USA 96:8324-8326 (1999).

Ganju, R. et al., "Human immunodeficiency virus tat modulates the Flk-1/KDR receptor, mitogen-activated protein kinases, and components of focal adhesion in Kaposi's sarcoma cells", J. Virol. 72:6131-6137 (1998).

Goldstein, G. et al., "Minimization of chronic plasma vireinia in rhesus macaques immunized with synthetic HIV-1 Tat peptides and infected with a chimeric simian/human immunodeficiency virus (SHIV33)", Vaccine 18:2789-2795 (2000).

Gutheil, W. et al., "Human immunodeficiency virus 1 Tat binds to dipeptidyl aminopeptidase IV (CD26): a possible mechanism for Tat's immunosuppressive activity", Proc. Natl. Acad. Sci. USA 91:6594-6598 (1994).

Huang. L. et al., "Tat protein induces human immunodeficiency virus type 1 (HIV-1) coreceptors and promotes infection with both macrophage-tropic and T-lymphotropic HIV-1 strains", J. Virol. 72:8952-8960 (1998).

Ito, M. et al., "HIV type 1 Tat protein inhibits interleukin 12 production by human peripheral blood mononuclear cells", AIDS Res. Hum. Retroviruses 14:845-849 (1998).

Kolson, D. et al., "HIV-1 Tat alters normal organization of neurons and astrocytes in primary rodent brain cell cultures: RGD sequence dependence", AIDS Res. Hum. Retroviruses 9:677-685 (1993).

Lafrenie, R. et al., "HIV-1-Tat protein promotes chemotaxis and invasive behavior by monocytes", J. Immunol. 157:974-977 (1996).

Li, C. et al., "Induction of apoptosis in uninfected lymphocytes by HIV-1 Tat protein", Science 268:429-431 (1995).

Li, C. et al., "Tat protein induces self-perpetuating permissivity for productive HIV-1 infection", Proc. Natl. Acad. Sci. USA 94:8116-8120 (1997).

Mann, D. and Frankel, A., "Endocytosis and targeting of exogenous HIV-1 Tat protein", EMBO J. 10:1733-1739 (1991).

Masood, R. et al., "IL-10 inhibits HIV-1 replication and is induced by tat", Biochem. Biophys. Res. Comm. 202:374-383 (1994).

McCloskey, T. et al., "Dual role of HIV Tat in regulation of apoptosis in T cells", J. Immunol. 158:1014-1019 (1997).

Mei, H. et al., "Discovery of selective, small-molecule inhibitors of RNA complexes. I. The tat protein/TAR RNA complexes required for HIV-1 transcription", Bioorg. Med. Chem. 5:1173-1184.

Milani, D. et al., "Extracellular human immunodeficiency virus type-1 Tat protein activates phosphatidylinositol 3-kinase in PC12 neuronal cells", J. Biol. Chem. 271:22961-22964 (1996).

Mitola, S. et al., "Tat-human immunodeficiency virus-1 induces human monocyte chemotaxis by activation of vascular endothelial growth factor receptor-1", Blood 90:1365-1372 (1997).

Mitola, S. et al., "Identification of specific molecular structures of human immunodeficiency virus type 1 Tat relevant for its biological effects on vascular endothelial cells", J. Virol. 74:344-353 (2000).

Morini, M. et al., "Kaposi's sarcoma cells of different etiologic origins respond to HIV-Tat through the Flk-1/KDR (VEGFR-2): relevance in AIDS-KS pathology", Biochem. Biophys. Res. Comm. 273:267-271 (2000).

Moy, P. et al., "Tat-mediated protein delivery can facilitate MHC class I presentation of antigens", Mol. Biotechnol. 6:105-113 (1996).

Osterhaus, A. et al., "Vaccination with Rev and Tat against AIDS", Vaccine 17:2713-2714 (1999).

Ott, M. et al., "Immune hyperactivation of HIV-1-infected T cells mediated by Tat and the CD28 pathway", Science 275:1481-1485 (1997).

Pauza, C. et al., "Vaccination with tat toxoid attenuates disease in simian/HIV-challenged macaques", Proc. Natl. Acad. Sci. USA 97:3515-3519 (2000).

Pittis, M. et al., "Recombinant human immunodeficiency virus type 1 (HIV-1) Tat protein inhibits phagolysosomal fusion in human peripheral blood monocytes", Viral Immunol. 9:169-174 (1996).

Purvis, S. et al., "HIV type 1 Tat protein induces apoptosis and death in Jurkat cells", AIDS Res. Hum. Retroviruses 11:443-450 (1995).

Raines and Ross, "Compartmentalization of PDGF on extracellular binding sites dependent on exon-6-encoded sequences", J. Cell Biol. 116:533-543 (1992).

Re, M. et al., "Effect of antibody to HIV-1 Tat protein on viral replication in vitro and progression of HIV-1 disease in vivo", J. Acquir. Immune Defic. Syndr. Hum. Retrovirol. 10:408-416 (1995).

Reiss, P. et al., "Speed of progression to AIDS and degree of antibody response to accessory gene products of HIV-1", J. Med. Virol. 30:163-168 (1990).

Rodman, T. et al., "Epitopes for natural antibodies of human immunodeficiency virus (HIV)-negative (normal) and HIV-positive sera are coincident with two key functional sequences of HIV Tat protein", Proc. Natl. Acad. Sci. USA 90:7719-7723 (1993).

Rubartelli, A. et al., "The selective engulfment of apoptotic bodies by dendritic cells is mediated by the alpha(v)beta3 integrin and requires intracellular and extracellular calcium", Eur. J. Immunol. 27:1893-1900 (1997).

Rusnati, M. et al., "The basic domain in HIV-1 Tat protein as a target for polysulfonated heparin-mimicking extracellular Tat antagonists", J. Biol. Chem. 273:16027-16030 (1998).

Sabatier J. et al., "Evidence for neurotoxic activity of tat from human immunodeficiency virus type 1", J. Virol. 65:961-967 (1991).

Samaniego, F. et al., "Vascular endothelial growth factor and basic fibroblast growth factor present in Kaposi's sarcoma (KS) are induced by inflammatory cytokines and synergize to promote vascular permeability and KS lesion development", Am. J. Pathol. 152:1433-1443 (1998).

Secchiero, P. et al., "Extracellular HIV-1 tat protein up-regulates the expression of surface CXC-chemokine receptor 4 in resting CD4+ T cells", J. Immunol. 162:2427-2431 (1999).

Subramanyam, M. et al., "Mechanism of HIV-1 Tat induced inhibition of antigen-specific T cell responsiveness", J. Immunol. 150:2544-2553 (1993).

Tyagi, M. et al., "Internalization of HIV-1 tat requires cell surface heparan sulfate proteoglycans", J. Biol. Chem. 276:3254-3261 (2001) (Epub Oct. 6, 2000).

Van Baalen, C. et al., "Human immunodeficiency virus type 1 Rev- and Tat-specific cytotoxic T lymphocyte frequencies inversely correlate with rapid progression to AIDS", J. Gen. Virol. 78:1913-1918 (1997).

Venet, A. et al., "Cytotoxic T lymphocyte response against multiple simian immunodeficiency virusA (SIV) proteins in SIV-infected macaques", J. Immunol. 148:2899-2908 (1992).

Viscidi, R. et al., "Inhibition of antigen-induced lymphocyte proliferation by Tat protein from HIV-1", Science 246:1606-1608 (1989).

Vogel, B. et al., "A novel integrin specificity exemplified by binding of the alpha v beta 5 integrin to the basic domain of the HIV Tat protein and vitronectin", J. Cell Biol.121:461-468 (1993).

Weeks, B. et al., "Identification of a novel cell attachment domain in the HIV-1 Tat protein and its 90-kDa cell surface binding protein", J. Biol. Chem. 268,:5279-5284 (1993).

Wender, P. et al., "The design, synthesis, and evaluation of molecules that enable or enhance cellular uptake: peptoid molecular transporters", Proc. Natl. Acad. Sci. USA 97:13003-13008 (2000).

Westendorp, M. et al., "Sensitization of T cells to CD95-mediated apoptosis by HIV-1 Tat and gp120", Nature 375:497-500 (1995).

Wrenger, S. et al., "The N-terminal X-X-Pro sequence of the HIV-1 Tat protein is important for the inhibition of dipeptidyl peptidase IV (DP IV/CD26) and the suppression of mitogen-induced proliferation of human T cells", FEBS Lett. 383:145-149 (1996).

Wrenger, S. et al., "The N-terminal structure of HIV-1 Tat is required for suppression of CD26-dependent T cell growth", J. Biol. Chem. 272:30283-30288 (1997).

Wu M. and Schlossman, F. "Decreased ability of HIV-1 tat protein-treated accessory cells to organize cellular clusters is associated with partial activation of T cells", Proc. Natl. Acad. Sci. USA 94:13832-13837 (1997).

Zagury D. et al., "Interferon alpha and Tat involvement in the immunosuppression of uninfected T cells and C-C chemokine decline in AIDS", Proc. Natl. Acad. Sci. USA 95:3851-3856 (1998).

Zagury J. et al., "Antibodies to the HIV-1 Tat protein correlated with nonprogression to AIDS: a rationale for the use of Tat toxoid as an HIV-1 vaccine", J. Hum. Virol. 1:282-292 (1998).

Zauli, G. et al., "Human immunodeficiency virus type 1 Tat protein protects lymphoid, epithelial, and neuronal cell lines from death by apoptosis", Cancer Res. 53:4481-4485 (1993).

Zauli, G. et al., "An autocrine loop of HIV type-1 Tat protein responsible for the improved survival/proliferation capacity of permanently Tat-transfected cells and required for optimal HIV-1 LTR transactivating activity", J. Acquir. Immune Defic. Syndr. Hum. Retrovirol. 10:306-316 (1995).

Zauli, G. et al., "The human immunodeficiency virus type-1 Tat protein upregulates Bcl-2 gene expression in Jurkat T-cell lines and primary peripheral blood mononuclear cells", Blood 86:3823-3834 (1995).

Zocchi, M. et al., "The RGD-containing domain of exogenous HIV-1 Tat inhibits the engulfment of apoptotic bodies by dendritic cells", AIDS 11:1227-1235 (1997).

Vainionpää et al., "Biology of parainfluenza viruses," Clin Microbial Rev. Apr. 1994;7(2):265-75.

Tindle et al., "A vaccine conjugate of 'ISCAR' immunocarrier and peptide epitopes of the E7 cervical cancer-associated protein of human papillomavirus type 16 elicits specific Th1- and Th2-type responses in immunized mice in the absence of oil-based adjuvants," Clin Exp Immunol. Aug. 1995;101(2):265-71.

Hall et al., "Protective immune responses to the E and NS1 proteins of Murray Valley encephalitis virus in hybrids of flavivirus-resistant mice,"J Gen Virol. Jun. 1996;77 ( Pt 6):1287-94.

Hilleman et al., "Overview of vaccinology with special reference to papillomavirus vaccines," J Clin Virol. Oct. 2000;19(1-2):79-90.

Treanor et al. "Safety and immunogenicity of a recombinant hemagglutinin vaccine for H5 influenza in humans," Vaccine. Feb. 8, 2001;19(13-14):1732-7.

Goetsch et al., "BBG2Na an RSV subunit vaccine candidate intramuscularly injected to human confers protection against viral challenge after nasal immunization in mice," Vaccine. Jul. 16, 2001; 19(28-29):4036-42.

An et al., "A recombinant minigene vaccine containing a nonameric cytotoxic-T-lymphocyte epitope confers limited protection against Listeria monocytogenes infection," Infect Immun. May 1996;64(5):1685-93.

Weinrich Olsen et al., "Protection of mice with a tuberculosis subunit vaccine based on a fusion protein of antigen 85b and esat-6," Infect Immun. May 2001;69(5):2773-8.

Shen et al., "Systemic and mucosal immune responses in mice after mucosal immunization with group B streptococcus type III capsular polysaccharide-cholera toxin B subunit conjugate vaccine," Infect Immun. Oct. 2000;68(10):5749-55.

Han et al., "Prevalence of capsular polysaccharide (CP) types of Staphylococcus aureus isolated from bovine mastitic milk and protection of S. aureus infection in mice with CP vaccine," J Vet Med Sci. Dec. 2000;62(12):1331-3.

Vidarsson et al., "Isotypes and opsonophagocytosis of pneumococcus type 6B antibodies elicited in infants and adults by an experimental pneumococcus type 6B-tetanus toxoid vaccine," Infect Immun. Jun. 1998;66(6):2866-70.

Singh et al., "Immunogenicity and protection in small-animal models with controlled-release tetanus toxoid microparticles as a single-dose vaccine," Infect Immun. May 1997;65(5):1716-21.

Vodopija et al., "Reactivity and immunogenicity of bivalent (AC) and tetravalent ($ACW_{135}Y$) meningococcal vaccines containing O-acetyl-negative or O-acetyl-positive group C polysaccharide," Infect Immun. Nov. 1983;42(2):599-604.

Keenan et al., "Immune response to an 18-kilodalton outer membrane antigen identifies lipoprotein 20 as a Helicobacter pylori vaccine candidate," Infect Immun. Jun. 2000;68(6):3337-43.

Singh et al., "Antigenic determinants of the OmpC porin from Salmonella typhimurium," Infect Immun. Dec. 1995;63(12):4600-5.

Spangler, "Structure and function of cholera toxin and the related Escherichia coil heat-labile enterotoxin," Microbiol Rev. Dec. 1992;56(4):622-47, p. 638, col. 2, ¶¶3-4.

Han et al., "Biochemical characterization of Candida albicans epitopes that can elicit protective and nonprotective antibodies," Infect Immun. Oct. 1997;65(10):4100-7.

Sim et al., "Induction of biologically active antibodies in mice, rabbits, and monkeys by Plasmodium falciparum EBA-175 region II DNA vaccine," Mol Med. Apr. 2001;7(4):247-54.

Giannouli et al., "Fusion of a tumour-associated antigen to HIV-1 Tat improves protein-based immunotherapy of cancer," Anticancer Res. Jul.-Aug. 2003;23(4):3523-31.

Robert H. Abeles, Perry A. Frey & William P. Jencks, Biochemistry, p. 42 (Jones and Bartlett Publishers, Inc. 1992.

* cited by examiner

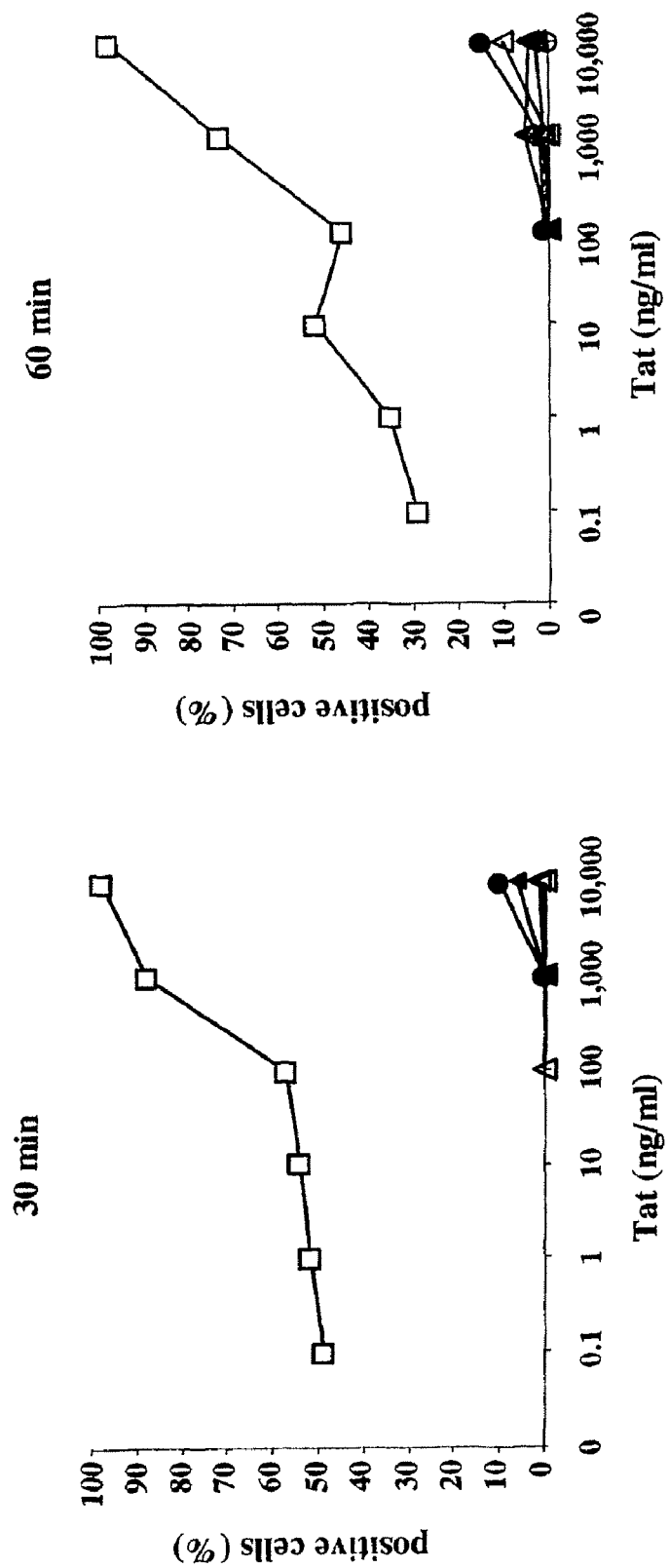

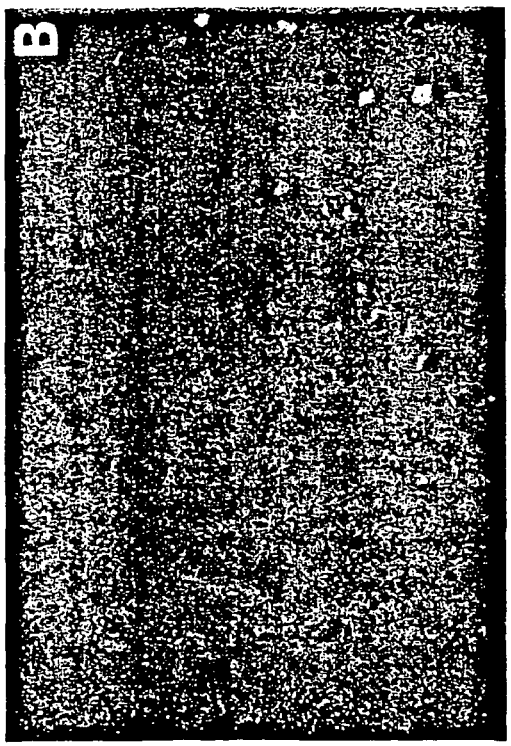
FIG. 8A
FIG. 8B
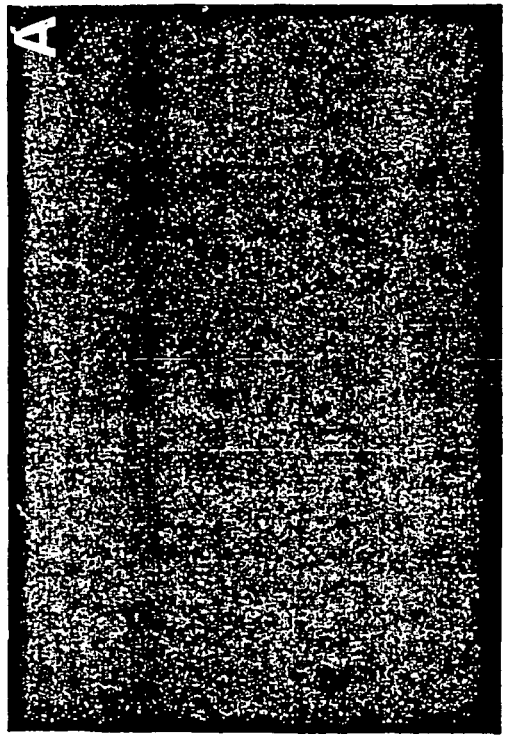
FIG. 8C
FIG. 8D

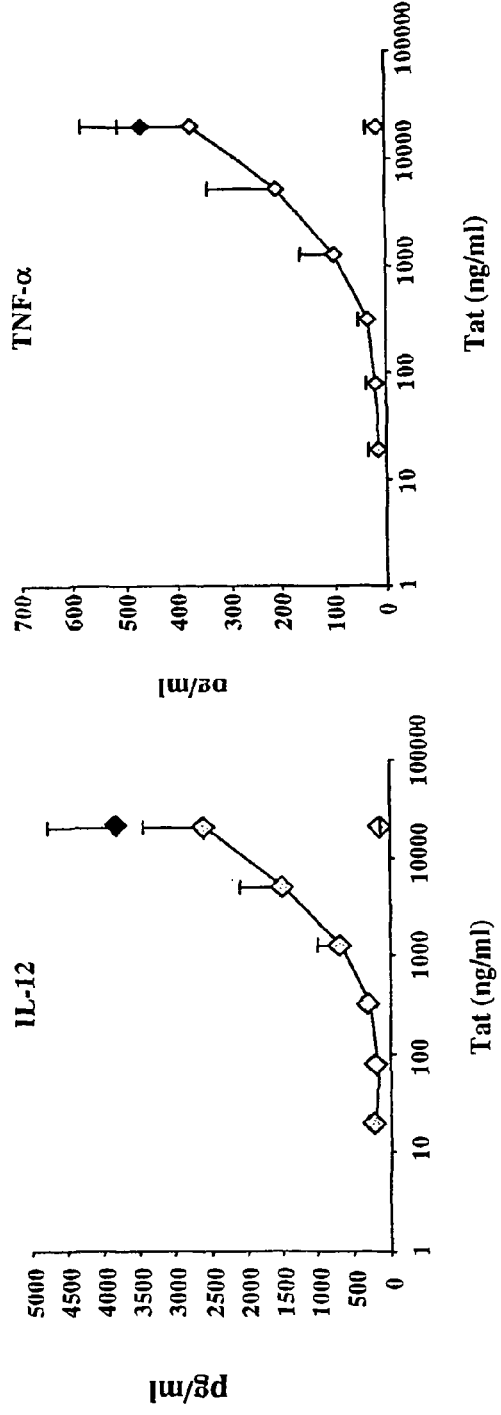
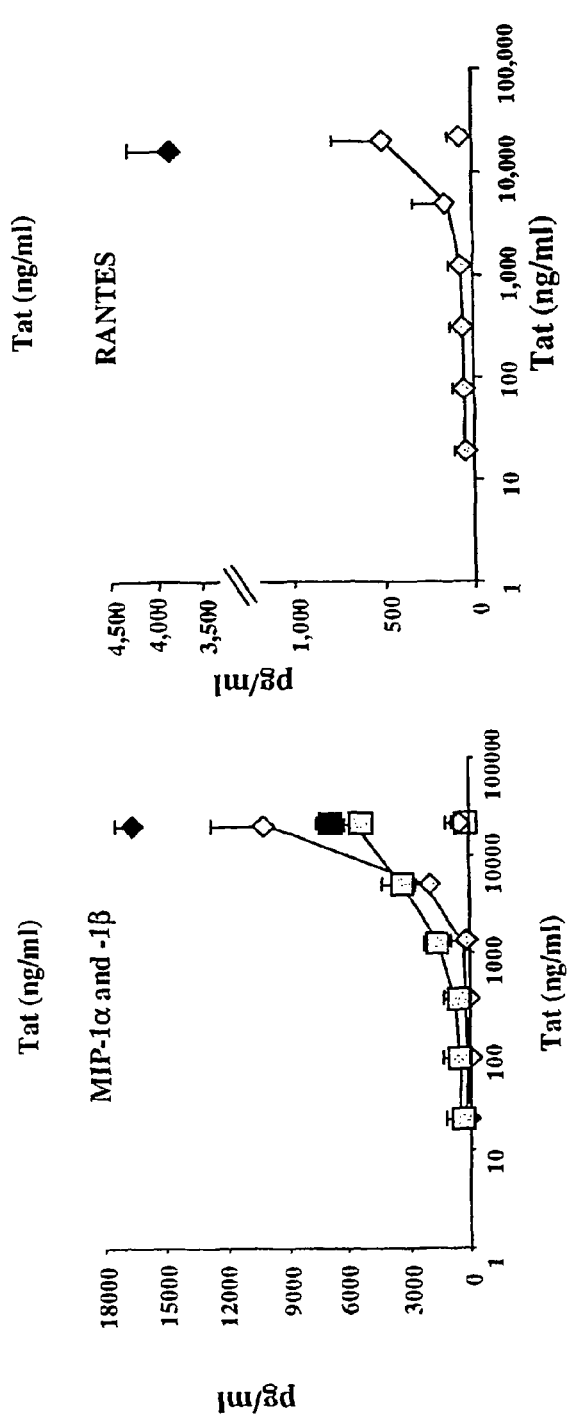
FIG. 18A
FIG. 18B
FIG. 18C
FIG. 18D

| day | Gag alone | Combination (Tat + Gag) |
|---|---|---|
| | ARM 1 (7 animals) | ARM 2 (12 animals) |
| 0 | Gag (10 μg) i.d. | Tat (10 μg) + Gag (10 μg) i.d. (mixed together) |
| 14 | Gag (10 μg) i.d. | Tat (10 μg) + Gag (10 μg) i.d. (mixed together) |
| 28 | Malp-2 + Gag (10 μg) i.n. | Tat (10 μg) + Malp-2 + Gag (10 μg) i.n. (mixed together) |
| 42 | Malp-2 + Gag (10 μg) i.n. | Tat (10 μg) + Malp-2 + Gag (10 μg) i.n. (mixed together) |

Fig. 21

COMPOSITIONS OF ANTIGENS BOUND TO HIV-1 TAT, FRAGMENTS OR DERIVATIVES THEREOF

This application is a national stage application under 35 U.S.C. §371 of international application PCT/EP02/08377, filed Jul. 26, 2002, published in English as International Application Publication No. WO 03/009867, and claims the benefit under 35 U.S.C. §119 of European application No. 01118114.6, filed Jul. 26, 2001.

FIELD OF THE INVENTION

The present invention relies on the novel and unexpected discovery that low amounts (picomolar-nanomolar) of native, substantially monomeric, biologically active HIV-1 Tat, fragments or derivatives thereof, (i) specifically bind, through the RGD domain, to the $\alpha 5\beta 1$ and integrins that are selectively expressed on antigen-presenting cells such as dendritic cells, macrophages and cytokine-activated endothelial cells (henceforth APC), (ii) efficiently enter APC, (iii) promote dendritic cells and endothelial cells maturation and activation, and (iv) access to both the major histocompatibility complex class-I and class-II restricted antigen presentation pathway. Therefore, the present invention intends to exploit these novel findings of the aforementioned inherent and inter-related properties of biologically active HIV-1 Tat, fragments or derivatives thereof, as a delivery system for both antigenic and therapeutic (henceforth collectively referred to as "cargo") molecules for the treatment of certain human diseases, such as, but not limited to, infectious diseases, inflammatory and angiogenic diseases, and tumors, and as an adjuvant and immunomodulator in single or multiple antigen vaccines for preventive and therapeutic vaccination applications, by: 1) selectively targeting, binding and delivering cargo molecules to APC, in the first embodiment of the present invention, 2) by selectively targeting and binding to dendritic cells and endothelial cells thus promoting their maturation and activation, and by inducing Th-1 type immune responses against itself and, most notably, other antigens, in a second embodiment of the present invention.

In particular the present invention relates to, 1) a method for specifically targeting and delivering cargo molecules to APC to immunize or treat humans against infectious, inflammatory and angiogenic diseases or tumors, 2) a method for increasing the immunising activity of other antigens in preventive and therapeutic immunization of humans against infection by one or more pathogens.

The present invention is specifically and univocally concerned with the use of native, substantially monomeric and biologically active HIV-1 Tat protein, fragments or derivatives thereof, to specifically target APC to deliver cargo molecules across the outer cell and nuclear membranes, in a drug or antigen delivery embodiment of the present invention; and to specifically target dendritic cells and endothelial cells to promote their maturation, activation and to induce Th-1 type immune responses against other antigens in a vaccine-adjuvant and immunomodulation embodiment of the present invention.

BACKGROUND OF THE INVENTION

Tat is a regulatory protein of human immunodeficiency virus type 1 (HIV-1) produced very early after infection and essential for virus gene expression, replication and infectivity (Arya 1985; Fisher 1986; Chang 1995). During acute infection of T cells by HIV, Tat is also released in the extracellular milieu and taken-up by neighbour cells (Frankel 1988; Ensoli 1990; Ensoli 1993; Chang 1997) where, according to the concentration, can increase virus infectivity. Specifically, upon uptake Tat can enhance, in infected cells, virus gene expression and replication (Frankel 1988; Ensoli 1993; Chang 1997), and, in uninfected cells, the expression of the $\beta$-chemokines receptors CCR5 and CXCR4 favouring transmission of both macrophage and T lymphocyte-tropic HIV-1 strains (Huang 1998; Secchiero 1999). Extracellular HIV-1 Tat protein is also responsible for the increased frequency and aggressiveness of Kaposi's sarcoma (KS) a vascular tumor particularly frequent in HIV-infected individuals (Friedman-Kien 1981; Safai 1985). In particular, previous work from our and other groups indicated that Tat cooperates with angiogenic and inflammatory cytokines that are highly expressed in KS patients (Samaniego 1998; Ensoli 1994) in inducing new blood vessels formation (angiogenesis) and the growth and locomotion of spindle shaped cells of endothelial cell origin (KS cells) and of activated endothelial cells (Barillari 1992; Albini 1995; Ensoli 1994). Moreover, the sequence comprised between residues 21 and 40 (core domain) in the HIV-1 BH-10 Tat protein has been shown to act as a transactivator, to induce HIV replication and to trigger angiogenesis (International Patent number WO 00/78969 A1). In particular, our data have shown that biologically active Tat binds through its RGD region the integrin receptors $\alpha 5\beta 1$ and $\alpha v\beta 3$ and that this interaction mediates the adhesion, growth and locomotion induced by Tat on KS cells and endothelial cells activated by inflammatory cytokines (Barillari 1993; Barillari 1999a and 1999b). In addition, Tat acts also as a chemotactic factor for these cell types as well as for monocytes and dendritic cells (DC) (Albini 1995; Benelli 1998; Lafrenie 1996; Mitola 1997). Finally, our data demonstrated that KS and HUVE cell migration and invasion are toward the Tat protein is mediated by the binding of the Tat RGD region to the $\alpha_5\beta_1$ and $\alpha v\beta_3$ integrins (Barillari, 1999b). Consistent with these findings, the immune response to Tat has been shown to play a key role in controlling the progression of AIDS and AIDS-associated diseases. In fact, a Tat-specific immune response is present in HIV-1 infected subjects and simian immunodeficiency virus (SIV)-infected monkeys, and correlates inversely with progression to the symptomatic stage of the infection (Reiss 1990; Venet 1992; Rodman 1993; Froebel 1994; Re 1995; Van Baalen 1997; Zagury 1998; Addo 2001). Moreover, vaccination with biologically active Tat protein or tat DNA induces protection against SHIV89.6P virus replication and disease onset which correlates with the presence of Th-1 responses including specific cytotoxic T lymphocytes (CTLs) (Cafaro 1999; Cafaro 2000; Cafaro 2001, and PCT WO99/27958). The same protection data have been more recently observed with a tat-rev vaccine delivered with viral vectors in macaques (Osterhaus 2001). In contrast, a limited containment of the infection has been observed in monkeys vaccinated with inactivated Tat or Tat peptides, in which antibodies and T helper specific responses but no CTLs nor Th-1 responses had been induced (Goldstein 2000; Pauza 2000). Again, the repeated intradermal (i.d.) inoculation of monkeys with native and active Tat protein alone (in the absence of any adjuvant) at low doses (5-6 µg) selectively induced a Th-1 response and specific CTLs in the absence of any significant antibody production (Cafaro 1999 and PCT WO99/27958). These immunological results were recently confirmed in a new vaccination protocol in which native Tat alone was repeatedly inoculated i.d. in 4 monkeys (unpublished data), and are comparable to those induced by i.m. vaccination with tat DNA in a published (Cafaro 2001 and PCT WO99/27958) and in an ongoing study. Similarly, recent work performed in SIV-infected macaques indicate that anti-Tat CTLs are key to control early virus replication after primary infection and exert a selective immune pressure on the virus leading to the appearance of slowly replicating, less pathogenic escape mutants (Allen 2000). Finally, Tat is presented with major histocompatibility complex (MHC) class I antigen (Moy 1996; Kim 1997), hence inducing anti-Tat CTL (Cafaro 1999). Micromolar concentrations of recombinant Tat protein (often of unknown biological activity) or peptides encompassing the basic region of Tat have been shown to enter many different cell types (Frankel 1988; Mann 1991; Ensoli 1993; Chang 1997; Fawell 1994; Moy 1996; Kim 1997). The highly basic charge of Tat residues 48-57, in fact, enables the protein to bind to heparan sulphate proteoglycans (HSPG) that are present on the membrane of all cell types (Chang 1997; Rusnati 1998). After release from acutely infected cells, a fraction of extracellular Tat binds, through its basic residues, to the HSPG (Chang 1997). This protects extracellular Tat from proteolytic degradation, as previously found for several growth factors (reviewed in Raines and Ross, 1992). Upon the binding of its basic region to cell surface HSPG, Tat is internalised through a receptor-independent pathway (Frankel 1988; Rusnati 1998; Tyagi 2001). In fact, Tat residues 49-57 (in the BH-10 Tat sequence) have been indicated to be able to translocate an OVA peptide into the cytosol of DC and to sensitize CD8+ T cells to this peptide (Kim, 1997). Furthermore, the 47-57 Tat sequence (from the BH-10 variant), fused with several effector proteins, has been suggested to be able to deliver them to cells (International patent number WO 01/19393 A1). However, this internalization mechanism requires high (micromolar) concentrations of Tat, occurs with any cell type and it is not sequence-specific. In fact, it has been shown that mutations of this region, which do not change its basic charge, do not affect the properties of the Tat basic region (Barillari 1999b). Similarly, the substitution of the Tat basic region with that of HIV rev or other genes does not change Tat properties. In this regard, the basic region of Tat has been shown to be very similar to the arginin-rich region carried by the members of the small family of proteins known as «penetratins», that are all capable of entering many cell types (Derossi 1998). In fact, arginin homopolymers have been shown to enter cells even more efficiently than Tat basic region (Derossi 1998).

The property of the Tat basic region of being internalized by cells has been exploited to deliver foreign proteins to a variety of cell types (Fawel 1994; Wender 2000; and WO 01/19393). To this purpose, foreign proteins have been conjugated or fused to the Tat basic region which has been used as a carrier for the protein to be transduced (Fawel 1994; Wender 2000; and WO 01/19393). However, the inventor believes that due to the ubiquitous expression of HSPG, Tat basic region cannot be used for selective targeting, delivery and/or uptake of Tat by specific primary cell types, including antigen presenting cells (APC).

APC initiate and drive the type of immune response upon encountering foreign molecules (Bancherau 1998; Bell 1999). Typical APC include monocyte-derived DC (MDDC), T cell blasts (TCB), B-lymphoblastoid cell lines (BLCL) and monocytes-macrophages (Bancherau 1998; Bell 1999). In addition, when activated by inflammatory cytokines also endothelial cells acquire APC functions (Pober 1988). Among these inflammatory cytokines, interleukin (IL)-1, tumor necrosis factor (TNF) and interferon (IFN)γ are key for endothelial cell activation (Pober 1988). Exposure to these cytokines increases in endothelial cells the expression of α5β1 and αvβ3, that are among the several cell surface receptors binding Tat (Barillari 1993, Fiorelli 1999; Benelli 1998; Kolson 1993; Sabatier 1991; Vogel 1993; Boykins 1999; Ganju 1998; Milani 1996; Mitola 1997 and 2000; Weeks 1993; Albini 1996 and 1998; Chang 1997; Lafrenie 1996; Morini 2000; Rusnati 1998). Among all these APC, DC are the most efficient APC and are key to the induction of immune responses against infections and tumors (Banchereau 1998; Bell 1999). Their function is associated with a high expression of MHC and costimulatory molecules (CD40, CD80, CD86) and with the production of cytokines known to activate T lymphocytes, and β-chemokines. Upon encountering the antigens, DC undergo a maturation process characterized by an increase of costimulatory molecules expression and by a reduction of their phagocytic and pinocytic capability (Banchereau 1998; Bell 1999). Further, due to the upregulation of the homing receptor CCR7 and to the downregulation of CCR5, mature DC migrate to lymph nodes where they present antigens to T lymphocytes (Banchereau 1998; Bell 1999).

Prior art indicates that the addition of Tat protein to DC blocks in these cells the extracellular calcium influx, the production of interleukin-12, and the uptake of apoptotic bodies (Zocchi 1997; Rubartelli 1997). As a result, it is predicted that profound impairment of important DC functions including antigen uptake, processing and presentation and induction of Th-1 responses should occur. Further, impairment of phagolysosomal fusion has been reported in peripheral blood monocytes upon exposure to Tat, suggesting impairment in this cell type of both microbicidal and antigen processing (and presentation) functions (Pittis 1996). Moreover, Tat has been reported to induce both monocytes/macrophages and lymphocytes to secrete IL-10 (Masood 1994; Badou 2000), while inhibiting IL-12 production in monocytes (Ito 1998). Finally, exposure of APC to Tat has been reported to impair their capability to organize cell clusters and to properly activate T cells (Mei 1997). Moreover, prior art indicates that Tat profoundly impairs also T cell functions including suppression of responses to mitogens anti-CD3 or specific antigens (Viscidi 1989; Benjouad 1993; Subramanyam 1993; Chirmule 1995; Wrenger 1996; Wrenger 1997; Zagury 1998), T cell hyperactivation (Ott 1997; Li 1997), and T cell apoptosis (Westendorp 1995; Li 1995; McCloskey 1997). Further, inoculation of biologically active Tat has been reported to be immunosuppressive in vivo (Cohen 1999). Part of the effects of Tat on the immune system have been related to upregulation by Tat of the chemokines receptors CCR5 and CXCR4 (Huang 1998; Secchiero 1999), or the direct interaction of Tat with the chemokine receptors CCR2 and CCR3 (Albini 1998a) or with other receptors including CD26 (Gutheil 1994), Flt-1 (Mitola 1997), KDR (Albini 1996; Morini 2000), that are expressed by immune cells, as well as by endothelial cells. Therefore, according to this previous art Tat is expected to drive a Th-2 type of immune response and/or to interfere with or abolish proper APC function and T cell activation.

By contrast, our novel and unexpected finding, supported by experimental evidence exhibited in this patent application, indicate that: (i) APC are specifically targeted by Tat that selectively recognises and enters these cells at pico-nanomolar concentrations, but that this requires the interaction of native, substantially monomeric, biologically active Tat with α5β1, αvβ3 integrins, through the Tat RGD sequence; (ii) and that native, substantially monomeric, biologically active Tat activates, rather than inhibiting, APC function and induces, rather than suppressing, Th-1 type immune responses against itself and, most notably, other antigens. Specifically, our data show that Tat acts not only as an antigen but also as an adjuvant with potent immunomodulatory properties. These properties of Tat, namely of being selectively internalised as biologically active protein by APCs at picomolar-nanomolar concentrations and to act as an adjuvant, are strictly related each other. In particular, we have found, that Tat RGD sequence is key for the internalisation of active Tat by these cells through the α5β1 and αvβ3 integrin receptors. In fact, antibodies or competitor ligands blocking these integrins completely abolish or greatly reduce the uptake of picomolar-nanomolar concentrations of Tat, respectively. This uptake is very rapid, is dose-, cell maturation/differentiation- and time-dependent. Even more unexpectedly, we did not obtain similar results with other APC including monocytes, T cell blasts, or B cell blasts or non-activated endothelial cells. Therefore, these findings are completely novel since prior art indicates that Tat is taken up only at much higher concentrations (micromolar range), through its basic region, by a non-receptor-mediated pathway (Frankel 1988; Mann 1991; Rusnati 1998; Tyagi 2001). This internalization pathway occurs with any cell type, and it is not maturation/differentiation-dependent.

Further, we have found that Tat in its native, substantially monomeric, and biologically active form is absolutely required to observe all the above novel effects which do not occur when Tat is oxidized and inactivated. In fact, Tat has 7 cysteines and it is extremely sensitive to oxidation which, when occurring, causes the loss of native protein conformation and consequent loss of biological activity (Frankel 1989). Therefore, Tat is likely to lose its native conformation and activity when purified with procedures that are not specifically designed at maintaining this protein in its native form. Although established concepts in the field claim that biologically active Tat is toxic (Gallo 1999; Sabatier 1991; Kolson 1993; Westendrop 1995; Purvis 1995), by contrast, the highly purified, biologically active preparations of recombinant Tat utilized by the inventor has no cytotoxic nor pro-apoptotic effects on endothelial cells, DC, macrophages, other cell type tested, nor in vivo in mice or monkeys (Ensoli 1994; Barillari 1999a; Zauli 1993, 1995a and 1995b; Cafaro 1999, 2000 and 2001).

Thus, the inventor believes that full-length, wild type, native, substantially monomeric, and biologically active Tat from any HIV variant or its fragments or derivates containing the RGD region can be used as a highly efficient system for the selective targeting and delivery of molecules to specific cell types expressing the integrins recognized by the Tat RGD region (Barillari 1993, 1999a and 199b; Ensoli 1994). Given the very large amount and ubiquitous distribution of DC, macrophages and endothelial cells in the human body, the inventor believes that the capability of biologically active Tat or its fragments or derivatives containing the RGD sequence of targeting these APC and of driving Th-1 type cellular responses will offer a unique opportunity to, 1) to deliver cargo molecules to these cell types which represent a specific target for Tat and are recruited and activated in infections, pathologic angiogenesis, inflammatory diseases and tumors in the delivery system embodiment of the present invention; 2) induce a potent immune response against not only Tat but also against other antigens delivered by or with Tat, in the vaccine-adjuvant and immunomodulatory embodiment of the present invention. This belief is strongly supported by the successful previous work of the inventor with biologically active Tat as a vaccine to control HIV replication and to block disease onset (Cafaro 1999; Cafaro 2000; Cafaro 2001, and PCT WO99/27958) as opposed to inactivated Tat protein (Goldstein. 2000; Pauza 2000).

The present patent application is substantially different and innovative as compared to our previous patent application WO 99/27958 in many aspects. In fact, the above mentioned application claimed biologically active Tat or Tat encoding DNA to be effective as a vaccine against HIV/AIDS. At the time when said patent application was filed it was not known to us that low (picomolar-nanomolar) amounts of biologically active Tat, or its fragments or derivatives containing the RGD region, (i) specifically target APC and thus we could have not claimed its use as a carrier to selectively deliver cargo molecules to them; (ii) cause EC and DC cell maturation and activation and induce Th-1 type immune responses against different antigens, and thus we could have not claimed its use as a adjuvant and immunomodulator.

Thus, in this invention, biologically active Tat is proposed, in the first embodiment, as a delivery system to deliver to APC (i) different antigens or combinations of antigens for vaccination against different infectious diseases (not only HIV/AIDS) and tumors, or for multivalent vaccination against one or more infectious diseases, and (ii) therapeutic molecules for the treatment of infectious, inflammatory and angiogenic diseases and tumor growth and metastasis; and in the second embodiment, biologically active Tat is proposed as an adjuvant to drive T-cell mediated immune responses against different antigens, and in particular to enhance the immunogenicity of poorly immunogenic antigens, such as those expressed by certain intracellular pathogens as well as tumor cells, by combining or fusing them with biologically active Tat or its fragments or derivatives containing the RGD region.

In summary, the most important innovative aspect which makes the difference with the prior art is that here native, substantially monomeric, and biologically active Tat is claimed as a molecule which exerts different functions, i.e. it is a carrier to selectively deliver antigens to APCs or active compounds to specific tissues, and an adjuvant stimulating immune responses to other antigens. This unexpected properties make native, substantially monomeric, and biologically active Tat suitable for different applications in different infectious diseases (not only AIDS), inflammatory and angiogenic diseases and tumors.

Thus, the inventor believes that native, substantially monomeric, and biologically active Tat, fragments or derivatives thereof, containing the RGD sequence, acts with at least one of the following actions: as delivery system to specific APC or as an adjuvant, and claims that it can be exploited for preventive and therapeutic vaccination and/or drug delivery for the prevention and treatment of HIV/AIDS, other infectious, inflammatory, and angiogenic diseases.

SUMMARY OF THE INVENTION

It is an object of the present invention the use of native, substantially monomeric, and biologically active HIV-1 Tat, fragments or derivatives thereof, to selectively target antigen-presenting cells expressing α5β1 and αvβ3 integrins.

It is another object of the present invention the use of native, substantially monomeric, and biologically active HIV-1 Tat, fragments or derivatives thereof, to selectively target α5β1 and αvβ3 integrins expressed by antigen presenting cells, including dendritic cells, endothelial cells and macrophages, for the uptake of Tat, fragments or derivatives thereof, by these cells.

It is another object of the present invention the use of native, substantially monomeric, and biologically active HIV-1 Tat, fragments or derivatives thereof, to selectively target antigen presenting cells expressing the α5β1 and αvβ3 integrins, including dendritic cells, endothelial cells and macrophages, to induce the maturation and/or the antigen presenting functions of these cells by Tat, fragments or derivatives thereof.

Another object is the use of native, substantially monomeric, and biologically active HIV-1 Tat, fragments or derivatives thereof, combined with one or more antigens, including, but not limited to, antigens from intracellular pathogens (such as viruses, mycobacterium tuberculosis, candida, malaria) and from tumor cells, (such as those from lung, colon, breast, prostatic cancer) in the form of peptides, proteins or DNA encoding them, to selectively target in vitro and in vivo antigen-presenting cells expressing the α5β1 and αvβ3 integrins, including dendritic cells, endothelial cells and macrophages, for preventive and therapeutic vaccination or treatment against infectious diseases and tumors.

Another object is the use of native, substantially monomeric, and biologically active Tat, fragments or derivatives thereof, to selectively deliver in vitro and in vivo one or more antigens to antigen-presenting cells expressing the α5β1 and αvβ3 integrins, including dendritic cells, endothelial cells and macrophages in order to induce immune responses for preventive and therapeutic vaccination or treatment of infectious diseases, inflammatory and angiogenic diseases and tumors.

Another object is the use of native, substantially monomeric, and biologically active Tat, fragments or derivatives thereof, to selectively deliver, intracellularly or to the cell membrane, in vitro and in vivo, to antigen-presenting cells expressing the α5β1 and αvβ3 integrins, including dendritic cells, endothelial cells and macrophages, one or more antigens or therapeutic compounds (such as, but not limited to, antiviral compounds, anti-inflammatory drugs, anti-angiogenic molecules, cytotoxic anti-tumor drugs or immuno-modulating molecules such as, for example chemokines or cytokines, or antibodies) with or without the presence of support particles (such as, but not limited to, microparticles, nanoparticles, liposomes and other particulated delivery systems such as the ones described in Speiser 1991 and Takeuchi, 2001) for preventive and therapeutic vaccination or treatment of infectious diseases, inflammatory and angiogenic diseases and tumors.

Another object is the use of native, substantially monomeric, and biologically active Tat, fragments or derivatives thereof, fused to other proteins or peptides or support particles (as defined in the above) to selectively deliver in vitro and in vivo antigens or therapeutic compounds (as defined in the above) to antigen presenting cells expressing β5β1 and αvβ3 integrins including dendritic cells, endothelial cells and macrophages for combined preventive and therapeutic vaccination or treatment of infectious diseases, inflammatory and angiogenic diseases and tumors.

Another object is the use of native, substantially monomeric, and biologically active Tat, fragments or derivatives thereof, to selectively target in vitro and in vivo cells expressing RGD-binding integrin receptors such as antigen-presenting cells and other cell types capable of taking up Tat via the integrin-mediated pathway, and/or other uptake pathways upon the binding to integrin receptors, in order to deliver antigens or therapeutic molecules (as defined in the above) for preventive and therapeutic vaccination or treatment of infectious diseases, inflammatory and angiogenic diseases and tumors.

Another object is the use of native, substantially monomeric, and biologically active Tat, fragments or derivatives thereof, combined with antigens, adjuvants (such as, but not limited to, Alum, RIBI, ISCOMS, CpG sequences, Lipopeptides) or therapeutic molecules or support particles (as defined in the above) administered by the parenteral (subcute, intramuscular, intradermic) or mucosal (vaginal, rectal, oral, nasal) or topic route for preventive and therapeutic vaccination or treatment against infectious diseases inflammatory, and angiogenic diseases and tumors.

Another object is the use of native, substantially monomeric, and biologically active Tat, fragments or derivatives thereof to selectively deliver in vitro and in vivo antigens or therapeutic molecules (as defined in the above) within or attached to support particles (as defined in the above), to antigen-presenting cells expressing RGD-binding integrin receptors including dendritic cells, endothelial cells and macrophages, for preventive and therapeutic vaccination or treatment against infectious diseases, inflammatory and angiogenic diseases and tumors.

Another object is the use of native, substantially monomeric, and biologically active Tat, fragments or derivatives thereof, to selectively deliver in vitro and in vivo expression vectors including plasmid DNA and bacterial or virus vectors expressing one or more antigens, in the presence or absence of support particles (as defined in the above), to antigen presenting cells expressing RGD-binding integrin receptors, including dendritic cells, endothelial cells and macrophages for preventive and therapeutic vaccination or treatment against infectious diseases, inflammatory and angiogenic diseases and tumors.

Another object is the use of tat DNA or native, substantially monomeric, and biologically active Tat protein, fragments or derivatives thereof, fused or combined with DNA coding for antigens, with or without support particles (as defined in the above), for combined preventive and therapeutic vaccination of infectious diseases, inflammatory and angiogenic diseases and tumors.

Another object is native, substantially monomeric, and biologically active HIV Tat or tat DNA, fragments or derivative thereof, combined or fused with antigens, therapeutic molecules (as defined in the above), adjuvants (as defined in the above), or support particles (as defined in the above) such combination or fusion being defined as the association by means of chemical or physical interactions, or any other interactions, in any combination, such as, for example, but not limited to, the absorption of Tat and a DNA plasmid on nanoparticles; the inclusion of Tat and a synthetic drug in the same pharmaceutical preparation; the association of Tat or a fragment or a derivative thereof with a peptide by chemical crosslinking or by other means; the fusion of Tat, fragment or derivative thereof, with another protein or another peptide upon their expression in bacteria or eucariotic cells through chimeric DNA, where the DNA sequences encoding for the above polypeptides have been fused together using recombinant DNA technologies.

Another object is the use of native, substantially monomeric, and biologically active HIV-1 Tat, fragments or derivatives thereof, as adjuvant to activate or enhance in vitro and in vivo the antigen-presenting function of cells expressing RGD-binding integrin receptors including dendritic cells, endothelial cells and macrophages and to induce Th-1 type immune responses against HIV/AIDS, other infectious diseases and tumors.

Another object are fragments of native, substantially monomeric, and biologically active Tat, defined as Tat peptides from any HIV variant (HIV-1, HIV-2 and other types and subtypes) comprising, alone or associated, the RGD domain (aa 73 to 86 in the HTLV-IIIB, clone BH-10 (SEQ ID NO:4); aa 74 to 84 (SEQ ID NO:6); aa 75 to 83 (SEQ ID NO:8); aa 76 to 82 (SEQ ID NO:10); aa 77 to 81 (SEQ ID NO:12); aa 77 to 82 (SEQ ID NO:14); aa 77 to 83 (SEQ ID NO:16); aa 76 to 83 (SEQ ID NO:18)); the cysteine-rich domain (aa 22 to 37 in the HTLV-IIIB, clone BH-10 (SEQ ID NO:20)); the basic domain (aa 48 to 61 in the HTLV-IIIB, clone BH-10 (SEQ ID NO:22)), combined or not with other HIV-1 Tat peptides including the core domain (aa 38 to 47 in the HTLV-IIIB, clone BH-10 (SEQ ID NO:24)) and/or the amminoterminal region (aa 1 to 20 in the HTLV-IIIB, clone BH-10 (SEQ ID NO:26)).

Another object are fragments of native, substantially monomeric, and biologically active Tat are defined as nucleotide sequences from any HIV variant (HIV-1, HIV-2 and other types and subtypes) comprising, alone or associated, the RGD domain (sequence coding for aa 73 to 86 in the HTLV-IIIB, clone BH-10 (SEQ ID NO:4); sequence coding for aa 74 to 84 in the HTLV-IIIB, clone BH-10 (SEQ ID NO:6); sequence coding for aa 75 to 83 in the HTLV-IIIB, clone BH-10 (SEQ ID NO:8); sequence coding for aa 76 to 82 in the HTLV-IIIB, clone BH-10 (SEQ ID NO:10); sequence coding for aa 77 to 81 in the HTLV-IIIB, clone BH-10 (SEQ ID NO:12); sequence coding for aa 77 to 82 in the HTLV-IIIB, clone BH-10 (SEQ ID NO:14); sequence coding for aa 77 to 83 in the HTLV-IIIB, clone BH-10 (SEQ ID NO:16); sequence coding for aa 76 to 83 in the HTLV-IIIB, clone BH-10 (SEQ ID NO:18)); the cysteine-rich domain (sequence coding for aa 22 to 37 in the HTLV-IIIB, clone BH-10 (SEQ ID NO:20)), the basic domain (sequence coding for aa 48 to 61 in the HTLV-IIIB, clone BH-10 (SEQ ID NO:22)), combined or not with other HIV-1 Tat peptides including the core domain (sequence coding for aa 38 to 47 in the HTLV-IIIB, clone BH-10 (SEQ ID NO:24)) and/or the amminoterminal region (sequence coding for aa 1 to 20 in the HTLV-IIIB, clone BH-10 (SEQ ID NO:26)).

Another object are fragments of Tat from any HIV variant (HIV-1, HIV-2 and other HIV types and subtypes) that comprise one or more T-cell epitopes in their amino acid sequences (HTLV-IIIB, clone BH-10 or 89.6).

Another object are fragments of Tat from any HIV variant (HIV-1, HIV-2 and other HIV types and subtypes) that comprise one or more T-cell epitopes in their nucleotide sequences (HTLV-IIIB, clone BH-10 or 89.6).

Another object are derivatives of Tat which comprise Tat mutants of the HTLV-IIIB, clone BH-10, variant, selected among that ones having the following nucleotide sequences, or part of them: Nucleotide sequence of cys22 mutant and nucleotide sequence of lys41.

Another object are derivatives of Tat which comprise Tat mutants of the HTLV-IIIB, clone BH-10, variant, selected among that ones having the following aminoacid sequences, or part of them: Amino acid sequence of cys22 mutant and amino acid sequence of lys41.

Another object of the present invention is the use of native, substantially monomeric, and biologically active Tat protein acting and combined as above described to produce medicaments to cure affections in the group of infectious diseases, inflammatory and angiogenic diseases, tumors.

Further objects will be evident from the detailed description of the invention.

BRIEF DESCRIPTION OF THE FIGURES

FIG. 8. Rhodaminated Tat is taken up in a dose-dependent fashion by cytokine-activated endothelial cells but not by non-activated cells, as illustrated in FIG. 8A, FIG. 8B, FIG. 8C and FIG. 8D.

FIG. 18. Native, substantially monomeric, and biologically active Tat enhances the production of the cytokines IL-12, and TNF-a and of the β-chemokines MIP-1α, MIP-1β, and RANTES by MDDC, as illustrated in FIG. 18A, FIG. 18B, FIG. 18C and FIG. 18D.

FIG. 21. Scheme of the prime-boost vaccine protocol to assess the role as adjuvant of native, substantially monomeric, and biologically active Tat.

DETAILED DESCRIPTION OF THE INVENTION

Figure 1A:
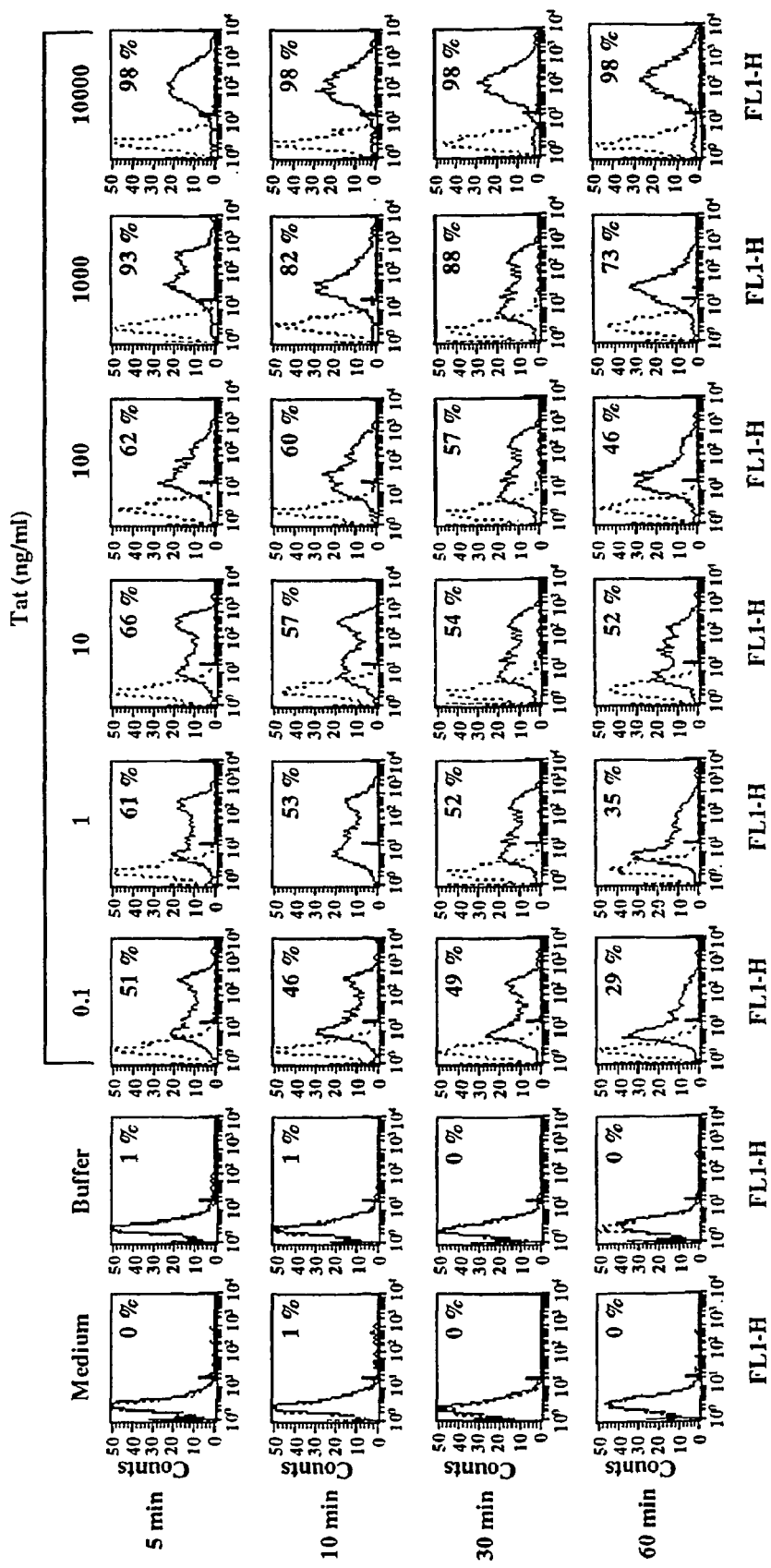
FIG. 1. Native, substantially monomeric, and biologically active Tat is efficiently and selectively taken up in a dose- and time-dependent fashion by MDDC, but not by BLCL or TCB, as illustrated in FIG. 1A, FIG. 1B, FIG. 1C and FIG. 1D.

According to WO 99/27958 the biologically active HIV-1 Tat is defined as a protein capable of 1) entering and localizing in the nuclei of activated endothelial cells or DC, 2) activating the proliferation, migration and invasion of KS cells and cytokine-activated endothelial cells, 3) activating virus replication when added to infected cells as measured by a) the rescue of Tat-defective proviruses in HLM-1 cells after the addition of exogenous protein and/or b) the transactivation of HIV-1 gene expression in cells transfected with a HIV-1 promoter-reporter plasmid, and 4) inducing in mice the development of KS-like lesions in the presence of angiogenic factors or inflammatory cytokines).

As used herein, the term «native» specifically identifies Tat in its native i.e. non-denatured conformation and refers to an isolated Tat protein obtained by conventional techniques of recombinant DNA purified under non-denaturating conditions by techniques that take advantage of the capability of Tat to bind heparin (known in the prior art and widely discussed in the specification).

As used herein, the term «substantially monomeric» refers to the fact that a Tat protein obtained as specified above is mostly (>95%) in a monomeric, as opposed to aggregated, form as determined by HPLC analysis.

As used herein, the term «biologically active» refers to a Tat protein obtained as specified above and that is capable of 1) entering activated endothelial cells or dendritic cells at concentrations up to 10 nM and 2) performing at least one of the following actions: i) activating the proliferation, migration and invasion of Kaposi's sarcoma (KS) cells or cytokine-activated endothelial cells; ii) activating virus replication when added to infected cells as measured by a) the rescue of Tat-defective proviruses in HLM-1 cells after the addition of exogenous protein and/or b) the transactivation of HIV-1 gene expression in cells transfected with a HIV-1 promoter-reporter plasmid; iii) inducing in mice the development of KS-like lesions in the presence of angiogenic factors or inflammatory cytokines.

As used herein the term «DC maturation» refers to a process leading to a progressive decrease of DC pino/phagocytic activity and antigen uptake, and to the concomitant enhancement of DC capability to process and present antigens, being such a process associated with the expression of DC maturation markers [(HLA)-ABC, HLA-DR, CD40, CD80, CD86 and CD83] and production of cytokines and chemokines (IL-12 and TNF-α, RANTES, MIP-1α, MIP-1). As used therein the term «activation »of antigen presenting cells, refers to induction or increase of the capability of taking up, processing and/or presenting antigens leading to enhancement of priming and boosting of immune responses, being such a process associated with the expression of co-stimulatory molecules [(HLA)-ABC, HLA-DR, CD40, CD80, CD86 and CD83, ICAM-1] and production of cytokines and chemokines (IL-12 and TNF-α, RANTES, MIP-1α, MIP-1).

As used therein the term «adjuvant» refers to any substance that, when introduced into a host along with an antigen, enhances the immune responses against that antigen by several mechanisms including, for example, the induction of DC maturation and/or APC activation as defined above.

Based on new data, briefly described below, which are considered novel and unexpected as compared to the previous art, we claim to use biologically active Tat, fragments or derivatives thereof, as a system that by virtue of its inherent and interrelated novel properties may display at least one or both the following features: delivery system and adjuvant.

If Tat protein is oxidized and/or inactivated, it is not suitable for the purposes of the present invention. In fact, only biologically active, but not oxidized or inactivated, Tat protein is very efficiently, rapidly and selectively taken up by MDDC, macrophages and cytokine-activated endothelial cells, in a dose-, time-, and maturation/differentiation-dependent fashion. Uptake of Tat occurs by at least two pathways depending upon the concentration of the protein. At picomolar-nanomolar (0.01-1000 ng/ml) Tat concentrations, uptake of Tat is mostly mediated by the $\alpha_5\beta_1$ and $\alpha_v\beta_3$ receptors through the interaction with the RGD sequence of the protein, while at higher concentrations of Tat an integrin-independent pathway, mediated by the binding of Tat basic region to HSPG, is predominant. Efficient uptake of Tat is observed only with these APC and not with TCB, BLCL, monocytes or non-activated endothelial cells. Upon uptake, Tat induces maturation and activation of MDDC including an increase of the expression of MHC and costimulatory molecules, and production of Th-1 cytokines (TNF-α, IL-12) and β chemokines [Rantes, macrophage inflammatory protein (MIP)-1α, MIP-1β]. All these effects are lost when Tat is oxidized and inactivated. Further, active Tat, but not its oxidized counterpart, enhances both allogeneic and antigen-specific presentation by MDDC, increasing T cell-specific immune responses against heterologous antigens. Thus, due to its capacity to target and efficiently enter specific antigen presenting cells, to enhance their functions and to drive Th-1 specific immune responses, active Tat favors its own presentation and that of other antigens and the induction of specific immune responses, and can also be used to selectively deliver active molecules to these cells.

Based on these new data and on the capacity of Tat to be able to perform the activities (i) to (vi) hereinafter specified, we claim that active Tat functions as a delivery system capable of selectively deliver to antigen presenting cells including dendritic cells, endothelial cells and macrophages antigens or other active molecules and as an adjuvant capable of inducing Th-1 immune responses against antigens by a specific targeting of the most efficient antigen-presenting is cells and by driving specific immune responses. Therefore, biologically active Tat can be used not only as an antigen but also as a Th-1 type adjuvant for other antigens to induce immune responses against pathogens or tumors, and as a delivery system for DC, macrophages and activated endothelial cells for therapeutic intervention against infections, angiogenesis, inflammatory diseases and tumors.

According to the present invention Tat is used as the delivery system to selectively deliver antigens and other active molecules to specific antigen presenting cells including DC, macrophages and cytokine-activated endothelial cells to induce immune responses to antigens, to adjuvate the immune responses to antigens for prophylactic or therapeutic vaccination or treatment of infectious diseases, inflammatory and angiogenic diseases and tumors. For the ease of the presentation the several aspects of the invention will be described separately as follows.

The inventor first found that MDDC have the specific capability of taking up very efficiently soluble active Tat at picomolar-nanomolar concentrations and found that this is a very rapid process with a peak after 5 to 10 min, depending on the concentration of Tat given to the cells. In contrast, the uptake of active Tat by TCB or BLCL is very poor, requiring micromolar concentrations of Tat (10 µg/ml) and much longer periods of time of incubation and, even under these conditions, most Tat remains bound to the cell surface and does not enter cells. Further, active Tat is also rapidly processed by MDDC, as indicated by the reduction of the intracellular staining after 30 min of incubation.

Mature MDDC are able to take up Tat 10- to 100-fold more efficiently than immature cells, as indicated by the values of intracellular staining observed with low concentrations of Tat (100 ng/ml) as compared to those observed with 1 or 10 µg/ml of Tat with immature cells. In addition, Tat uptake requires a native conformation and full biological activity of the protein. In fact, oxidation and inactivation of Tat by exposure to light and air abolishes or markedly reduces (by approximately 100-fold) the uptake observed with active Tat by MDDC. Interestingly, the type of uptake by MDDC observed with oxidized Tat is similar or identical to that of native Tat with TCB and BLCL.

Taken together these data indicate that active Tat targets MDDC and that the selective and efficient uptake of Tat by MDDC is not mediated by the high pino/phagocytic activity of these cells, but it requires specialized uptake pathways that are selectively expressed by immature MDDC and at higher levels by mature MDDC. Further, the different uptake observed at low versus high concentrations of Tat with MDDC indicates the presence of at least 2 different uptake pathways, the first one very efficient occurring at picomolar-nanomolar Tat concentrations and the other one at higher (micromolar) Tat concentrations. In fact, the inventor found that the uptake of low concentrations of Tat is mediated by specific integrins ($\alpha5\beta1$, $\alpha v\beta3$) binding to the RGD region of Tat through a receptor-mediated internalization pathway, whereas at higher Tat concentration the uptake is mediated by the Tat basic region binding HSPG. Monocytes are not efficient in taking up Tat, whereas macrophages take up Tat more efficiently with a dose and time kinetic closer to that of DC indicating that differentiation of monocytes to either DC or macrophages induces selective and efficient mechanisms of Tat uptake. Similarly, the inventor found that endothelial cells activated by IFN$\gamma$, IL-1$\beta$ and TNF-$\alpha$, but not non-activated cells, bind and take up native Tat very efficiently and in fashion similar to MDDC. Tat uptake by activated endothelial cells also occurs via the RGD domain of Tat that binds the $\alpha v\beta3$ and $\alpha5\mu l$ integrins [the classical receptors for vitronectin (VN) and fibronectin (FN)] and at high Tat concentration via the basic region of Tat that binds HSPG of the cell surface and extracellular matrix. Also for endothelial cells, integrin antagonists block uptake of pico-nanomolar but-not higher Tat concentrations. Similarly, uptake of picomolar-nanomolar concentrations of Tat is inhibited by the Tat peptide containing the RGD sequence, while uptake of higher concentrations of Tat is inhibited by the peptide encompassing the basic region of the protein.

Thus, at least two pathways of Tat uptake exist: the first is via binding of the RGD region to integrins which is used by pico-nanomolar concentrations of active Tat and is blocked by integrin competitors, whereas the second pathway of Tat uptake is a relatively lower affinity pathway, is not blocked by the integrin antagonists, becomes predominant only when the concentrations of exogenous Tat are high and/or the time of incubation of the cells with Tat is prolonged, is blocked by the Tat basic peptide and occurs with all cell types. This second pathway may be identical to the receptor-independent pathway observed previously (Allen 2000; Barillari 1999b), via binding to a low affinity site, such as the interaction of the basic region of Tat with cell surface HSPG. Thus, Tat RGD region selectively targets cells expressing RGD-binding integrins receptors such as DC, endothelial cells and macrophages. Further, via this specialized pathway active Tat is very efficiently taken up.

By this specialized pathway the inventor refers to a pathway that requires 1) at least one (RGD) or two Tat domains (basic and RGD), 2) the biological activity of the protein, 3) the native conformation of the protein, substantially in a monomeric form, and 4) integrin membrane receptors. In contrast, little or no uptake is observed with TCB, BLCL and monocytes or non-activated endothelial cells, indicating that. Tat can target and selectively deliver antigens or cargos to specific cell types that are key for the immune response against pathogens and tumors or to treat inflammatory and angiogenic diseases or tumors.

The inventor stresses that according to her, biologically active Tat, but not oxidized Tat, upon binding to specific integrin receptors enters DC, endothelial cells and macrophages and even more importantly, promotes MDDC maturation and function. In fact, active Tat induces a dose-dependent enhancement of the surface expression of human leukocyte antigens (HLA)-ABC, HLA-DR, CD40, CD80, CD86 and CD83 on MDDC. This effect is observed with native but not with oxidized and inactivated Tat. In addition, active Tat induces a dose-dependent increase of the production of both IL-12 and TNF-$\alpha$, cytokines essential for driving a Th-1 type response (Romagnani 1997), and of the $\beta$-chemokines RANTES, MIP-1$\alpha$ and MIP-1$\beta$ which are key players in the effector phase of the lymphocyte response (Moser 2001). Importantly, in both cases the levels are comparable to those induced by the known activator LPS. Again, oxidized and inactivated Tat does not induce these effects. Active Tat also enhances the antigen presenting function of MDDC augmenting the proliferative response of T cells to allogeneic and recall antigens. Taken together these properties indicate that active Tat is not only an antigen but also a potent T cell adjuvant and delivery system to specific cells. The inventor believes that this feature is of a fundamental importance in inducing a specific type (Th-1) of immune response and in increasing this response against heterologous antigens. This also explains the reasons of why vaccination with the inactivated Tat induces different immune responses in vivo which are not protective. Since the induction of Th-1 responses and CTL controls infections by intracellular pathogens as well as tumor growth, the data presented indicate that native Tat protein or tat DNA can be exploited to drive or to increase Th-1 immune responses and CTL activity also against other HIV antigens or non-HIV antigens to support an effective and long-lasting immunity for preventive or therapeutic vaccination as well as to selectively deliver active molecules to DC, activated endothelial cells and macrophages for the treatment of infectious diseases, inflammatory and angiogenic diseases or tumors. In fact, activated endothelial cells, as well as macrophages and DC, are present in inflammatory and angioproliferative diseases, tumors and infectious diseases representing specific target for Tat which can selectively deliver to them antigens, inhibitory compounds or any molecule useful for preventive or therapeutic vaccination or treatment or for diagnostic purposes.

Thus, according to the inventor, biologically active HIV-1 Tat, derivatives or fragments thereof, combined with other molecules including proteins, peptides, nucleic acids or support particles, can be used:

to selectively deliver in vitro and in vivo antigens or active compounds to antigen-presenting cells expressing α5β1 and αvβ3 integrins, including DC, endothelial cells and macrophages in order to induce immune responses for preventive and therapeutic vaccination or treatment of infectious diseases, inflammatory and angiogenic diseases and tumors.

as adjuvant, to activate or to enhance in vitro and in vivo the antigen-presenting function of cells expressing α5β1 and αvβ3 integrins including DC, activated endothelial cells and macrophages and to induce Th-1 type immune responses against HIV/AIDS, other infectious diseases and tumors.

According to the present invention, HIV-1 Tat protein in its biologically active form, has the following amino acid sequence (SEQ ID NO. 2):

NH2-MEPVDPRLEPWKHPGSQPKTA<u>CTNCYCKKCCFHCQVC</u>FITKALGIS

YGR<u>KKRRQRRRPPQGSQ</u>THQVSLSKQPTSQS<u>RGD</u>PTGPKE-COOH and HIV-2 Tat protein in its biologically active form, has the following amminoacid sequence, in which the RGD sequence has been inserted, for example, but not limited to, in position between amminoacid 92 and 93 of the original sequence (SEQ ID NO. 100):

```
NH2-METPLKAPESSLKSCNEPFSRTSEQDVATQELARQGEEILSQLYRP

LETCNNSCYCKRCCYHCQMCFLNKGLGICYERKGRRRRTPKKTKTHRGDP

SPTPDKSISTRTGDSQPTKKQKKTVEATVETDTGPGR-COOH
``` or the threonine at position 105 has been deleted (SEQ ID NO. 102):

```
NH2-METPLKAPESSLKSCNEPFSRTSEQDVATQELARQGEEILSQLYRP

LETCNNSCYCKRCCYHCQMCFLNKGLGICYERKGRRRRTPKKTKTHPSPT

PDKSISTRGDSQPTKKQKKTVEATVETDTGPGR-COOH
``` and any other Tat variant of any HIV-1 and HIV-2 subtype with a sequence homology greater than 50% to SEQ ID NO. 2, 100 or 102; preferably greater than 60%, more preferably greater than 70%, more preferably greater than 80%, more preferably greater than 90%, and in a substantially monomeric form, is able to fulfil at picomolar to nanomolar concentrations (from 0.01 ng/ml to 1 μg/ml, preferably 0.1 ng/ml to 100 ng/ml) at least one of the following criteria:

(i) being selectively and efficiently taken up by antigen-presenting cells including-DC, endothelial cells and macrophages at picomolar nanomolar concentrations (0.01 to 1000 ng/ml) and within 5-10 minutes of exposure to cells.

(ii) promoting the migration (recruitment), invasion and growth of cytokine-activated endothelial cells at picomolar-nanomolar concentrations.

(iii) transactivating HIV gene expression or of rescuing Tat-defective HIV proviruses at nanomolar concentrations.

(iv) activating the maturation and antigen presenting function of DC.

(v) increasing T-cell mediated immune responses, including T-helper and/or cytotoxic activity against itself or heterologous antigens after addition to antigen-presenting cells.

(vi) increasing T-cell mediated immune responses, including T-helper and/or cytotoxic activity against itself or heterologous antigens by addition to effector cells.

Preferably criterium (i) or (ii), preferably both, should be fulfilled, more preferably criterium (i) or (ii) or both in combination with criterium (iii) a) and/or (iii) b) should be fulfilled. The best results will be obtained when all (i) to (vi) criteria are fulfilled. According to the present invention, HIV-1 tat DNA refers to the following nucleotide sequence (SEQ ID NO. 1):

```
5' ATGGAGCCAGTAGATCCTAGACTAGAGCCCTGGAAGCATCCAGGAAG

TCAGCCTAAAACTGCTTGTACCAATTGCTATTGTAAAAAGTGTTGCTTTC

ATTGCCAAGTTTGTTTCATAACAAAAGCCTTAGGCATCTCCTATGGCAGG

AAGAAGCGGAGACAGCGACGAAGACCTCCTCAAGGCAGTCAGACTCATCA

AGTTTCTCTATCAAAGCAGCCCACCTCCCAATCCCGAGGGGACCCGACAG

GCCCGAAGGAATGA 3'
``` and HIV-2 tat DNA refers to the following nucleotide sequence in which the sequence encoding the RGD has been inserted, for example, but not limited to, between nucleotides 276 and 277 of the original sequence (SEQ ID NO. 99):

```
5' ATGGAGACACCCTTGAAGGCGCCAGAGAGCTCATTAAAGTCCTGCAA

CGAGCCCTTTTCACGCACTTCAGAGCAGGATGTGGCCACTCAAGAATTGG

CCAGACAAGGGGAGGAAATCCTCTCTCAGCTATACCGACCCCTAGAAACA

TGCAATAACTCATGCTATTGTAAGCGATGCTGCTACCATTGTCAGATGTG

TTTTCTAAACAAGGGGCTCGGGATATGTTATGAACGAAAGGGCAGACGAA

GAAGGACTCCAAAGAAAACTAAGACTCATCGAGGGGACCCGTCTCCTACA

CCAGACAAATCCATATCCACAAGGACCGGGGACAGCCAGCCAACGAAGAA

ACAGAAGAAGACGGTGGAAGCAACGGTGGAGACAGATACTGGCCCTGGCC

GATAG 3'
``` or the sequence ACC at position 322-324 encoding a threonine has been deleted (SEQ ID NO. 101):

```
5' ATGGAGACACCCTTGAAGGCGCCAGAGAGCTCATTAAAGTCCTGCAA

CGAGCCCTTTTCACGCACTTCAGAGCAGGATGTGGCCACTCAAGAATTGG

CCAGACAAGGGGAGGAAATCCTCTCTCAGCTATACCGACCCCTAGAAACA

TGCAATAACTCATGCTATTGTAAGCGATGCTGCTACCATTGTCAGATGTG

TTTTCTAAACAAGGGGCTCGGGATATGTTATGAACGAAAGGGCAGACGAA

GAAGGACTCCAAAGAAAACTAAGACTCATCCGTCTCCTACACCAGACAAA

TCCATATCCACAAGGGGGACAGCCAGCCAACGAAGAAACAGAAGAAGAC

GGTGGAAGCAACGGTGGAGACAGATACTGGCCCTGGCCGATAG 3'
``` and any other variant of any HIV type and subtype with a sequence homology greater than 40% to SEQ ID NO. 1, 99, or 101 preferably greater than 50%, preferably greater than 60%, more preferably greater than 70%, more preferably greater than 80%, more preferably greater than 90%.

According to the present invention, "fragments of biologically active Tat" are defined as Tat peptides, which correspond to the DNA sequence, from any HIV variant (HIV-1, HIV-2 and other types and subtypes) containing the RGD domain alone or associated with the the cystein-rich domain and/or the basic domain and/or other HIV-1 Tat peptides including the core domain and/or the amminoterminal region, where the RGD domain corresponds to the sequence coding for aa 73 to 86 in the HTLV-IIIB, clone BH-10, as a reference, SEQ ID NO. 3 and corresponding amminoacidic sequence, as a reference, SEQ ID NO.4; sequence coding for aa 74 to 84, SEQ ID NO. 5 and corresponding amminoacidic sequence, as a reference, SEQ ID NO. 6; sequence coding for aa 75 to 83, SEQ ID NO. 7 and corresponding amminoacidic sequence, as a reference, SEQ ID NO.8; sequence coding for aa 76 to 82, SEQ ID NO. 9 and corresponding amminoacidic sequence, as a reference, SEQ ID NO.10; sequence coding for aa 77 to 81, SEQ ID NO. 11 and corresponding amminoacidic sequence, as a reference, SEQ ID NO. 12; sequence coding for aa 77 to 82, SEQ ID NO. 13 and corresponding amminoacidic sequence, as a reference, SEQ ID NO. 14; sequence coding for aa 77 to 83, SEQ ID NO. 15 and corresponding amminoacidic sequence, as a reference, SEQ ID NO. 16; sequence coding for aa 76 to 83, SEQ ID NO. 17 and corresponding amminoacidic sequence, as a reference, SEQ ID NO. 18; the cystein-rich domain to the sequence coding for aa 22 to 37 in the HTLV-IIIB, clone BH-10, as a reference, SEQ ID NO. 19 and corresponding amminoacidic sequence, as a reference, SEQ ID NO. 20; the basic domain to the sequence coding for aa 48 to 61 in the HTLV-IIIB, clone BH-10, as a reference, SEQ ID NO. 21 and corresponding amminoacidic sequence, as a reference, SEQ ID NO. 22, the core domain to sequence coding for aa 38 to 47 in the HTLV-IIB, clone BH-10, as a reference, SEQ ID NO. 23 and corresponding amminoacidic sequence, as a reference, SEQ ID NO. 24 and the amminoterminal region to sequence coding for aa 1 to 20 in the HTLV-IIIB, clone BH-10, as a reference, SEQ ID NO. 25 and corresponding amminoacidic sequence, as a reference, SEQ ID NO. 26.

```
5' CCCACCTCCCAATCCCGAGGGGACCCGACAGGCC    SEQ ID NO. 3
CGAAGGAA 3'

PTSQSRGDPTGPKE                           SEQ ID NO. 4

5' ACCTCCCAATCCCGAGGGGACCCGACAGGCCCG     SEQ ID NO. 5
3'

TSQSRGDPTGP                              SEQ ID NO. 6

5' TCCCAATCCCGAGGGGACCCGACAGGC 3'        SEQ ID NO. 7

SQSRGDPTG                                SEQ ID NO. 8

5' CAATCCCGAGGGGACCCGACA 3'              SEQ ID NO. 9

QSRGDPT                                  SEQ ID NO. 10

5' TCCCGAGGGGACCCG 3'                    SEQ ID NO. 11

SRGDP                                    SEQ ID NO. 12

5' TCCCGAGGGGACCCGACA 3'                 SEQ ID NO. 13

SRGDPT                                   SEQ ID NO. 14

5' TCCCGAGGGGACCCGACAGGC 3'              SEQ ID NO. 15

SRGDPTG                                  SEQ ID NO. 16

5' CAATCCCGAGGGGACCCGACAGGC 3'           SEQ ID NO. 17

QSRGDPTG                                 SEQ ID NO. 18

5' TGTACCAATTGCTATTGTAAAAAGTGTTGCTTTC    SEQ ID NO. 19
ATTGCCAAGTTTGT 3'

CTNCYCKKCCFHCQVC                         SEQ ID NO. 20

5' GGCAGGAAGAAGCGGAGACAGCGACGAAGACCTC    SEQ ID NO. 21
CTCAAGGC 3'

GRKKRRQRRRPPQG                           SEQ ID NO. 22

5' TTCATAACAAAAGCCTTAGGCATCTCCTAT 3'     SEQ ID NO. 23

FITKALGISY                               SEQ ID NO. 24

5' ATGGAGCCAGTAGATCCTAGACTAGAGCCCTGGA    SEQ ID NO. 25
AGCATCCAGGAAGTCAGCCTAAAACT 3'

MEPVDPRLEPWKHPGSQPKT                     SEQ ID NO. 26
```

T-cell-epitopes according to the invention are preferably the following, in their nucleotide sequence and corresponding amino acid sequences (HTLV-IIIB, clone BH-10 or 89.6, as a reference):

```
Epitope 1 (aa 1-20):
5' ATGGAGCCAGTAGATCCTAGACTAGAGCCCTG       SEQ ID NO. 27
GAAGCATCCAGGAAGTCAGCCTAAAACT 3',

MEPVDPRLEPWKHPGSQPKT,                    SEQ ID NO. 28

Epitope 2 (aa 11-24):
5' TGGAAGCATCCAGGAAGTCAGCCTAAAACTGC       SEQ ID NO. 29
TTGTACCAAT 3',

WKHPGSQPKTACTN,                          SEQ ID NO. 30

Epitope 3 (aa 21-40):
5' GCTTGTACCAATTGCTATTGTAAAAAGTGTTG       SEQ ID NO. 31
CTTTCATTGCCAAGTTTGTTTCATAACA 3',

ACTNCYCKKCCFHCQVCFIT,                    SEQ ID NO. 32

Epitope 4 (aa 36-50):
5' GTTTGTTTCATAACAAAAGCCTTAGGCATCTC       SEQ ID NO. 33
CTATGGCAGGAAG 3',

VCFITKALGISYGRK,                         SEQ ID NO. 34

Epitope 5 (aa 83-102):
5' GGCCCGAAGGAACAGAAGAAGAAGGTGGAGAG       SEQ ID NO. 35
AGAGACAGAGACAGATCCGGTCCATCAG 3',

5 GPKEQKKKVERETETDPVHQ,                  SEQ ID NO. 36

Epitope 6 (aa 1-15):
5' ATGGAGCCAGTAGATCCTAGACTAGAGCCCTG       SEQ ID NO. 37
GAAGCATCCAGGA 3',

MEPVDPRLEPWKHPG,                         SEQ ID NO. 38

Epitope 7 (aa 6-20):
5' CCTAGACTAGAGCCCTGGAAGCATCCAGGAAG       SEQ ID NO. 39
TCAGCCTAAAACT 3',

PRLEPWKHPGSQPKT,                         SEQ ID NO. 40

Epitope 8 (aa 11-25):
5' TGGAAGCATCCAGGAAGTCAGCCTAAAACTGC       SEQ ID NO. 41
TTGTACCAATTGC 3',

WKHPGSQPKTACTNC,                         SEQ ID NO. 42

Epitope 9 (aa 16-30):
5' AGTCAGCCTAAAACTGCTTGTACCAATTGCTA       SEQ ID NO. 43
TTGTAAAAAGTGT 3',

SQPKTACTNCYCKKC,                         SEQ ID NO. 44
```

-continued

Epitope 10 (aa 21-35):
5' GCTTGTACCAATTGCTATTGTAAAAAGTGTTG CTTTCATTGCCAA 3', SEQ ID NO. 45

ACTNCYCKKCCFHCQ, SEQ ID NO. 46

Epitope 11 (aa 26-40):
5' TATTGTAAAAAGTGTTGCTTTCATTGCCAAGT TTGTTTCATAACA 3', SEQ ID NO. 47

YCKKCCFHCQVCFIT, SEQ ID NO. 48

Epitope 12 (aa 31-45):
5' TGCTTTCATTGCCAAGTTTGTTTCATAACAAA AGCCTTAGGCATC 3', SEQ ID NO. 49

CFHCQVCFITKALGI, SEQ ID NO. 50

Epitope 13 (aa 36-50):
5' GTTTGTTTCATAACAAAAGCCTTAGGCATCTC CTATGGCAGGAAG 3', SEQ ID NO. 51

VCFITKALGISYGRK, SEQ ID NO. 52

Epitope 14 (aa 41-55):
5' AAAGCCTTAGGCATCTCCTATGGCAG GAAGA AGCGGAGACAGCGA 3', SEQ ID NO. 53

KALGISYGRKKRRQR, SEQ ID NO. 54

Epitope 15 (aa 46-60):
5' TCCTATGGCAGGAAGAAGCGGAGACAGCGAC GAAGACCTCCTCAA 3', SEQ ID NO. 55

SYGRKKRRQRRRPPQ, SEQ ID NO. 56

Epitope 16 (aa 51-65):
5' AAGCGGAGACAGCGACGAAGACCTCCTCAAG GCAGTCAGACTCAT 3', SEQ ID NO. 57

KRRQRRRPPQGSQTH, SEQ ID NO. 58

Epitope 17 (aa 56-70):
5' CGAAGACCTCCTCAAGGCAGTCAGACTCATCA AGTTTCTCTATCA 3', SEQ ID NO. 59

RRPPQGSQTHQVSLS, SEQ ID NO. 60

Epitope 18 (aa 61-75):
5' GGCAGTCAGACTCATCAAGTTTCTCTATCAAAG CAGCCCACCTCC 3', SEQ ID NO. 61

GSQTHQVSLSKQPTS, SEQ ID NO. 62

Epitope 19 (aa 66-80):
5' CAAGTTTCTCTATCAAAGCAGCCCACCTCCCAA TCCCGAGGGAC 3', SEQ ID NO. 63

QVSLSKQPTSQSRGD, SEQ ID NO. 64

Epitope 20 (aa 71-85):
5' AAGCAGCCCACCTCCCAATCCCGAGGGACCC GACAGGCCCGAAG 3', SEQ ID NO. 65

KQPTSQSRGDPTGPK, SEQ ID NO. 66

Epitope 21 (aa 76-90):
5' CAGTCCCGAGGGGACCCGACAGGCCCGAAGGA ACAGAAGAAGAAG 3', SEQ ID NO. 67

QSRGDPTGPKEQKKK, SEQ ID NO. 68

Epitope 22 (aa 21-29):
5' GCTTGTACCAATTGCTATTGTAAAAAG 3', SEQ ID NO. 69

ACTNCYCKK, SEQ ID NO. 70

Epitope 23 (aa 26-34):
5' TATTGTAAAAAGTGTTGCTTTCATTGC 3', SEQ ID NO. 71

YCKKCCFHC, SEQ ID NO. 72

Epitope 24 (aa 31-39):
5' TGCTTTCATTGCCTTGTTTGTTTCATA 3', SEQ ID NO. 73

CFHCQVCFI, SEQ ID NO. 74

Epitope 25 (aa 36-44):
5' GTTTGTTTCATAACAAAAGCCTTAGGC 3', SEQ ID NO. 75

VCFITKALG, SEQ ID NO. 76

Epitope 26 (aa 41-49):
5' AAAGCCTTAGGCATCTCCTATGGCAGG 3', SEQ ID NO. 77

KALGISYGR, SEQ ID NO. 78

Epitope 27 (aa 46-54):
5' TCCTATGGCAGGAAGAAGCGGAGACAG 3', SEQ ID NO. 79

SYGRKKRRQ, SEQ ID NO. 80

Epitope 28 (aa 51-59):
5' AAGCGGAGACAGCGACGAAGACCTCCT 3', SEQ ID NO. 81

KRRQRRRPP, SEQ ID NO. 82

Epitope 29 (aa 56-64):
5' CGAAGACCTCCTCAAGGCAGTCAGACT 3', SEQ ID NO. 83

RRPPQGSQT, SEQ ID NO. 84

Epitope 30 (aa 61-69):
5' GGCAGTCAGACTCATCAAGTTTCTCTA 3', SEQ ID NO. 85

GSQTHQVSL, SEQ ID NO. 86

Epitope 31 (aa 66-74):
5' CAAGTTTCTCTATCAAAGCAGCCCACC 3', SEQ ID NO. 87

QVSLSKQPT, SEQ ID NO. 88

Epitope 32 (aa 71-79):
5' AAGCAGCCCACCTCCCAATCCCGAGGG 3', SEQ ID NO. 89

KQPTSQSRG, SEQ ID NO. 90

Epitope 33 (aa 76-84):
QSRGDPTGP, SEQ ID NO. 91

5' CAATCCCGAGGGGACCCGACAGGCCCG 3', SEQ ID NO. 92

Epitope 34 (aa 81-89):
5' CCGACAGGCCCGAAGGAACAGAAGAAG 3'. SEQ ID NO. 93

PTGPKEQKK. SEQ ID NO. 94

According to the present invention, "derivatives of Tat" include Tat mutants of the HTLV-IIIB, clone BH-10 variant, selected among the ones having the following:

nucleotide sequences:

Nucleotide sequence of cys22 mutant (SEQ ID NO. 95):

5' ATGGAGCCAGTAGATCCTAGACTAGAGCCCTGGAAGCATCCAGGAAG

TCAGCCTAAAACTGCTGGTACCAATTGCTATTGTAAAAAGTGTTGCTTTC

ATTGCCAAGTTTGTTTCATAACAAAAGCCTTAGGCATCTCCTATGGCAGG

AAGAAGCGGAGACAGCGACGAAGACCTCCTCAAGGCAGTCAGACTCATCA

-continued

```
AGTTTCTCTATCAAAGCAGCCCACCTCCCAATCCCGAGGGGACCCGACAG

GCCCGAAGGAATGA 3'
```

Amino acid sequence of cys22 mutant (SEQ ID NO. 96):

```
NH2-MEPVDPRLEPWKHPGSQPKTAGTNCYCKKCCFHCQVCFITKALGIS

YGRKKRRQRRRPPQGSQTHQVSLSKQPTSQSRGDPTGPKE-COOH
```

Nucleotide sequence of lys41 (SEQ ID NO. 97):

```
5' ATGGAGCCAGTAGATCCTAGACTAGAGCCCTGGAAGCATCCAGGAAG

TCAGCCTAAAACTGCTTGTACCAATTGCTATTGTAAAAAGTGTTGCTTTC

ATTGCCAAGTTTGTTTCATAACAAACGCCTTAGGCATCTCCTATGGCAGG

AAGAAGCGGAGACAGCGACGAAGACCTCCTCAAGGCAGTCAGACTCATCA

AGTTTCTCTATCAAAGCAGCCCACCTCCCAATCCCGAGGGGACCCGACAG

GCCCGAAGGAATGA 3'.
```

Amino acid sequence of lys41 (SEQ ID NO. 98):

```
NH2-MEPVDPRLEPWKHPGSQPKTACTNCYCKKCCFHCQVCFITTA

LGISYGRKKRRQRRRPPQGSQTHQVSLSKQPTSQSRGDPTGPKE-COOH
```

Are considered within the scope of the present invention:
DNA sequences having homology of at least 60% with the DNA sequences described in the above, preferably with homology of at least 70%, more preferably of at least 80%, more preferably of at least 90%.
aminoacid sequences having homology of at least 40% with the aminoacid sequences described in the above, preferably with homology of at least 50%, preferably with homology of at least 60%, preferably with homology of at least 70%, more preferably of at least 80%, more preferably of at least 90%.

According to the present invention, "Infectious diseases" include those caused by human or animal herpesviruses, hepatitis viruses, *Mycobacterium Tuberculosis*, Malaria plasmodia, *Candida*, Lysteria, Influenza virus and other infections caused in humans or animals by other intracellular or extracellular pathogens, including but not limited to, sexual infectious diseases, endocarditis, urinary tract infections, osteomyelitis, cutaneous infections, or *streptococcus* and *staphylococcus* infections, *pneumococcus* infections, tetanus, meningococcus infections, tuberculosis, malaria, candidosis, infections by *Helicobacter, salmonella*, syphilis, herpetic infections (including varicella, mononucleosis and Epstein-Barr-derived infections, human herpesvirus-8 infection, cytomegalovirus, herpes labialis and genitalis), hepatitis virus infection (A, B, C, D, G), papilloma virus-derived infections, influenza, lysteria, *vibrio cholerae*. According to the present invention, "inflammatory diseases" are defined as an allergy or inflammation associated or not with a viral, bacterial or parasitic infection, including but not limited to immune-mediated cutaneous diseases, Lupus erythematous systemic, rheumatoid arthritis, systemic sclerosis, dermatomiositis, Sjögren syndrome, Good pasture syndrome, vasculitis, sarcoidosis, osteoarthrosis, infectious arthritis, psoriasis, Chron disease, rectocolitis ulcerosus, tyroiditis, scleroderma, allergic diseases.

According to the present invention, "angiogenic diseases" are defined as non-neoplastic angioproliferative diseases including diabetic retinopathy, retrolental fibroplasia, trachoma, vascular glaucoma, psoriasis, immune inflammation, non-immune inflammation, atherosclerosis, excessive wound healing, angiodermatitis, colon angiodisplasia, angioedema and angiofybromas.

According to the present invention, "tumors" are defined as benign and malignant tumors including tumors of soft tissues, bones, cartilages and blood, such as, but not limited to, Kaposi's sarcoma and other neoplasia of the skin, lung, breast, gut, liver, pancreas, endocrine system, uterus, ovary, sarcomas, acute and chronic leukemia, and neoplasia of lymphatic cells.

According to the present invention, "therapeutic compounds" are defined as other antigens (proteins, peptides or DNA) or active molecules According to the present invention, "support particles" are defined as, but not limited to, microparticles, nanoparticles, liposomes and other particulated delivery systems.

According to the present invention, "non-HIV antigens or other antigens" includes any molecule or moiety recognized by immune cells with the exclusion of HIV antigens HIV-1 Tat, Rev, Nef, Gag.

Tat according to the invention can be used to treat: infectious diseases, inflammatory diseases, angiogenic diseases, tumors.

The Tat combinations as in the above can be mixed with adjuvants, diluents, eccipients, carriers and other substances known in the art to make medicaments for the scopes expressed. Such medicaments can be obtained in form of tablets, pills, sprays, injectable solutions, suspensions, powders, creams, ointments, for parenteral (subcute, intramuscular, intradermic), mucosal (vaginal, rectal, oral, nasal) administration or topical route with routes depending on the kind of disease and type of formulation.

DETAILED DESCRIPTION OF THE FIGURES

FIG. 1. Biologically active Tat is efficiently and selectively taken up in a dose -and time-dependent fashion by MDDC, but not by BLCL or TCB. A, MDDC were obtained from peripheral blood monocytes of 14 different healthy human donors according to established methods (Fanales Belasio 1997). Briefly, peripheral blood mononuclear cells (PBMC) were isolated by density gradient separation (Ficoll-Paque Research Grade, Pharmacia Biotech, Uppsala, Sweden). Monocytes were further purified by incubation with anti-CD14-coated microbeads (Miltenyi Biotec, Bergisch Gladbach, Germany), followed by sorting with a magnetic device (MiniMacs Separation Unit, Miltenyi) according to the manufacturer's instructions. The purity of monocytes was always >95%, as assessed by flow cytometry (FACScan, Becton Dickinson, S. Jose, Calif.). Monocytes were induced to differentiate to DC (MDDC) by 6 days culture in complete medium in the presence of GM-CSF (200 ng/ml) (Leucomax, Novartis, Origgio, Italy) and IL-4 (100 ng/ml) (Peprotech, London, UK). Differentiation to DC was assessed by morphologic observation and by the detection of specific surface markers (HLA-DR, CD86, CD83, CD40, CD80) by flow cytometry. MDDC were then cultured at the density of $2\times10^5$ per ml in complete medium in the presence of serial concentrations (0.1 to 10,000 ng/ml) of active HIV-1 Tat or with reconstitution buffer or medium alone (negative controls) for 5, 10, 30 or 60 min at 37° C. in the dark. Tat protein was expressed from *E. coli* and purified as previously described (Ensoli 1993; Chang 1997; Ensoli 1994) and tested prior to use by cell growth assays and HIV-LTR transactivation, as described (Ensoli 1993; Chang 1997; Ensoli 1994). Tat protein was resuspended in degassed phosphate buffered saline, 0.1% bovine serum lo albumin (PBS -BSA). Precautions were taken to avoid oxidation and loss of activity of Tat as described elsewhere (Ensoli 1993; Chang 1997; Ensoli 1994). Cells were then washed with cold medium and treated for 10 min at 37° C. with trypsin-EDTA (Life-Technologies, Paisley, UK) to remove any externally bound protein. After fixation and permeabilization, MDDC were stained with affinity-purified rabbit polyclonal anti-Tat IgG antibodies (Ensoli 1993; Chang 1997; Ensoli 1994) or rabbit IgG control antibodies (ICN Biomedicals, Opera, Italy), followed by FITC-conjugated anti-rabbit Ig (Pierce, Rockford, IL). Fluorescence was analysed by flow cytometry and results expressed as the percentage of positive cells as compared to isotype-stained samples. To demonstrate the specific intracytoplasmatic localization of the protein, staining with anti-Tat antibodies was always performed also with non-permeabilized MDDC. The percentage of positive cells (as compared to isotype stained samples) is reported into the boxes. Data shown are from one representative donor out of 14 tested, whose levels of Tat uptake were the closest to the median of the values observed with all donors tested at both 10 min (49%, 52%, 49%, 70%, 94%, 98% positive cells for 0.1, 1, 10, 100, 1000 and 10,000 ng/ml) and 30 min (49%, 45%, 54%, 65%, 95%, 98% positive cells for 0.1, 1, 10, 100, 1000 and 10,000 ng/ml), respectively. B, MDDC were incubated with the active Tat protein (10 to 1000 ng/ml) for 10 or 30 min, as reported above and both permeabilized or non permeabilized cells were analyzed by FACS to demonstrate specific uptake of Tat. C and D, BLCL (circles) were generated by culturing human PBMC from 2 healthy donors for 2 h in the presence of supernatants from the Epstein-Barr virus producer B95-8 marmoset cell line, and further expansion for at least 4 weeks as described earlier (Micheletti 1999). TCB (triangles) were obtained by stimulation of human PBMC from 4 healthy donors with phytohemagglutinin (PHA) 1 µg/ml (Murex Diagnostics, Chatillon, France) for 3 days and further expansion for 2 weeks in complete medium supplemented with rIL-2 10 IU/ml (Becton Dickinson Labware, Bedford, MA) as described earlier (Micheletti 1999). BLCL and TCB were cultured at 5×105/m1 in complete medium in the presence of active Tat at concentrations ranging from 100 to 10,000 ng/ml, reconstitution buffer or medium alone for 30 (FIG. 1C) or 60 (FIG. 1D) min at 37° C. in the dark and stained for intracellular Tat detection as reported above. Data are compared with those of MDDC (squares) cultured for the same times and with the same doses of the protein and chosen as a representative example since the levels of Tat uptake with this donor were very close to the median from 11 different donors tested (54%, range 17-91%, 65%, range 27-91%, and 95%, range 83-99%, of positive cells, at 10, 100 and 1,000 ng/ml of Tat, after 30 min of culture, respectively).

FIG. 2. Uptake of biologically active Tat by MDDC increases with cell maturation and it is lost by oxidation and inactivation of the protein. A, MDDC were or were not induced to maturation with LPS for 18 h, and then incubated for 10 and 30 min in the presence of the active Tat protein (1 to 1000 ng/ml) as reported above. The data shown are from a donor who had lower uptake levels than the median values of all donors tested and that was chosen because well illustrates the increase of Tat uptake induced by cell maturation. B, MDDC were incubated for 10 min in the presence of active or oxidized (by exposure to light and air for 18 h) Tat protein (10 to 1000 ng/ml) and processed as reported above. The biological activity of native versus oxidized Tat used in the experiments is reported in Table I.

Figure 3A:
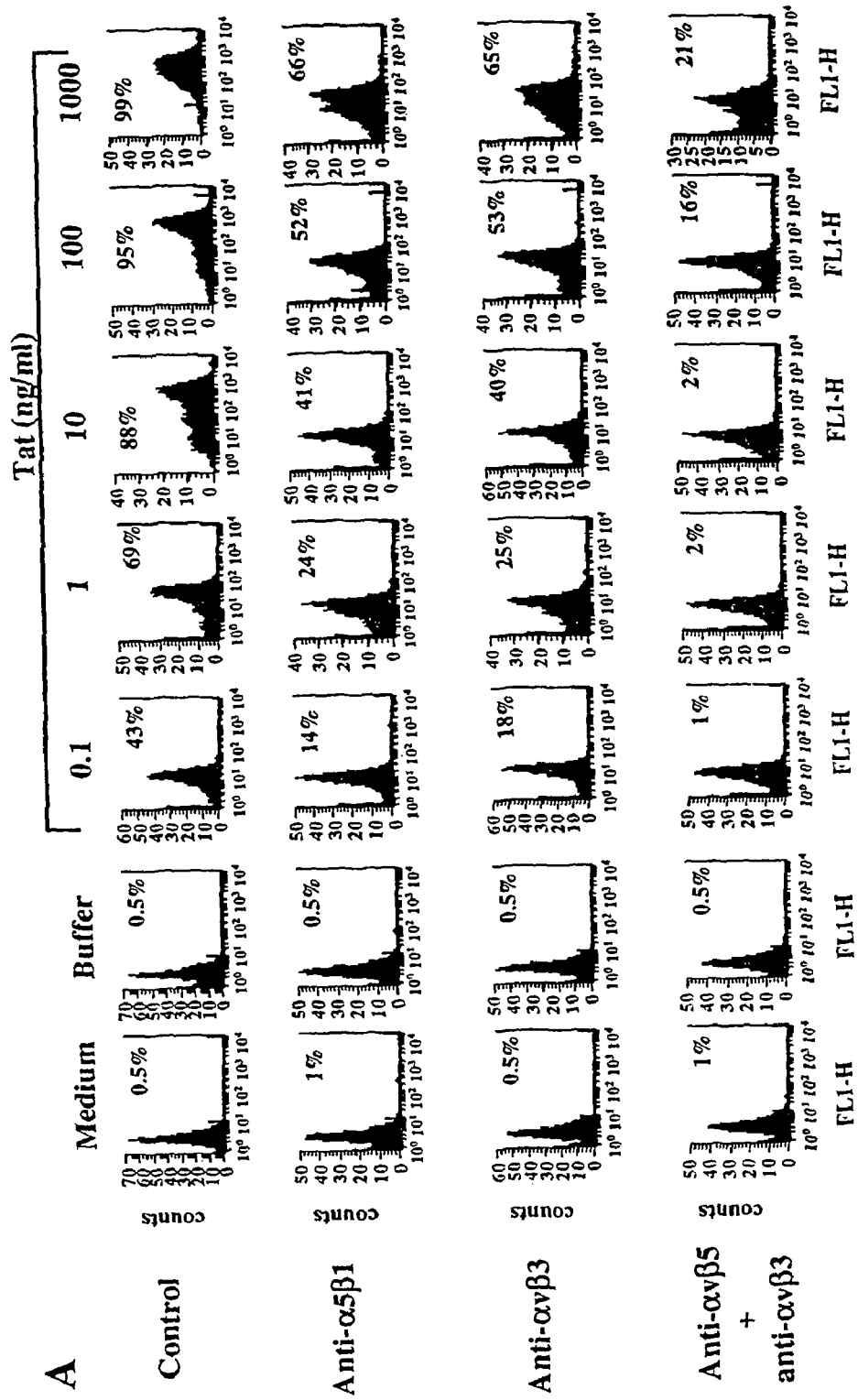
FIG. 3. Anti-α5β1 and anti-αvβ3 antibodies block uptake of native, substantially monomeric, and biologically active Tat by MDDC, as illustrated in FIG. 3A and FIG. 3B.
Figure 3B:
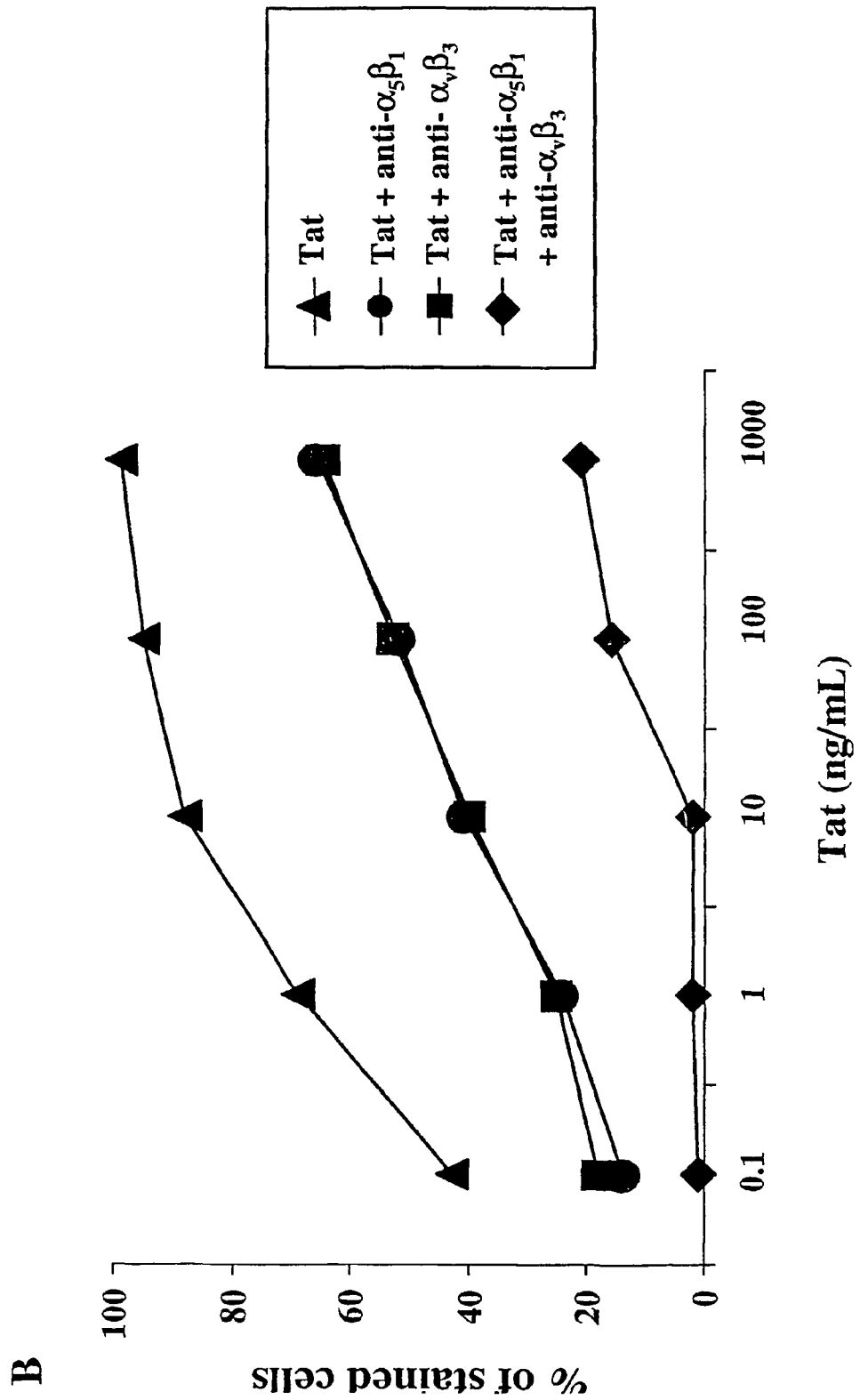

FIG. 3. Anti-α5β1 and anti-αvβ3 antibodies block uptake of active Tat by MDDC. MDDC were incubated (5×10⁵/ml) in complete medium [RPMI 15% fetal bovine serum (FBS)] in the presence of monoclonal antibodies directed against the α5β1 and αvβ3 integrins (10 □g/ml, Chemicon, Temecula, Calif.), alone or combined, for 2 h at 4° C. Subsequently, active Tat protein was added at doses ranging from 0.1 to 1000 ng/ml, for 10 min at 37° C. in the dark. After washing with cold complete medium, cells were processed and stained as described in FIG. 1. Data from a representative donor out of three are shown. A, Flow cytometric analysis of MDDC stained with anti-Tat antibodies. The percentage of positive cells (as compared to isotype stained samples) is reported into the boxes. The uptake of Tat is detected at all doses of the protein (up to 99% at 1000 ng/ml), whereas it is inhibited by preincubation of the cells with anti-α5β1 or anti-αvβ3 antibodies. The presence of both antibodies completely abolishes the uptake of picomolar concentrations of Tat and strongly reduces it up to the highest dose tested (21%). B, the same data are represented in a dot-plot to better appreciate the inhibitory effects of antibodies to β5β1 or αvβ3 integrins on Tat uptake by MDDC.

Figure 4A:
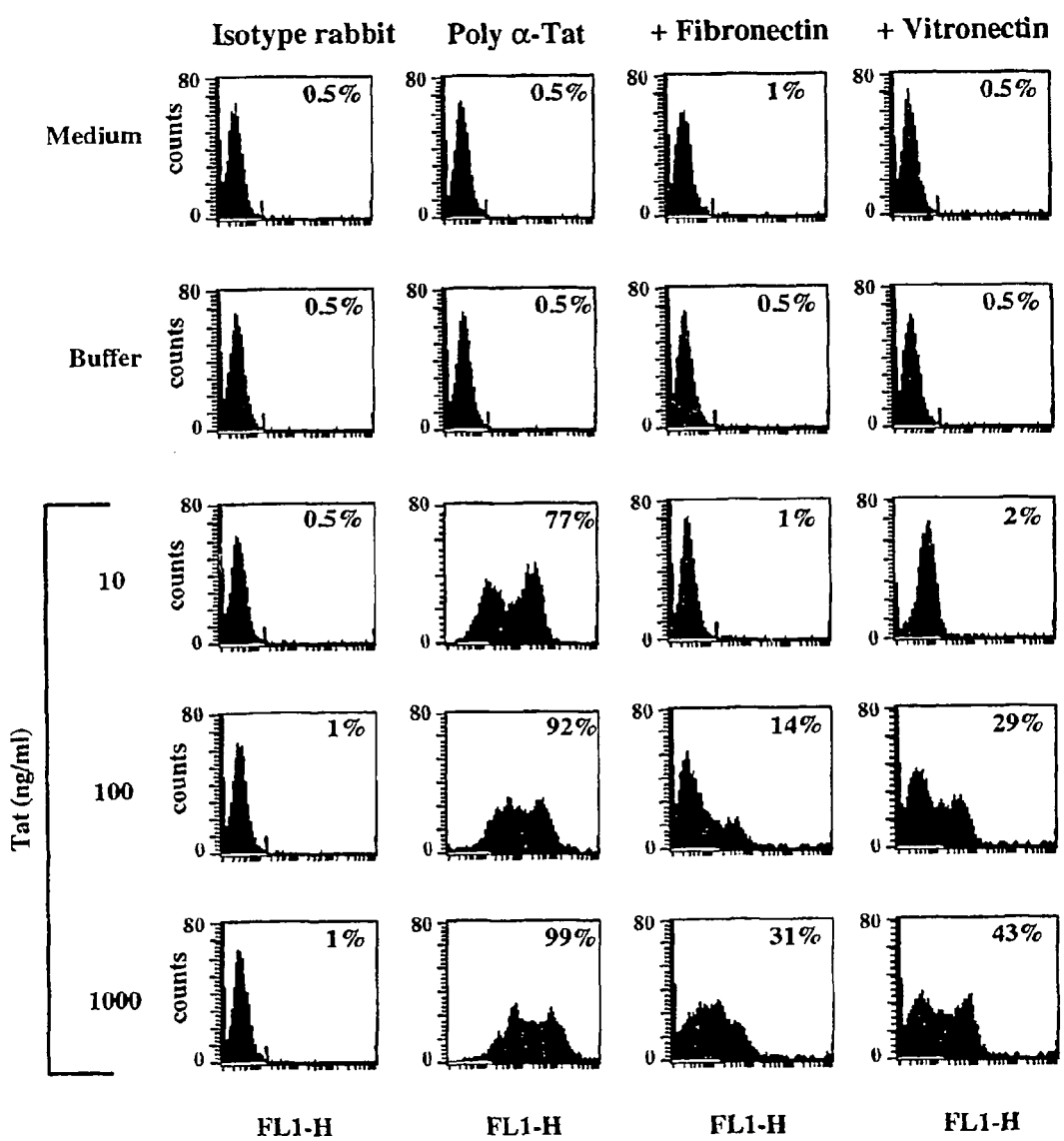
FIG. 4. Fibronectin and vitronectin block uptake of native, substantially monomeric, and biologically active Tat by MDDC, as illustrated in FIG. 4A and FIG. 4B.
Figure 4B:
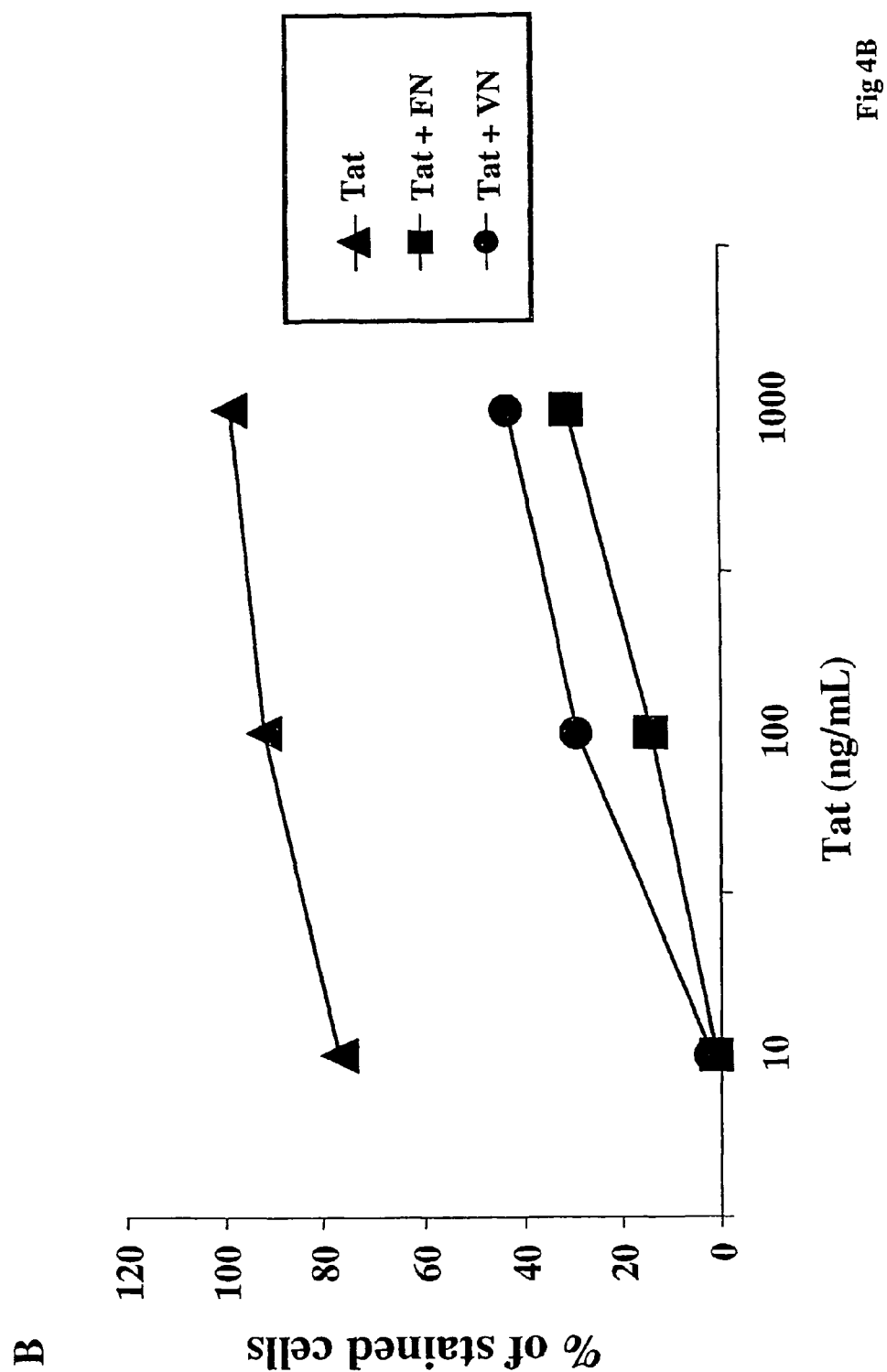

FIG. 4. Fibronectin and vitronectin block the uptake of active Tat by MDDC. MDDC (5×10⁵/ml) were incubated in complete medium (RPMI 15% FBS) in the presence of human plasma-derived FN or VN (25 µg/ml, Sigma-Aldrich, Stenheim, Germany), for 2 h at 4° C. Tat protein was then added at doses ranging from 10 to 1000 ng/ml, for 10 min at 37° C. in the dark. After washing with cold complete medium, cells were processed and stained as described in FIG. 1. Data from a representative donor out of three are shown. A, Flow cytometric analysis of MDDC stained with anti-Tat antibodies. The percentage of positive cells (as compared to isotype stained samples) is reported into the boxes. The uptake of Tat is detected at all doses of the protein (up to 99% at 1000 ng/ml). When cells are pre-incubated with FN or VN the uptake is greatly reduced and completely abolished at the lowest doses of Tat (1% and 2%, respectively, at 10 ng/ml). B, the same data are represented in a dot plot to better appreciate the inhibitory effects of FN and VN on Tat uptake by MDDC.

Figure 5A:
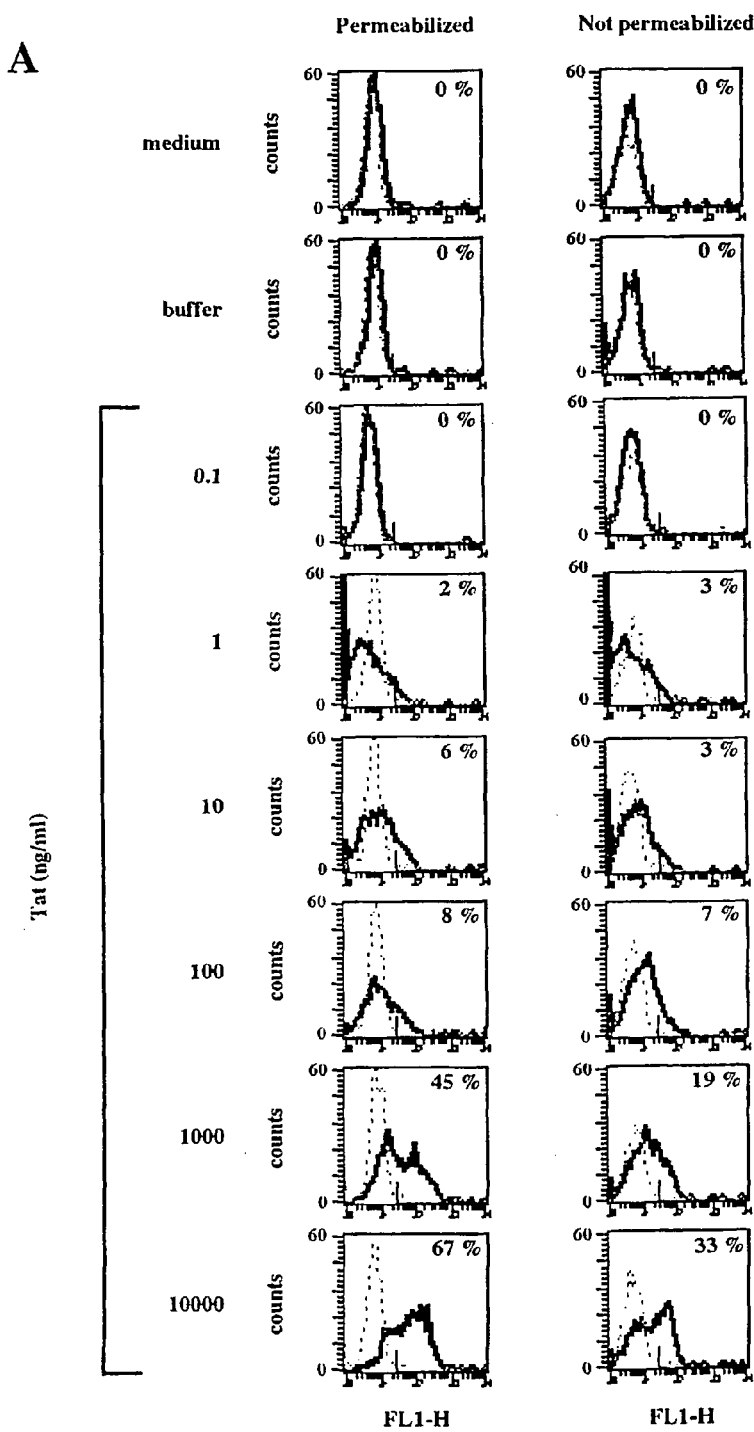
FIG. 5. Native, substantially monomeric, and biologically active Tat is efficiently taken up in a dose- and time-dependent fashion by macrophages but not by monocytes, as illustrated in FIG. 5A, FIG. 5B and FIG. 5C.
Figure 5B:
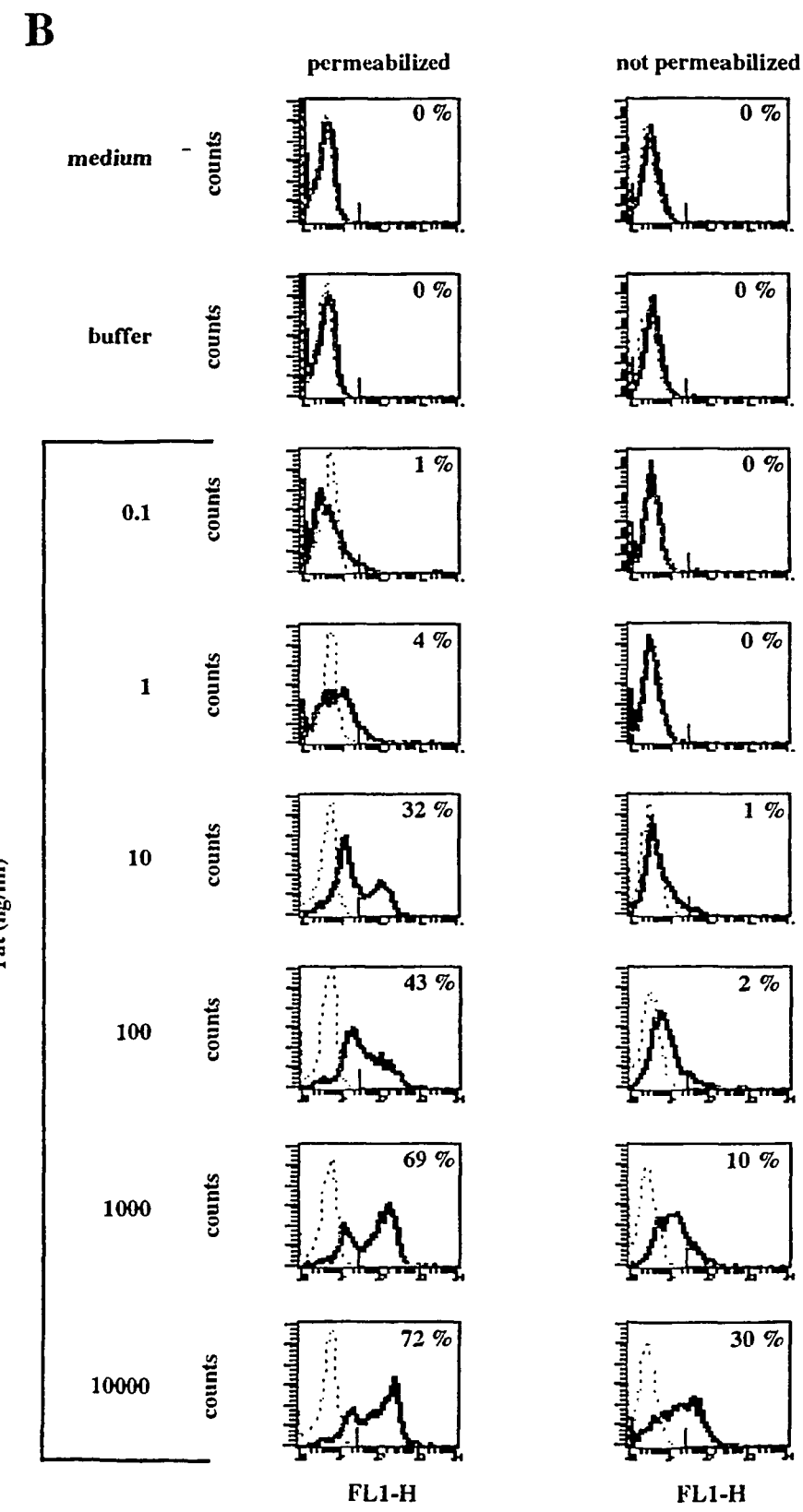
Figure 5C:
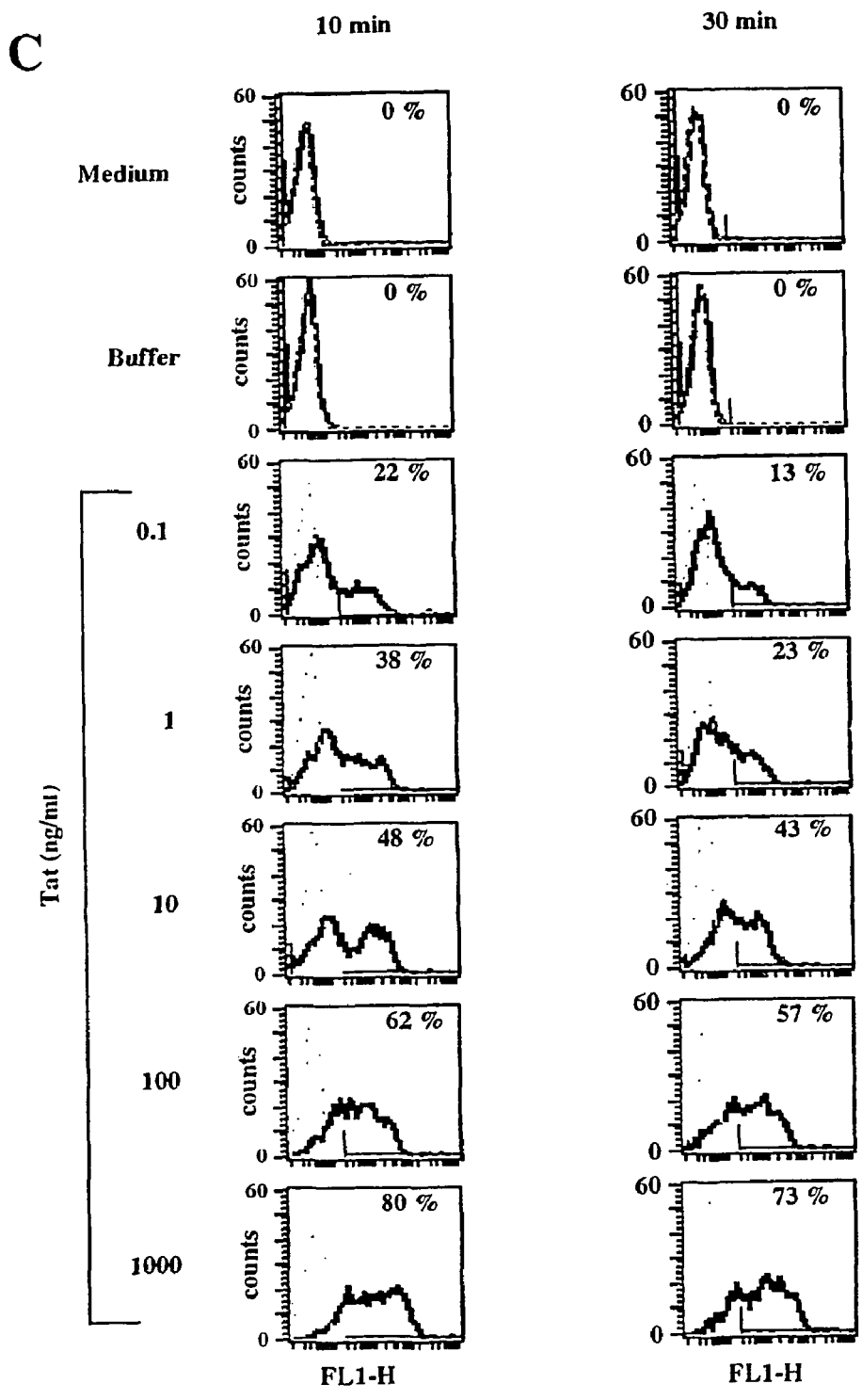

FIG. 5. Active Tat is efficiently taken up in a dose- and time dependent fashion by macrophages but not by monocytes. A, Peripheral blood monocytes, enriched from PBMC upon 2 h of adherence on plastic plate wells, were incubated with Tat at doses ranging from 0.1 to 10,000 ng/ml for 60 min at 31° C. in the dark and processed and stained as described for MDDC in FIG. 1. A, Flow cytometric analysis of cells stained with anti-Tat antibodies are shown. The percentage of positive cells (as compared to isotype stained samples) is reported into the boxes. A significant uptake of Tat is detected only at the highest doses (45% and 67% at 1000 and 10,000 ng/ml, respectively) with some levels of protein attached to the cell surface (19% and 33% at 1000 and 10,000 ng/ml on non-permeabilized cells, respectively). B, Six days-old monocyte-derived macrophages (MDM) were incubated with Tat at doses ranging from 0.1 to 10,000 ng/ml for 60 min at 37° C. in the dark and processed and stained as described for MDDC in FIG. 1. The uptake of Tat is detected in the range from 10 to 10,000 ng/ml, with a proportion of positive cells ranging from 32% to 72%, respectively. However, at the highest dose (10,000 ng/ml) a substantial amount of the Tat protein is localized at the cell surface, as demonstrated by the 30% staining of non-permeabilized MDM. C, six days-old MDDC from the same donor were incubated with Tat at doses ranging from 0.1 to 1000 ng/ml for 10 and 30 min at 37° C. in the dark and processed and stained as described in FIG. 1. The uptake of Tat is detected at all the concentrations of the protein at levels higher than those from monocytes and macrophages from the same donor (80% and 73% at the dose of 1000 ng/ml after 10 and 30 min, respectively) without any detected binding to the cell membrane.

Figure 6:
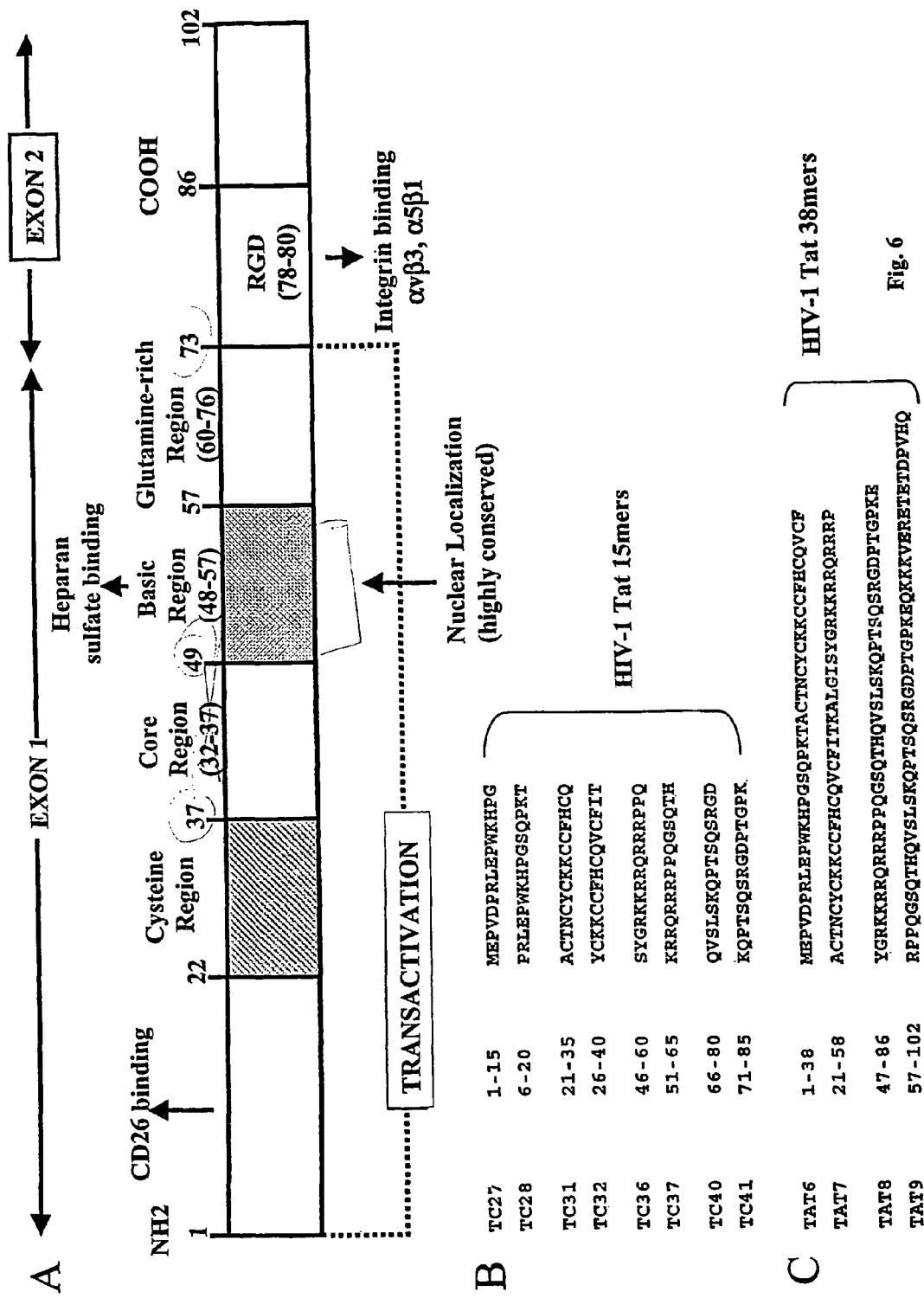
FIG. 6. Schematic representation of the HIV-1 Tat protein, functional domains thereof and sequences of the Tat peptides utilized, as illustrated in FIG. 6A, FIG. 6B and FIG. 6C.

FIG. 6. HIV-1 Tat protein, functional domains thereof and Tat peptides. Schematic representation of the HIV-1 Tat protein, both the 86 and 102 aminoacids long naturally occurring variants, with its functional domains (A) and of the sequences (based on the clade B consensus sequence) of the 15 and 38 aminoacids long peptides (indicated as 15mers and 38mers in panel B and C, respectively) utilized.

Figure 7:
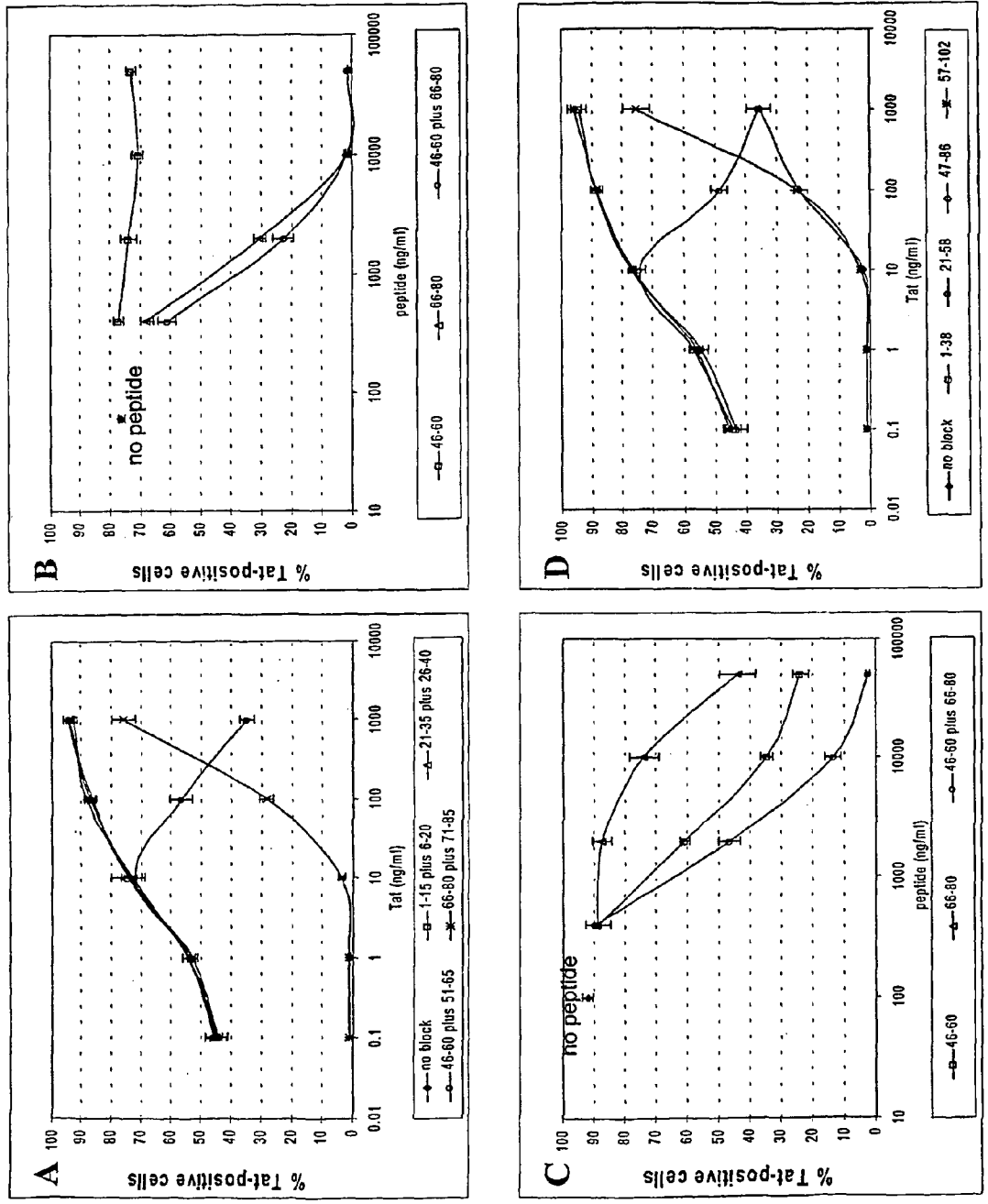
FIG. 7. Uptake of native, substantially monomeric, and biologically active Tat is differently affected by Tat peptides bearing the RGD or basic region, as illustrated in FIG. 7A, FIG. 7B, FIG. 7C and FIG. 7D.
Figure 9B:
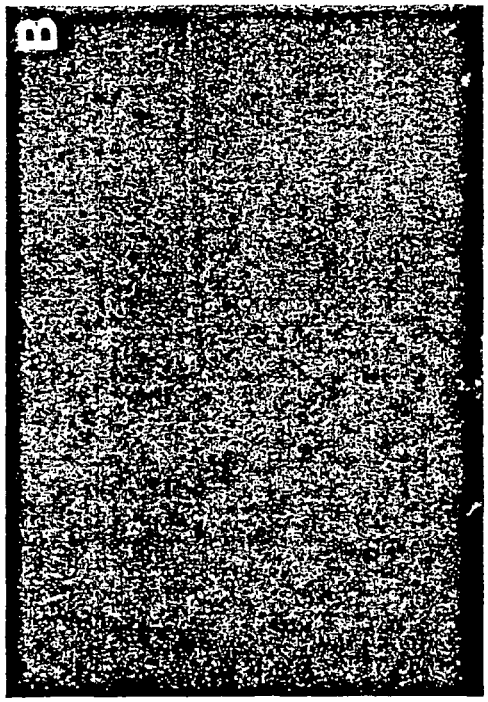
FIG. 9. Time-course of uptake of 100 ng/ml rhodaminated Tat by cytokine-activated endothelial cells, as illustrated in FIG. 9A, FIG. 9B, FIG. 9C and FIG. 9D.
Figure 9D:
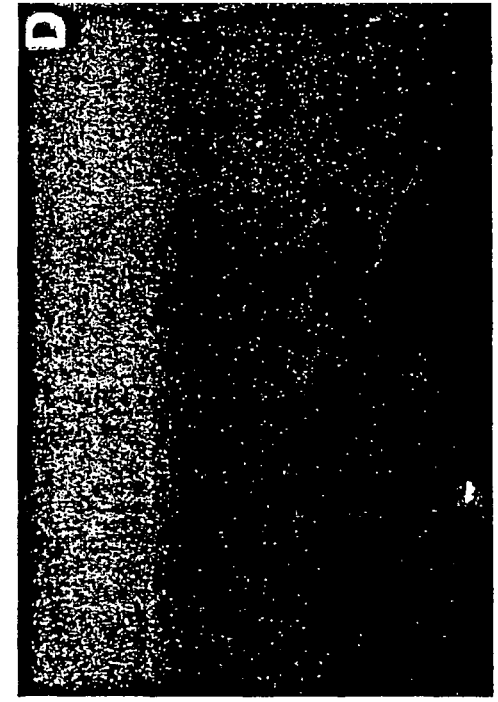
Figure 9A:
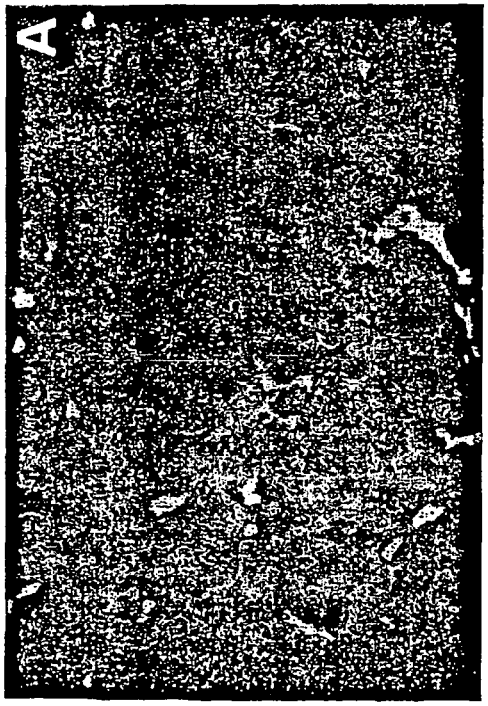
Figure 9C:
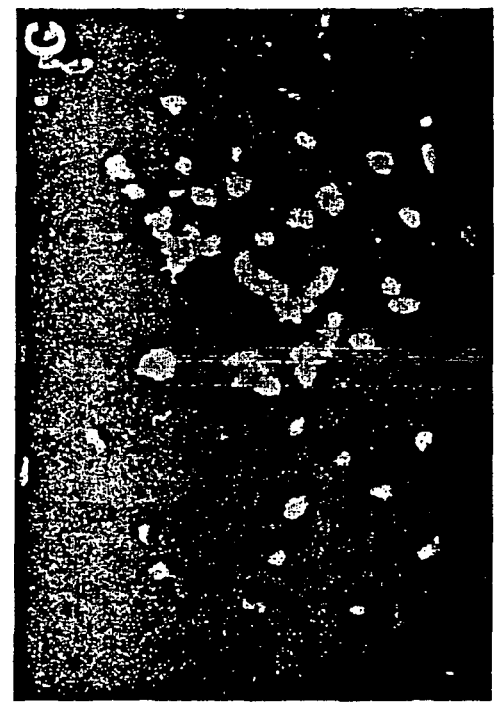
Figure 10B:
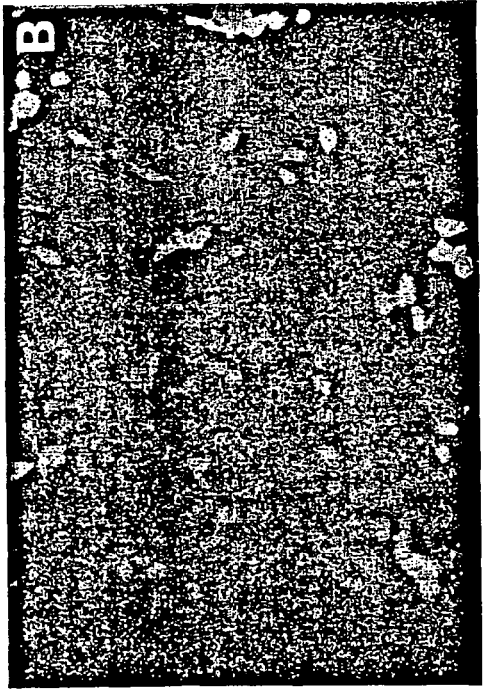
FIG. 10. Time-course of uptake of 1 µg/ml rhodaminated Tat by cytokine-activated endothelial cells, as illustrated in FIG. 10A, FIG. 10B, FIG. 10C and FIG. 10D.
Figure 10D:
Figure 10A:
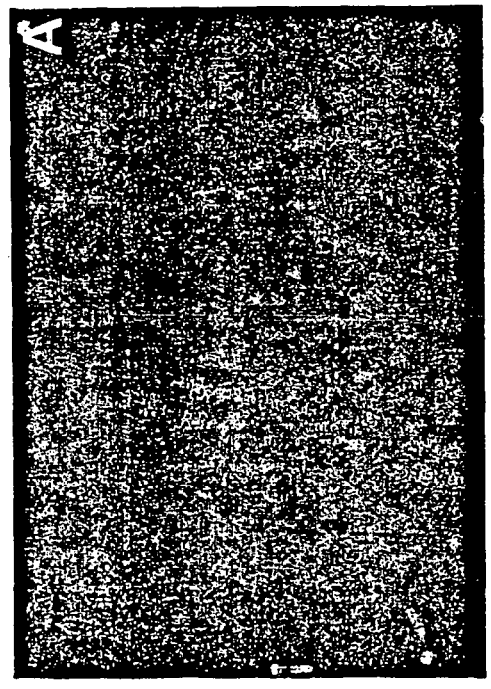
Figure 10C:

FIG. 7. Uptake of Tat is differently affected by Tat peptides bearing the RGD or basic region. A, MDDC incubated for 2 h at 4° C. in the presence of couples of 15-mer Tat peptides (as defined in FIG. 6, panel B) spanning different regions of the protein: N-terminal (1-15 (SEQ ID NO:38) plus 6-20 (SEQ ID NO:40)), cysteine rich (21-35 (SEQ ID NO:46) plus 26-40 (SEQ ID NO:48)) basic (46-60 (SEQ ID NO:56) plus 51-65 (SEQ ID NO:58)) or RGD sequence (66-80 (SEQ ID NO:64) plus 71-85 (SEQ ID NO:66)) before the addition of Tat (0.1 to 1,000 ng/ml) for 30 min at 37° C. B and C, MDDC were pre-treated with the 15-mer Tat peptides 46-60 and 66-80, alone or combined at doses ranging from 400 to 50,000 ng/ml, before the addition of Tat at 10 (B) or 1000 ng/ml (C) for 10 min at 37° C. D, MDDC were incubated for 2 h at 4° C. in the presence of 38 146-mer Tat peptides (1-38 (SEQ ID NO:103), 21-58 (SEQ ID NO:104), 47-86 (SEQ ID NO:105), 57-102 (SEQ ID NO:106)) covering different regions of the protein (as defined in FIG. 6, panel C), before the addition of Tat protein (0.1 to 1,000 ng/ml) for 10 min at 37° C. In all the cases the intracellular staining for Tat was then performed as reported above. Data are expressed as the means (and SEM) of the percentages of Tat-positive cells from three different donors.

FIG. 8. Rhodaminated active Tat is taken up in a dose-dependent fashion by cytokine-activated endothelial cells. Human umbilical vein endothelial cells (HUVEC) were activated by culturing them for 5-6 days in the presence of conditioned media from CD4+ cells transformed by the human T-lymphotropic virus type-II (HTLV-II) or stimulated with PHA, as described previously (Ensoli 1990; Barillari 1992 and 1993; Fiorelli 1999). These conditioned media contain the same inflammatory cytokines (IC) including IL-1, TNF and interferon γ (IFNγ), which activate endothelial cells during inflammation or reparative processes. In particular, IL-1, TNF and/or IFNγ induce in endothelial cells the expression of the integrin receptors α5β1 and αvβ3 (Barillari 1993; Fiorelli 1999).

After 5-6 days of culture, HUVEC were suspended by trypsinization, washed with trypsin inhibitors, plated on 8 well chamber slides (Nunc Inc. Naperville, Ill.) at $5 \times 10^4$ cells/well and cultured in RPMI medium (Life Technologies, Eragny, France) containing 15% FBS, in the absence of conditioned media, for 18 hrs. After that time, cells were washed with serum free RPMI and then cultured at 37° C. in a $CO_2$ incubator for 15' in serum-free RPMI containing serial dilutions of biologically active Tat protein which was rhodaminated at lysine residues essentially as described (Mann 1991). Briefly, 50 µg recombinant Tat (2 mg/ml), was brought to pH 9.0 by the addition of 2.5 µl of 1 M $Na_2CO_3$. Then, 2.5 µl of 1 mg/ml tetramethylrhodamine isothiocyanate (TRITC, Chemical Co., St. Louis, Mo.) in dimethylsulfoxide (DMSO) was added and the reaction allowed to proceed for 8 h at 4° C. Unreacted TRITC was quenched by the addition of 2.5 µl of 0.5 M $NH_4Cl$, the pH was lowered to 7.0, using 1 M HCl, and the rhodaminated Tat was dialyzed against two changes of 50 nM Tris-HCl, pH 7.0, 1 mM dithiothreitol (DTT) to remove the quenched TRITC. BSA or PBS, rhodaminated in the same way, were used as negative controls. Rhodaminated Tat was tested for KS cells growth activity as described (Ensoli, 1990) to ensure that the biological activity was maintained. Tat resuspension buffer (PBS-0.1% BSA) was rhodaminated in the same way and employed as negative control. HUVEC were then fixed in ice-cold acetone-methanol (1:1). The uptake and the intracellular distribution of Tat were observed and photographed using a fluorescence microscopy. Results were evaluated by comparing the fluorescence of sample with the negative control and scored from—(negative) to ++++ (highly positive) on the amount of uptake without prior knowledge of sample code.

Incubation were with: buffer (PBS-0.1% BSA), panel A; Tat 10 ng/ml, panel B; Tat 100 ng/m (, panel C; Tat 1 µg/ml, panel D.

FIG. 9. Time-course analysis of uptake of 100 ng/ml rhodaminated active Tat by cytokine-activated endothelial cells. HUVEC were activated and plated on 8-well chamber slides as described in the legend to FIG. 8. Cells were then exposed to 100 ng/ml of rhodaminated Tat for the periods of time indicated below.

BSA (fraction V, Sigma) was rhodaminated in the same way as for Tat and employed as negative control. Incubations were with: Tat 100 ng/ml, 15' exposure, panel A; BSA, 15' exposure, panel B; Tat 100 ng/ml, 60' exposure, panel C; BSA, 60' exposure, panel D.

FIG. 10. Time-course analysis of uptake of 1 µg/ml rhodaminated active Tat by cytokine-activated endothelial cells. Cytokine-activated HUVEC were treated as described in FIG. 8, then incubated with 1 µg/ml rhodaminated Tat for 15 minutes, panel A; 30 minutes, panel B; 60 minutes, panel C; 120 minutes, panel D.

Figure 11:
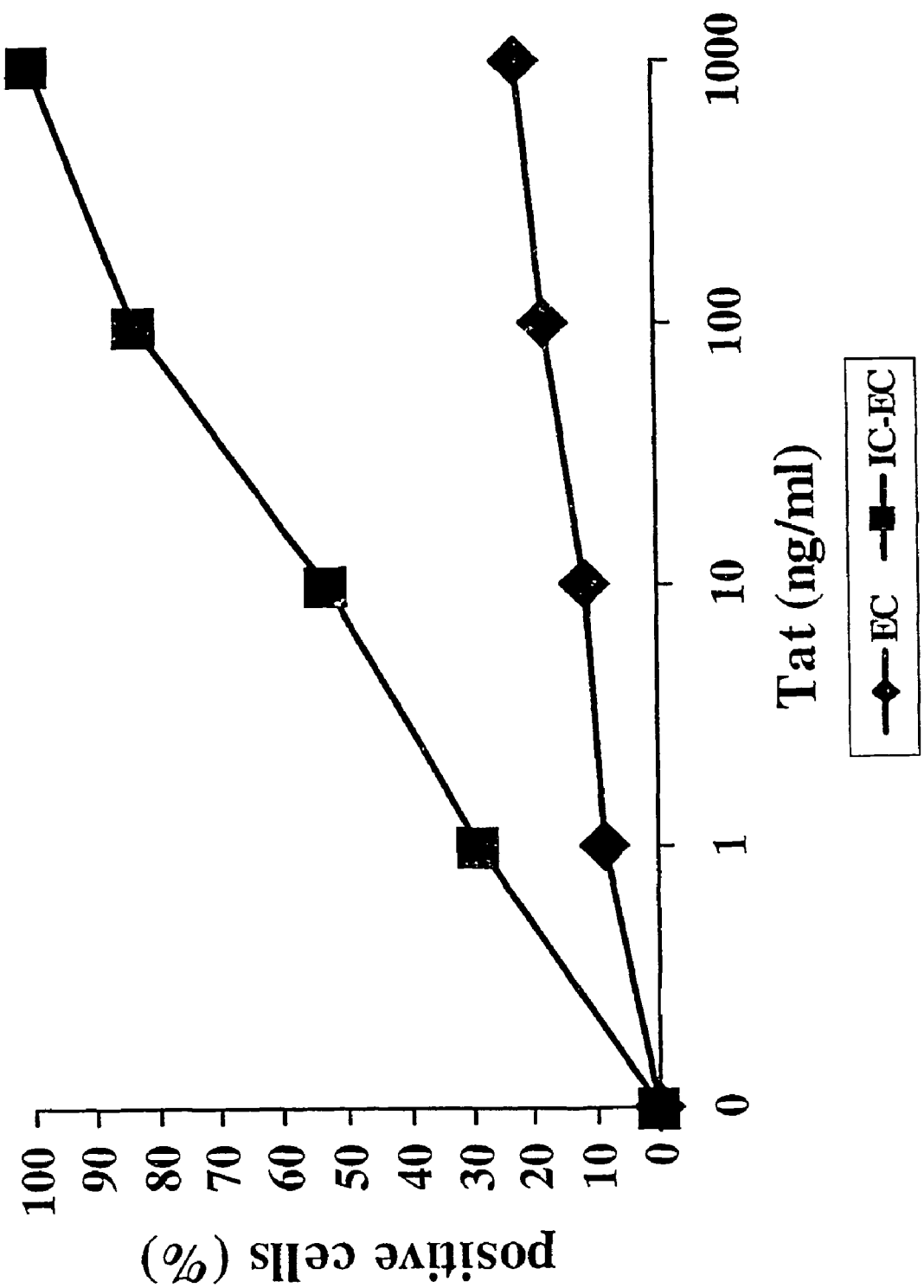
FIG. 11. Dose-response analysis of uptake of native, substantially monomeric, and biologically active Tat protein by cytokine-activated endothelial cells versus non activated cells.

FIG. 11. Dose-response analysis of uptake of active Tat protein by cytokine-activated endothelial cells versus non activated cells. HUVEC ($7 \times 10^4$ cells/well in 6-well gelatinized plates) were grown in complete medium as described above (legend to FIG. 8) and incubated for 5 days in the presence (IC-EC) or in the absence (EC) of combined recombinant inflammatory cytokines (IFNγ 10 U/ml, IL-1β 5 ng/ml, TNF-a 2 ng/ml). Cells were then washed twice and incubated in 1 ml of RPMI 1640 containing 15% FCS in the presence or absence of serial dilutions of active Tat protein (0.01 to 1000 ng/ml) or Tat dilution buffer (PBS containing 0.1% BSA) for 10' at 37° C. in the dark. Cells were then washed with cold RPMI 1640, trypsinized, fixed for 10' at 4° C. with FACS lysing solution (Becton Dickinson), exposed for 30' at 4° C. to permeabilizing solution (Becton Dickinson), stained with rabbit anti-Tat antibodies or rabbit IgG control antibodies and analyzed by FACS, as described for MDDC (legend to FIG. 1). Uptake of native Tat is increased in cytokine-activated cells as compared to non-activated cells. The percentage of positive cells after 10' incubation with increasing concentration of native Tat protein in a representative experiment out of 3 performed is shown.

Figure 12:
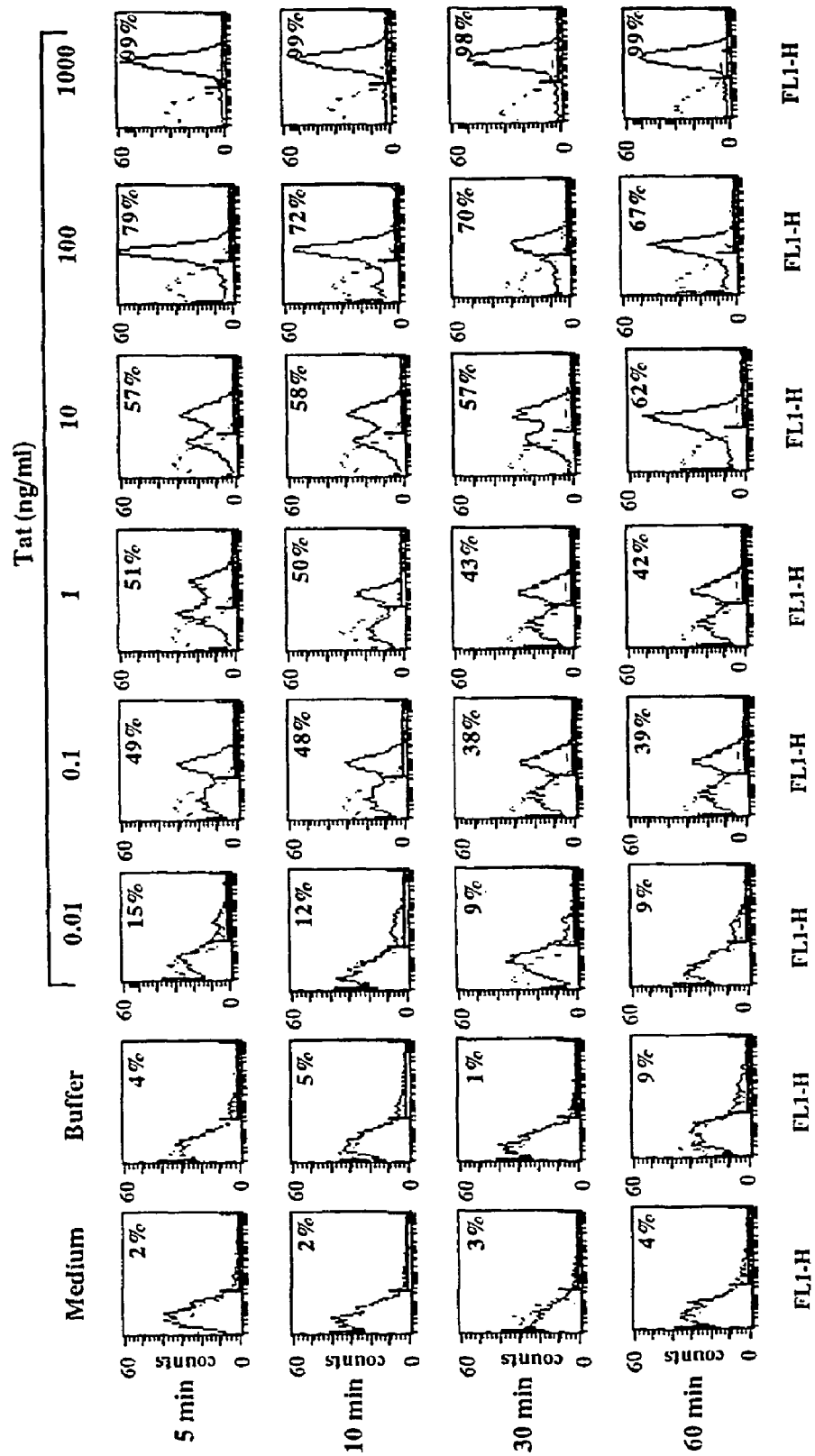
FIG. 12. Dose- and time-course analysis of uptake of native, substantially monomeric, and biologically active Tat by cytokine-activated endothelial cells.

FIG. 12. Dose- and time-course analysis of uptake of active Tat by cytokine-activated endothelial cells. Cells were activated and uptake experiments performed as described in FIG. 11. Incubation were for 5', 10', 30' or 60'. In addition, to demonstrate the specific intracytoplasmatic localization of the protein, staining with anti-Tat antibodies was also performed with non-permeabilized HUVEC. Uptake of native Tat by activated endothelial cells is time- and dose-dependent, and is already detected at concentrations as low as 0.01 ng/ml. The percentage of positive cells (as compared to isotype antibodies stained samples) is reported into the boxes. Data are from one representative experiment out of 4 performed.

Figure 13A:
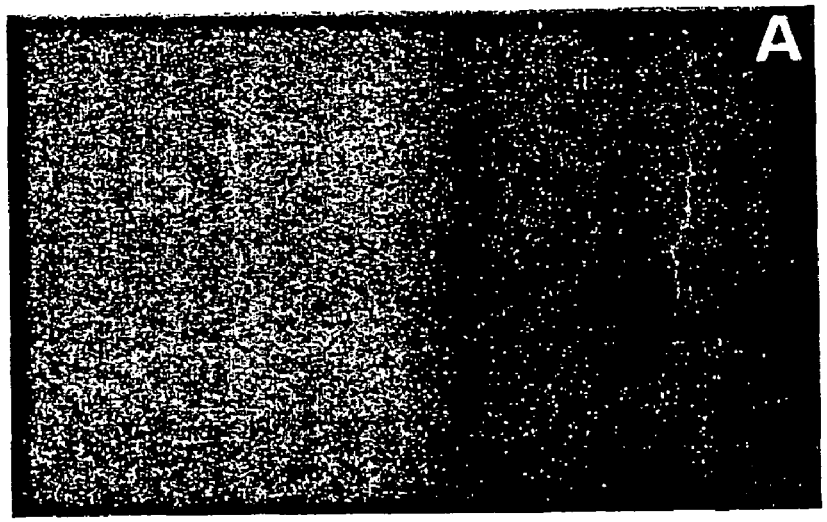
FIG. 13. Inhibition of uptake of 10 ng/ml rhodaminated Tat by cytokine-activated endothelial cells with unlabelled Tat protein, as illustrated in FIG. 13A, FIG. 13B and FIG. 13C.
Figure 13B:
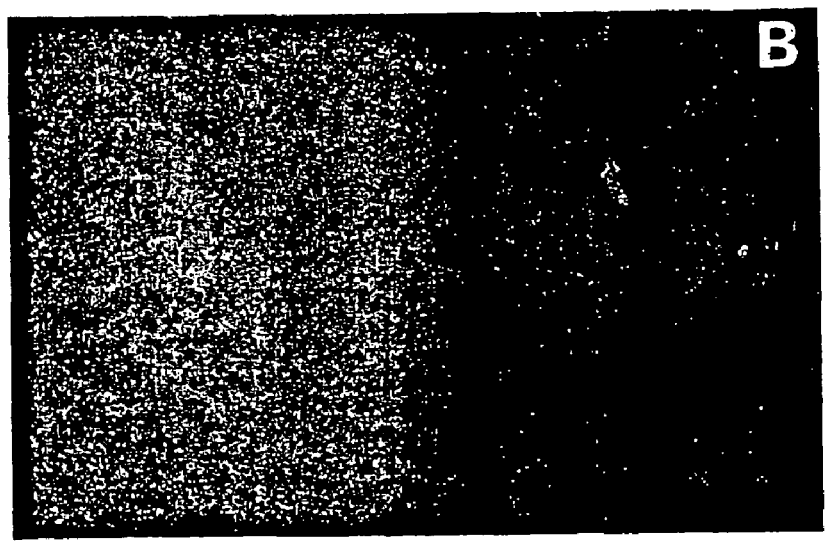
Figure 13C:
Figure 14A:
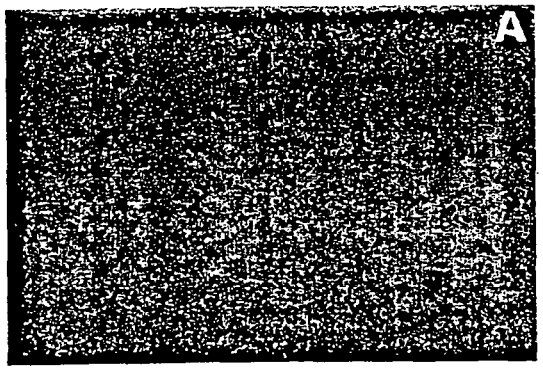
FIG. 14. Inhibition of uptake of 10 ng/ml rhodaminated Tat by cytokine-activated endothelial cells with antibodies to α5β1 and αvβ3-integrin receptors, as illustrated in FIG. 14A, FIG. 14B, FIG. 14C, FIG. 14D and FIG. 14E.
Figure 14B:
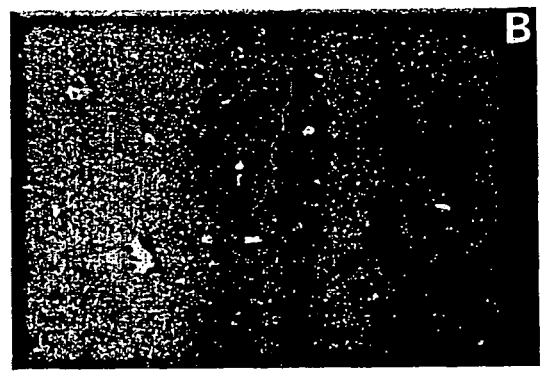
Figure 14C:
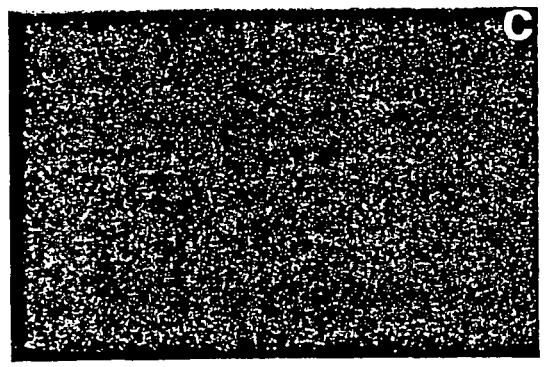
Figure 14D:
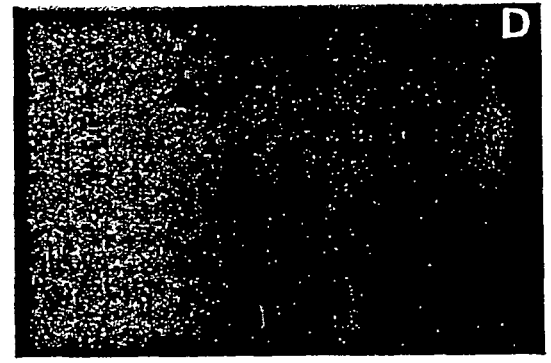
Figure 14E:
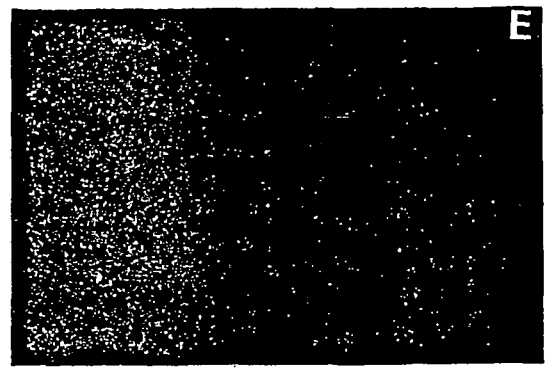
Figure 15A:
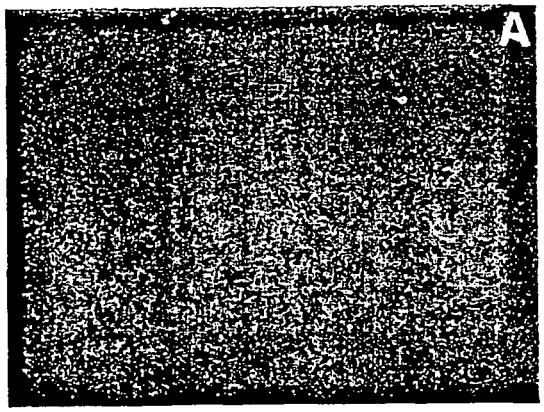
FIG. 15. Inhibition of uptake of 100 ng/ml rhodaminated Tat by cytokine-activated endothelial cells with antibodies to α5β1 and αvβ3 integrin receptors, as illustrated in FIG. 15A, FIG. 15B, FIG. 15C, FIG. 15D and FIG. 15E.
Figure 15B:
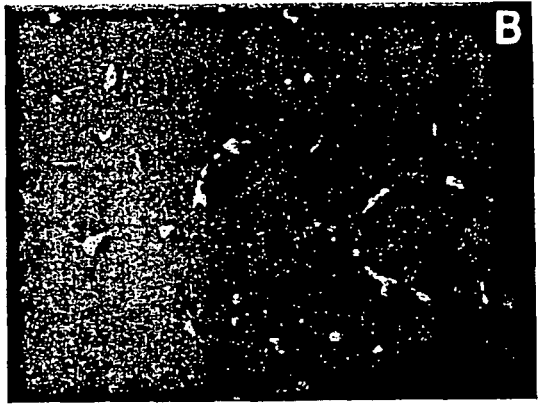
Figure 15C:
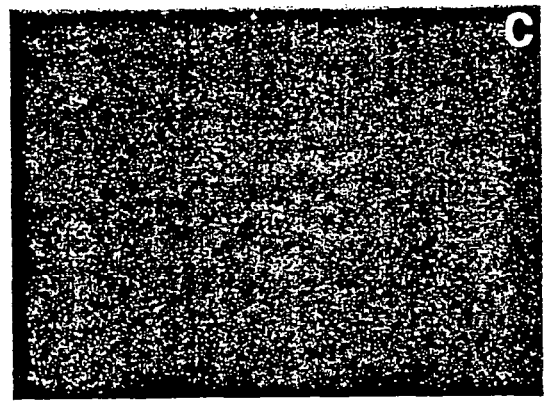
Figure 15D:
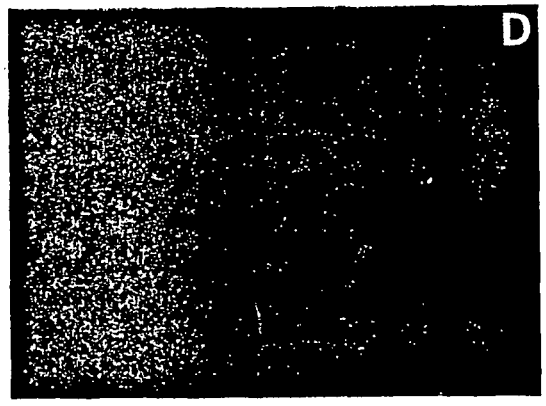
Figure 15E:
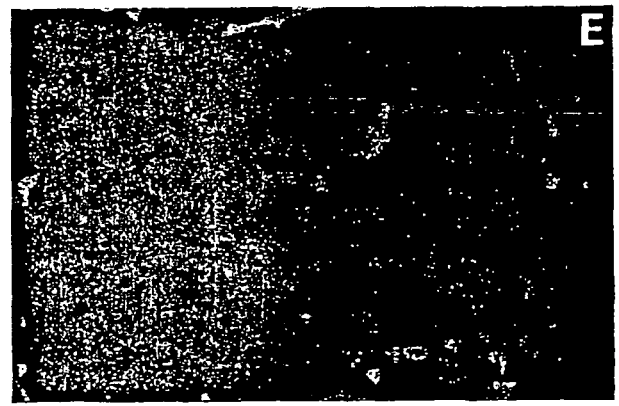
Figure 16B:
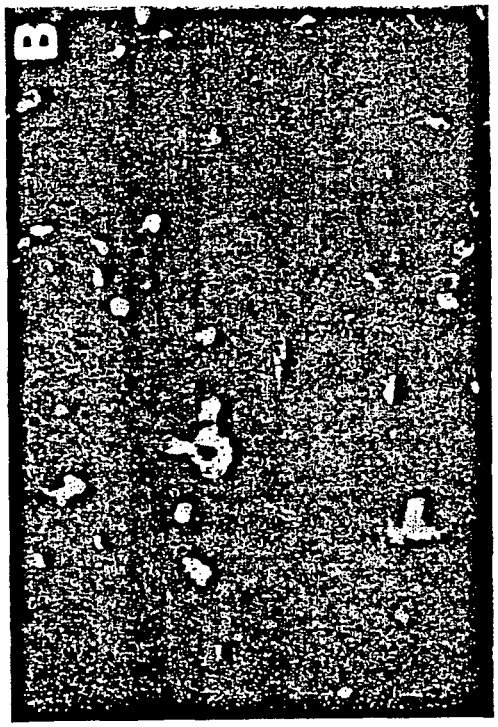
FIG. 16. Uptake of 1 µg/ml rhodaminated Tat is partially inhibited by anti-α5β1 and anti-αvβ3 antibodies when cells are incubated with Tat for 15 minutes, as illustrated in FIG. 16A, FIG. 16B, FIG. 16C and FIG. 16D.
Figure 16D:
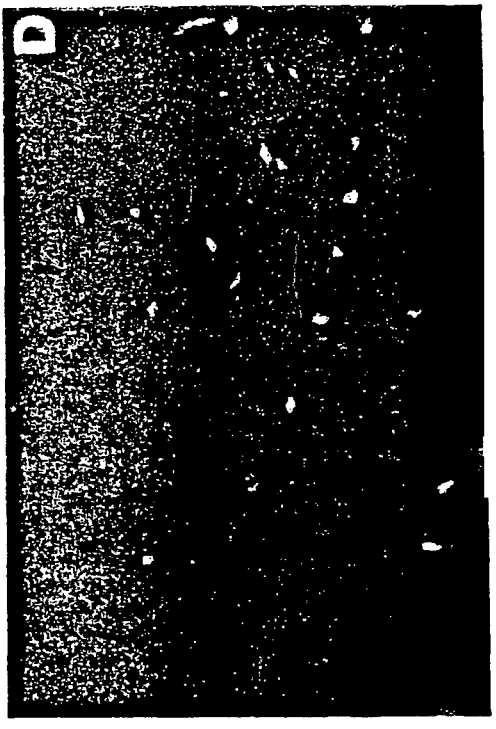
Figure 16A:
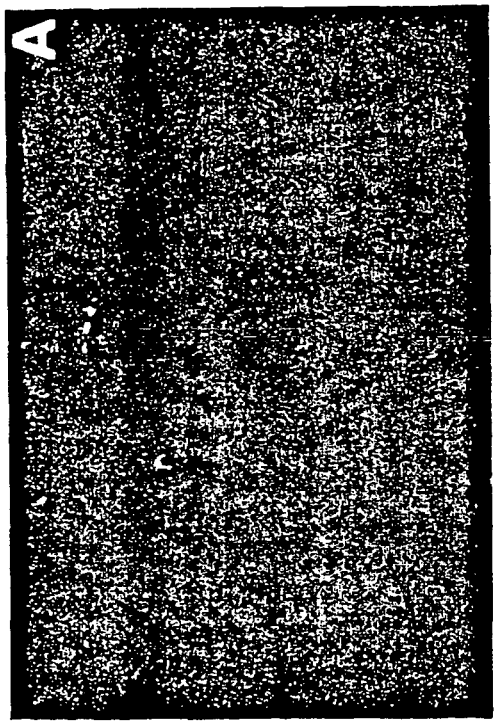
Figure 16C:
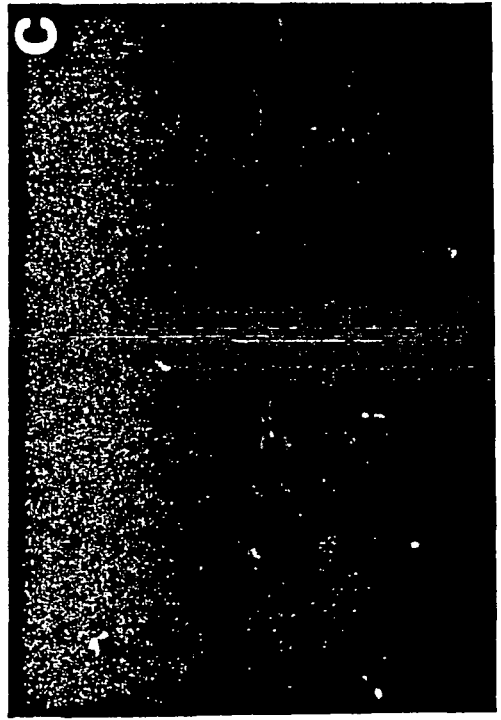

FIG. 13. Inhibition of uptake of 10 ng/ml rhodaminated active Tat by cytokine-activated endothelial cells with unlabelled Tat protein. Cytokine-activated HUVEC were treated as described in FIG. 8, preincubated in serum free medium, containing buffer or 1 µg/ml unlabelled Tat, and then incubated for 15 minutes at 37° C. with 10 ng/ml rhodaminated Tat or rhodaminated BSA.

Panel A, preincubated with buffer, incubated with BSA.
Panel B, preincubated with buffer, incubated with Tat.
Panel C, preincubated with 1 µg/ml unlabelled Tat, incubated with Tat.

FIG. 14. Inhibition of uptake of 10 ng/ml rhodaminated active Tat by cytokine-activated endothelial cells with anti-α5β1 and anti-αvβ3 antibodies. HUVEC were activated with conditioned media from PHA-stimulated or HTLV II-transformed T cells (IC-HUVEC) and seeded onto 8 well chamber slides as described in the legend to FIG. 8. IC-HUVEC were then incubated in serum free medium on a rotating device for 2 h at 4° C. with monoclonal antibodies directed against the a chain of the α5β1 receptor (anti-CD49wE, Chemicon Inc. Temecula, Calif.) and P chain of the α5β1 receptor receptor (anti-CD29, Chemicon), or the a chain of the αvβ3 receptor (anti-CD51, Chemicon), and β chain of the αvβ3 receptor (anti-CD61, Chemicon). Monoclonal antibodies directed against the endothelial cell marker factor Vil related antigen (anti-FVIIIRA, Chemicon) were employed as control of specificity. All antibodies were employed at 5 µg/ml. Antibody dilution buffer (PBS containing 0.1% BSA) was employed as a negative control. After preincubation with antibodies, 10 ng/ml of rhodaminated Tat was added to the cells. Rhodaminated BSA was employed as negative control. IC-HUVEC were kept for 15' at 37° C. in a $CO_2$ incubator and then fixed in ice-cold acetone-methanol (1:1). The uptake and the intracellular distribution of Tat were-observed and photographed using fluorescence microscopy. Results were evaluated by comparing the fluorescence of sample with the negative control and scored from—(negative) to ++++ (highly positive) on the amount of uptake without prior knowledge of sample code.

Panel A, preincubated with buffer, incubated with BSA.
Panels B, preincubated with buffer, incubated with Tat.
Panel C, preincubated with anti-α5 and anti-β1 monoclonal antibodies, incubated with Tat.
Panel D, preincubated with anti-αv and anti-β3 monoclonal antibodies, incubated 1:5 with Tat.
Panel E, preincubated with anti-human factor VIII antibodies (control antibodies), incubated with Tat.

FIG. 15. Inhibition of uptake of 100 ng/ml rhodaminated active Tat by cytokine-activated endothelial cells with anti-α5β1 and anti-αvβ3 antibodies. IC-HUVEC were treated as described in FIG. 8, then preincubated in serum free medium, containing buffer or antibodies, then incubated for 15 minutes at 37° C. with 100 ng/ml rhodaminated Tat or rhodaminated BSA.

Panel A, preincubated with buffer, incubated with BSA.
Panel B, preincubated with buffer, incubated with Tat.
Panel C, preincubated with monoclonal antibodies against the α and β chains of the α5β1 integrin and incubated with Tat.
Panel D, preincubated with monoclonal antibodies against the a and 1 chains of the αvβ3 integrin and incubated with Tat.
Panel E, preincubated with anti-human factor VIII antibodies (control antibodies), incubated with Tat.

FIG. 16. Uptake of 1 µg/ml rhodaminated active Tat is partially inhibited by anti-α5β1 and anti-αvβ3 antibodies when cells are incubated with Tat for 15 minutes. HUVEC were activated as described in FIG. 8, preincubated with anti-α5 and anti-β1 or anti-αv and anti-β3 monoclonal antibodies, or buffer, and then incubated with 1 µg/ml rhodaminated Tat or rhodaminated BSA for 15 minutes at 37° C.

Panel A, preincubated with buffer, incubated with BSA.
Panel B, preincubated with buffer, incubated with Tat.
Panel C, preincubated with anti-α5 and anti-β1 monoclonal antibodies, incubated with Tat.
Panel D, preincubated with anti-αv and anti-β3 monoclonal antibodies, incubated with Tat.

FIG. 16. Uptake of 1 µg/ml rhodaminated active Tat is not inhibited by anti-integrin antibodies when cells are incubated with Tat for 60 minutes. HUVEC were activated as described in FIG. 8, preincubated with anti-α5 and anti-β1 or anti-αv and anti-β3 monoclonal antibodies, or buffer, and then incubated with 1 µg/1 ml rhodaminated Tat for 60 minutes at 37° C.

Panel A, preincubated with buffer, incubated with Tat.
Panel B, preincubated with anti-α5 and anti-β1 monoclonal antibodies, incubated with Tat.
Panel C, preincubated with anti-αv and anti-β3 monoclonal antibodies, incubated with Tat.

FIG. 18. Active Tat enhances the production of the cytokines IL-12 and TNF-α, and of the β-chemokines MIP-1α, MIP-1β and RANTES by MDDC. MDDC from 8 donors were cultured at the density of $2 \times 10^5$ per ml for 18 h in complete medium in the absence or presence of serial concentrations (20 to 20,000 ng/ml) of native or oxidized Tat. Tat reconstitution buffer was employed as negative control. LPS from E. coli, serotype 055: B5 (10 µg/ml, Sigma-Aldrich, Milano, Italy) was used as the positive control. After 18 h the cell supernatants were collected and assayed for the presence of TNF-α, IL-12, RANTES, MIP-1α and MIP-1β with commercially available kits according to the manufacturer's instructions (Cytoscreen TNF-alpha and IL-12 ELISA kits, Biosource Europe, Nivelle, Belgium; Quantikine RANTES, MIP-1α and MIP-1β R&D Systems Europe, Abingdon, UK). Grey, empty and black symbols represent values from cells treated with Tat, buffer or LPS, respectively. Data are reported as the mean values (±SEM) from the eight different donors and are expressed in pg/ml. A very poor cytokine or β-chemokine production was induced by oxidized-inactivated Tat protein.

Figure 19:
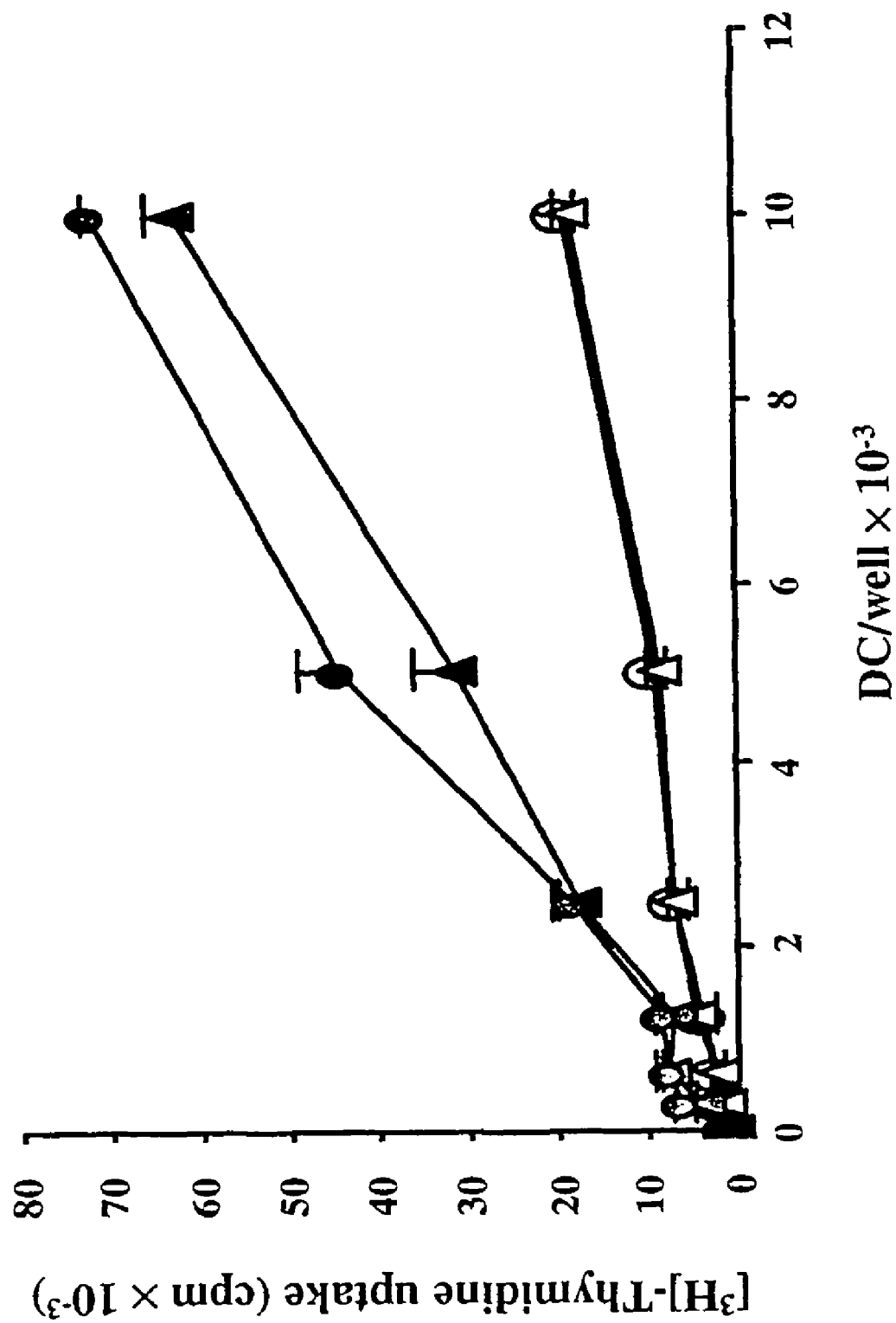
FIG. 19. Native, substantially monomeric, and biologically active Tat enhances allogeneic antigen presentation by MDDC.

FIG. 19. Active Tat enhances allogeneic antigen presentation by MDDC. MDDC ($2 \times 10^5$ cells/ml) were incubated for 18 h with LPS (positive control) (filled circles), active Tat protein (10 µg/ml) (filled triangles), reconstitution buffer (empty triangles) or culture medium (empty circles). Then, they were washed and cultured in medium (containing 5% FBS) in 96 wells plates together with monocyte-depleted allogeneic PBL ($2 \times 10^5$/well) at ratios ranging from 1:10 to 1:640. To evaluate lymphocyte proliferation, after 6 days $^3$[H]-thymidine was added to the wells for an additional 16 h and samples harvested onto glass fibre filters (Printed Filtermat A, Wallac, Turku, Finland), counted with a Betaplate (Wallac) and the values expressed in cpm. Data are from a representative experiment and have been reproduced with 3 other donors. Means and SEM are reported.

Figure 20A:
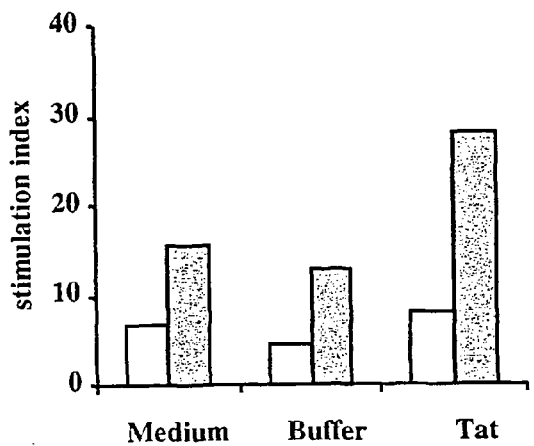
FIG. 20. Native, substantially monomeric, and biologically active Tat increases tetanus toxoid (TT)-specific presentation by MDDC to primed PBL enhancing specific T cell responses, as illustrated in FIG. 20A, FIG. 20B and FIG. 20C.
Figure 20B:
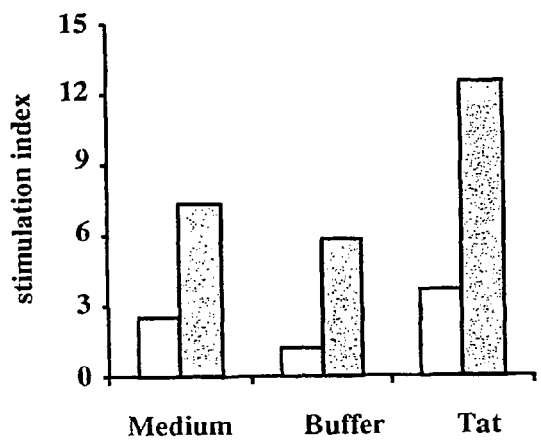
Figure 20C:
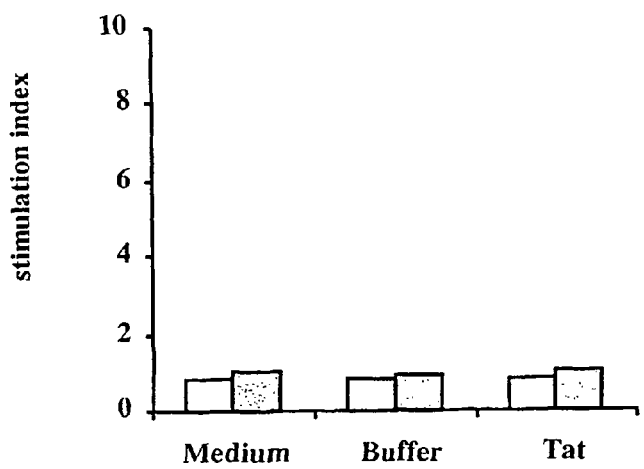

FIG. 20. Active Tat increases TT-specific presentation by MDDC to primed PBL enhancing specific T cell responses. MDDC ($2 \times 10^5$ cells/ml) from 3 healthy donors, two responsive (B16 and B42) and one unresponsive (B45) to TT in proliferation assays, were incubated for 18 h with active Tat protein (10 µg/ml), reconstitution buffer or culture medium, and then cultured in complete medium (containing 5% FBS), together with autologous PBL (2×10⁵/well) at a ratio of 1:20 in the absence (empty columns) or in the presence (grey columns) of 5 µg/ml TT (Connaught, Willowdale, Canada). To evaluate lymphocyte proliferation, after 6 days $^3$[H]-thymidine was added for an additional 16 h, samples harvested and cpm counted as reported above. Data are represented as stimulation indexes (S.I.) that indicates the ratios between counts from DC-PBL co-cultures versus those from PBL alone.

FIG. 21. Prime-boost vaccine protocol to evaluate the adjuvant activity of biologically active Tat protein. Two groups of Balb/c mice were utilized. The first group (arm 1) was immunized twice intradermally with Gag alone (priming) and subsequently twice intranasally with Gag associated to the mucosal adjuvant Malp-2 (boosting). The second group (arm 2) was immunized twice intradermally with Gag and Tat mixed together (priming) and subsequently twice intranasally with Gag mixed with Tat and associated to the mucosal adjuvant Malp-2 (boosting). The vaccinations were performed at the time indicated.

Figure 22:
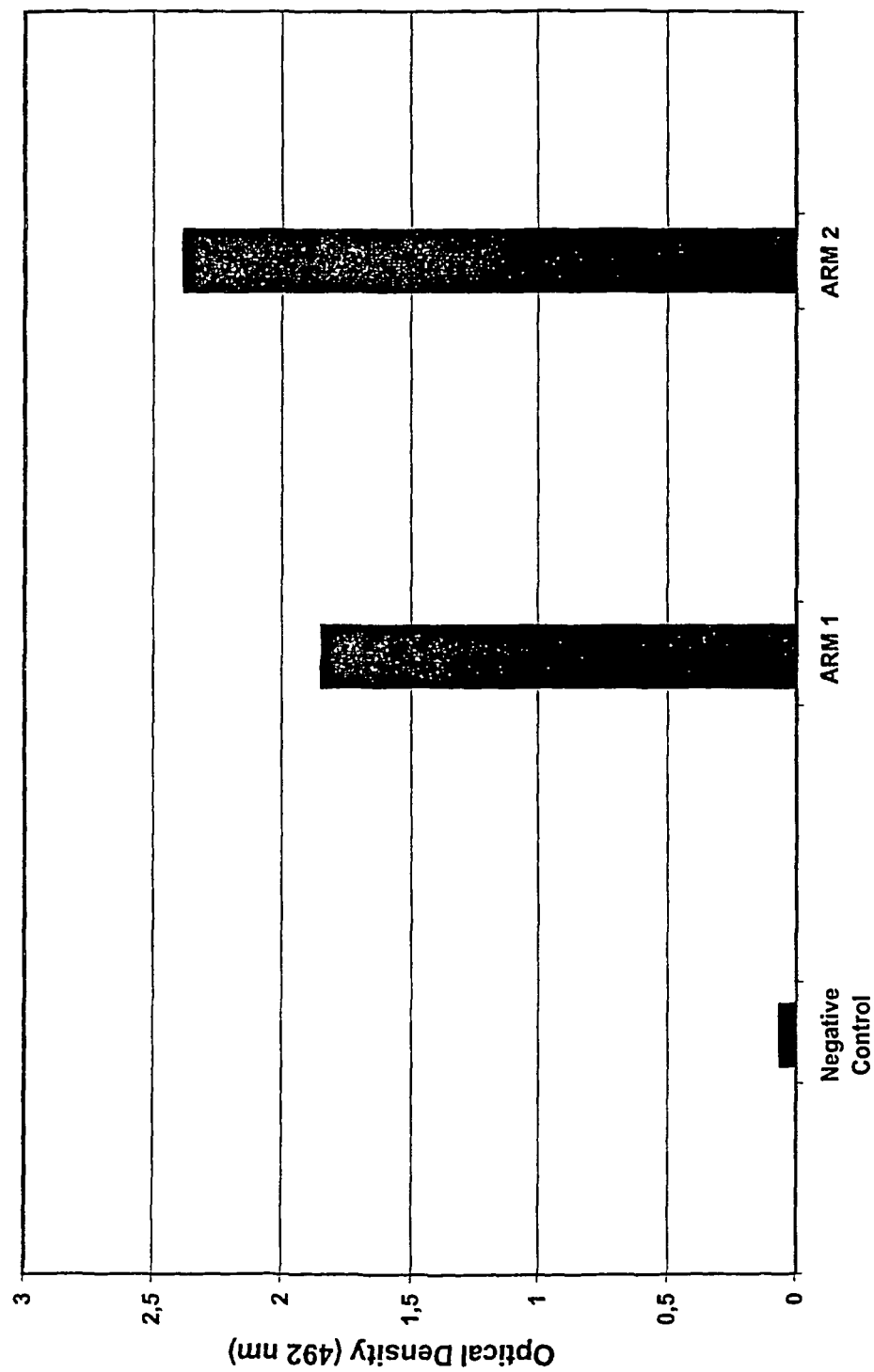
FIG. 22. Vaccination of mice with Gag and Tat induces higher antibody response against Gag, as compared to mice vaccinated with gag alone.

FIG. 22. Antibody response against Gag. Anti-Gag antibodies were measured in the serum from mice of both arms by a commercial Elisa (ELAVIA AB HIV2, BIO-RAD Laboratories Sri, MI, Italy) according to the manufacturer's instructions.

The sera were diluted 1:100 before testing. The cut-off value was an optical density of 0.3.

Figure 23:
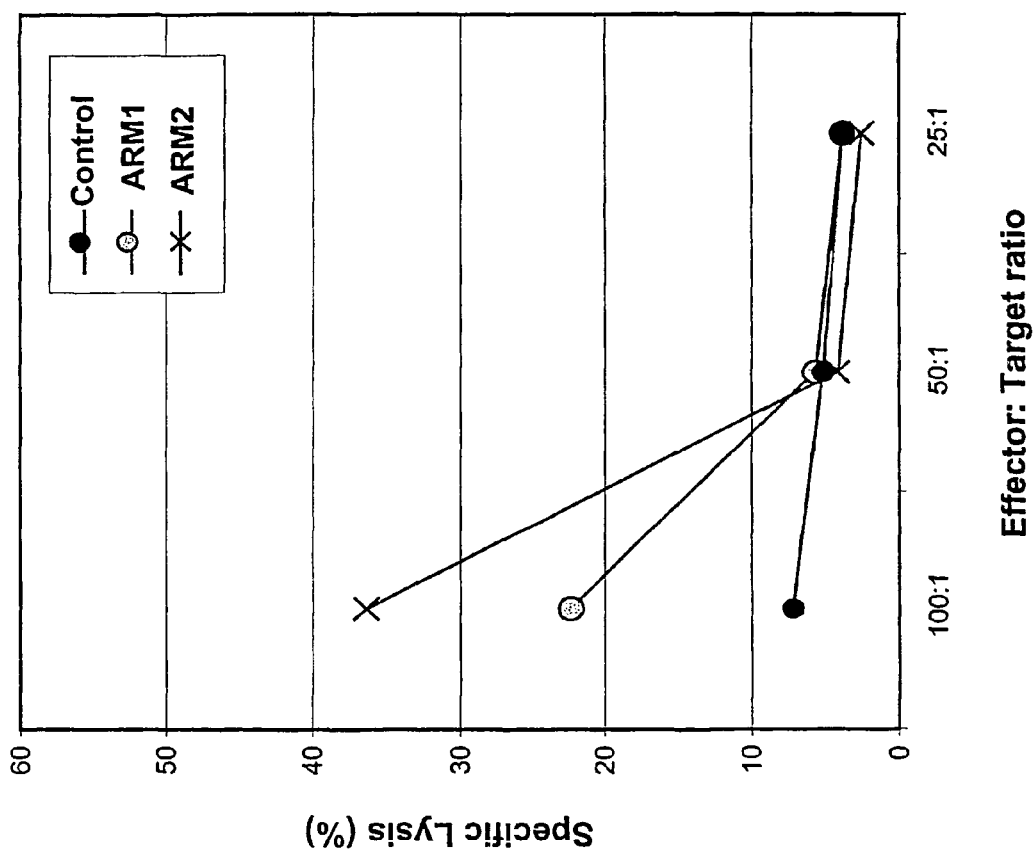
FIG. 23. Vaccination of mice with Gag and Tat induces higher anti-Gag cytolytic activity, as compared to mice vaccinated with gag alone.

FIG. 23. Anti-Gag cytolytic activity. Splenocytes from mice from both arms were stimulated in vitro with Gag peptides for 6 days in the presence of IL-2 (Effectors) and thereafter incubated with p815 cells pulsed with Gag peptides and labeled with $^{51}$Cr (Targets), at the indicated ratios. The specific lysis was determined according to standard methodology. The spontaneous $^{51}$Cr release did not exceed 10% of the maximum release. A specific $^{51}$Cr release above 10% was considered positive.

The following examples are given to better illustrate the invention and are not to be considered as limiting the scope thereof.

EXAMPLE 1

Active Tat is Efficiently Taken Up by MDDC But Not by TCB and BLCL

Figure 1B:
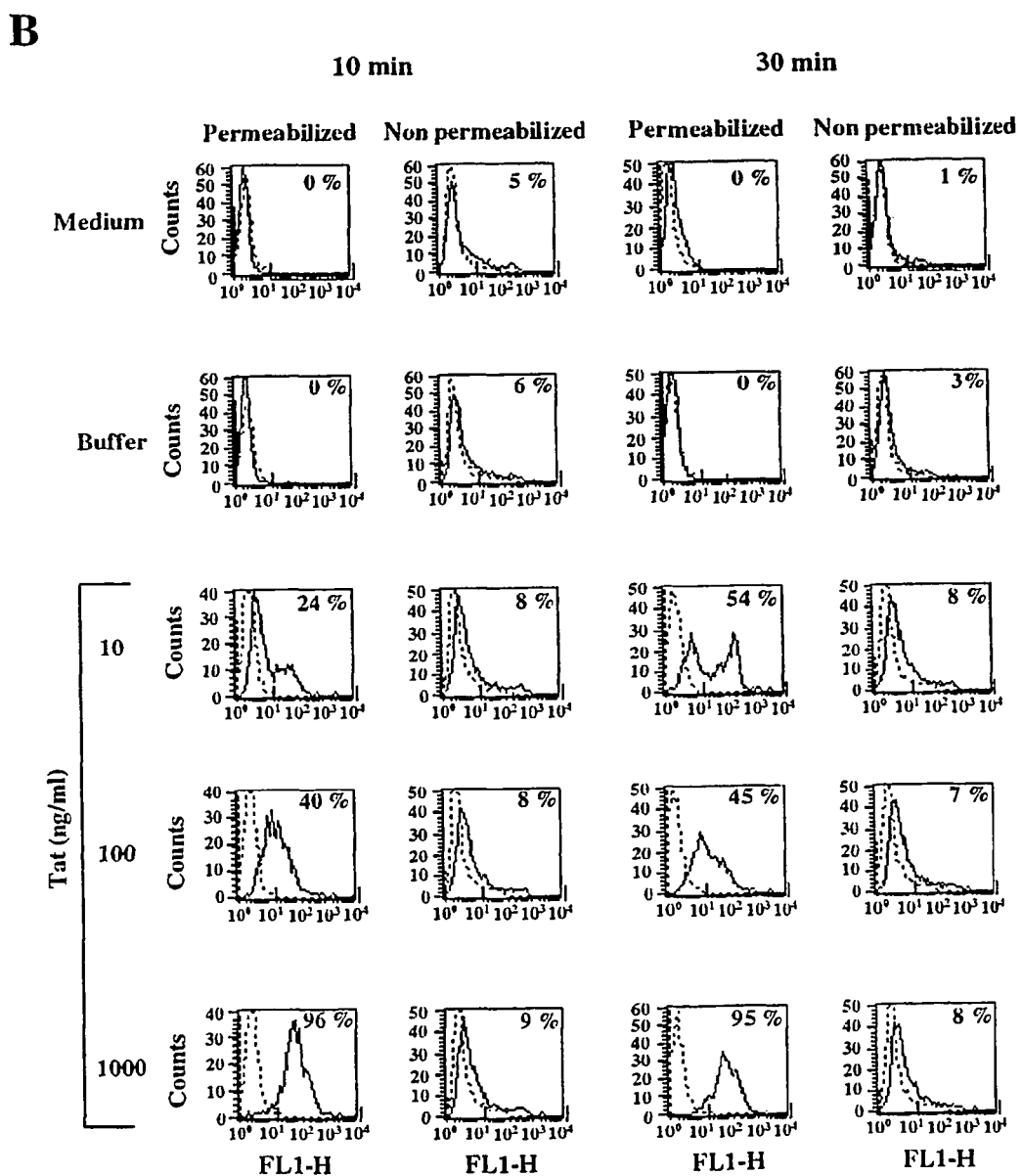

The uptake of active Tat by MDDC, TCB and BLCL was evaluated by intracellular immunofluorescence in flow cytometry, using a specific affinity-purified polyclonal antibody on permeabilized cells. FIG. 1 shows the results of a representative donor whose levels of Tat uptake represented the median of the values obtained from 14 donors tested. Tat uptake by MDDC was very efficient and occurred in a dose- and time-dependent fashion (FIG. 1A). Uptake was already evident with the lowest dose of Tat utilized (0.1 ng/ml). Regardless of the Tat concentration tested, the level of staining always peaked after 5 min of incubation and was reduced after 60 min, likely due to the processing of the protein. However, uptake of Tat remained high (98%) up to 60 min of incubation at the highest dose of Tat (10 µg/ml) utilized. No staining was observed with cells incubated in medium alone or reconstitution buffer (FIG. 1A). In addition, the Tat detected was almost entirely intracellular since no staining was observed after 10 min or 30 min of incubation of Tat with non-permeabilized cells (FIG. 1B). Similar dose- and time-kinetic of Tat uptake by MDDC was reproducibly observed with different protein lots.

In contrast to MDDC, uptake of active Tat by TCB and BLCL was much less efficient. In fact, little or no specific intracellular staining was observed with both cell types at concentrations of Tat up to 10 µg/ml after 30 or 60 min of incubation with values, at the highest dose of Tat, much lower than those obtained with MDDC (0-15% and 3-10% for BLCL and TCB, respectively, versus 98%) (FIGS. 1C and 1D). Thus, efficient uptake of active Tat is a selective feature of MDDC.

EXAMPLE 2

Figure 2A:
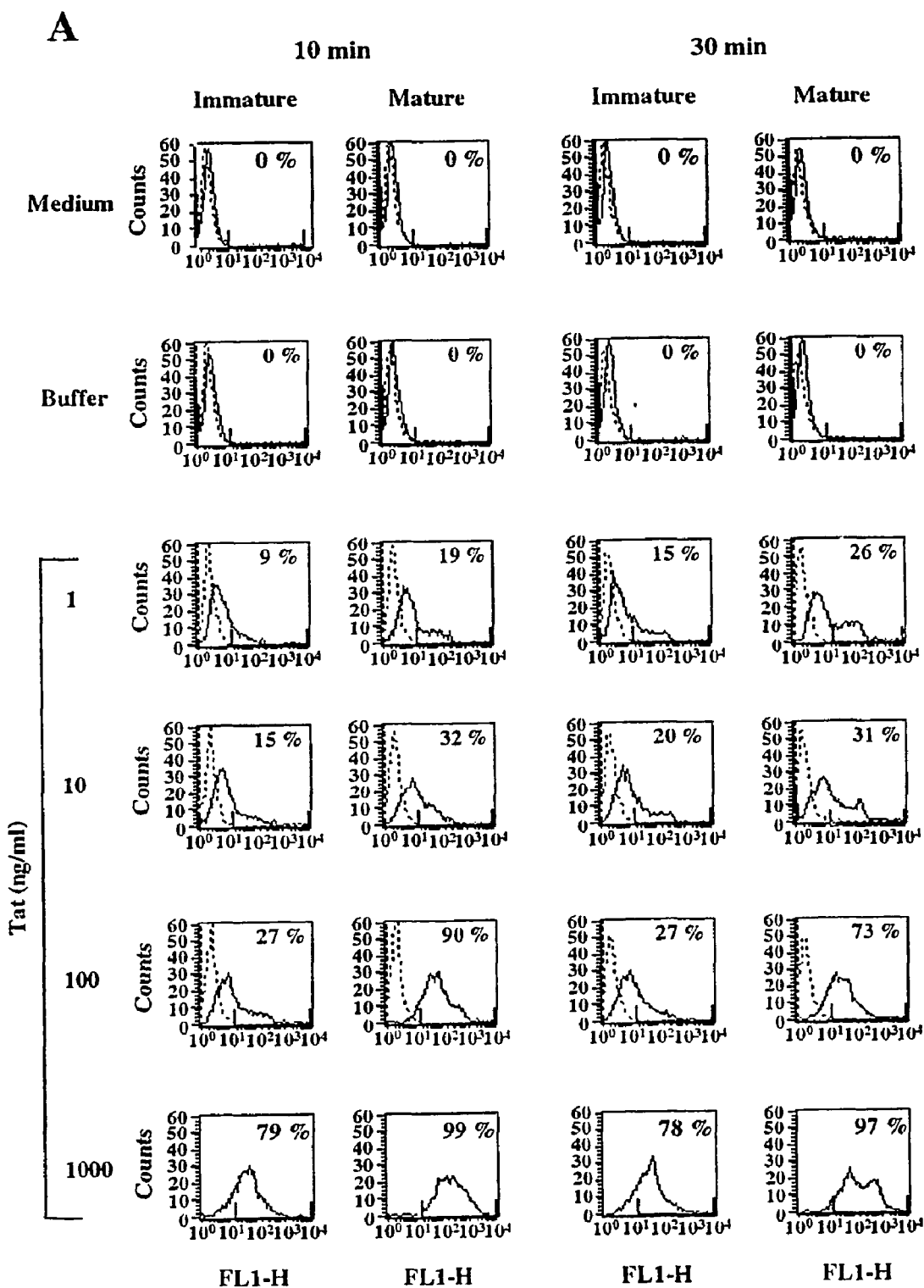
FIG. 2. Uptake of native, substantially monomeric, and biologically active Tat by MDDC increases with cell maturation and it is lost by oxidation/inactivation of the protein, as illustrated in FIG. 2A and FIG. 2B.

Uptake of Active Tat by MDDC Increases With Cell Maturation and is Lost By Oxidation and Inactivation of the Protein Immature MDDC take up antigens by phagocytosis and pinocytosis (Bankereau 1998; Bell 1999). Mature DC lose these activities while acquiring strong antigen presentation capability. To verify whether cell maturation affects the uptake of native Tat, MDDC were induced to maturate with LPS. As compared to immature MDDC, mature MDDC expressed higher levels of HLA-DR, CD83 and CD86 surface markers. Both immature or mature cells were then used for the uptake experiments. Tat uptake was highly increased by MDDC maturation at all protein concentrations tested (FIG. 2A). In fact, incubation of mature MDDC with low Tat concentrations gave levels of intracellular staining similar to those observed in immature cells with the highest doses of Tat (FIGS. 1A and 2A).

Figure 2B:
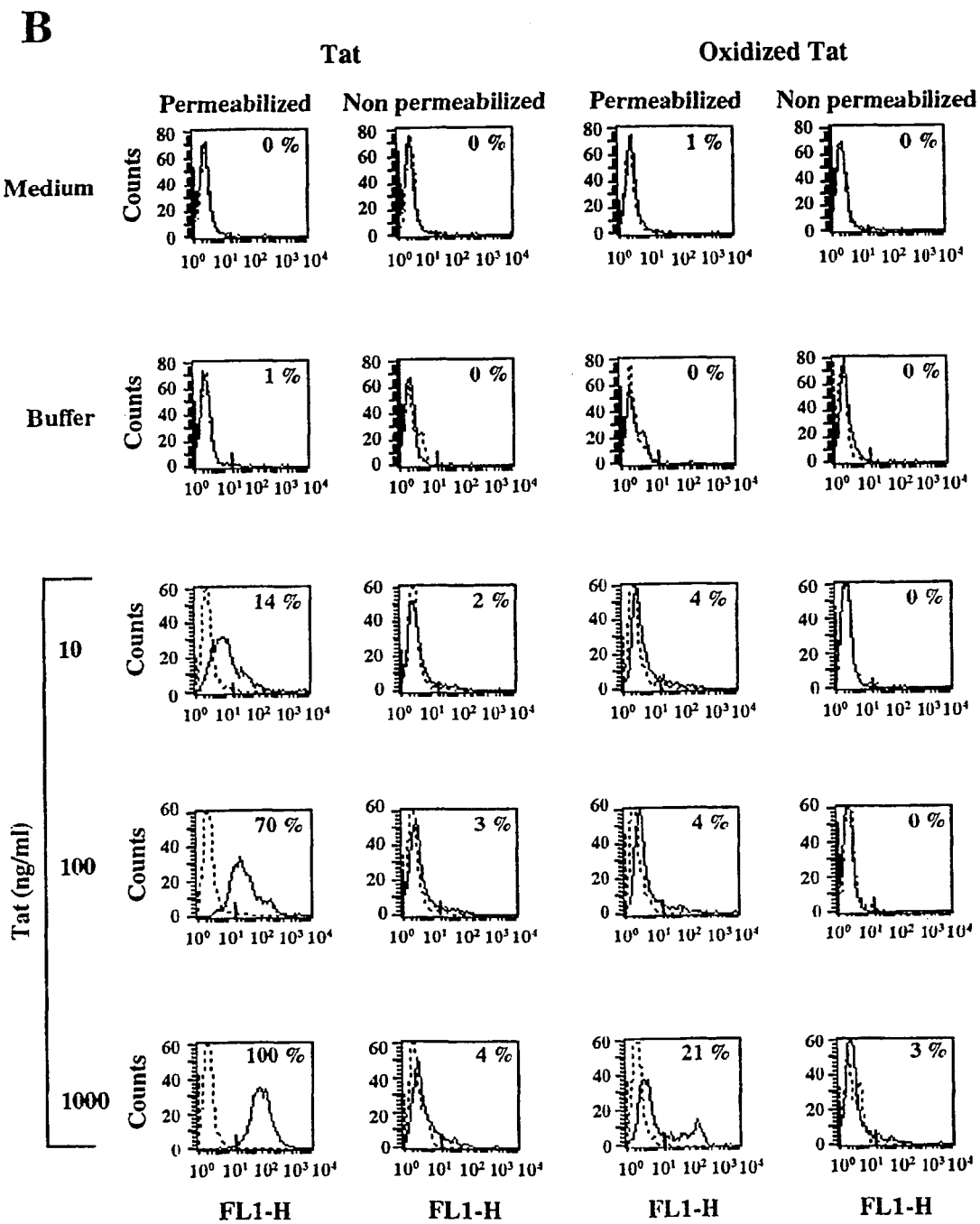

Tat contains 7 cysteins, and is extremely sensitive to oxidation which causes conformational changes and loss of biological activity. To verify the role of conformation and biological activity of Tat in the uptake process by MDCC, the protein was exposed to air and light, the loss of biological activity tested (Table I), and active or inactive Tat protein were then compared in the uptake experiments. As shown in FIG. 2B, no staining was observed with oxidized Tat up to 1 µg/ml of the protein, and, at this concentration, only a very low Tat specific staining was detected as compared to native Tat. Thus, Tat must have native conformation and biological activity for efficient uptake by MDDC.

Since MDDC maturation, that is associated with a reduced pino/phagocytic activity, increases Tat uptake, whereas oxidation and inactivation of the protein greatly reduces it to levels comparable to those observed with BLCL and TCB, it is conceivable that uptake of native Tat by MDDC is mediated by specific receptors and entry mechanisms that are not related to the pino/phagocytic activity of the cells, but are increased upon MDDC maturation.

TABLE I

Oxidation of Tat abolishes its biological activity

| Cell line | Buffer | Tat (ng/ml) | | | | | |
|---|---|---|---|---|---|---|---|
| | | 500 | 1,000 | 2,500 | 5,000 | 10,000 | |
| HLM-1 | 14 | 434 | 491 | 971 | 1507 | 5028 | native |
| | 19 | 21 | 22 | 40 | 34 | 117 | oxidized |
| HL3T1 | 0 | 29 | 34 | 79 | 81 | 187 | native |
| | 0 | 3 | 2 | 2 | 4 | 6 | oxidized |

Tat was oxidized by exposure to air and light for 18 h. Biological activity of the native and oxidized protein was then tested (at doses from 500 to 10,000 ng/ml) by measuring the capacity of rescuing the replication of Tat-defective HIV provirus in the HLM-1 cell line (Ensoli 1993; Chang 1997) or of inducing CAT activity in the HL3T1 cell line containing the LTR-CAT construct (Felber 1988). Values of the p24 (pg/ml) from culture supernatants of HLM-1 cells and CAT activity from HL3T1 cell extracts (% acetylation/100 µg of protein) are reported.

EXAMPLE 3

Block of Active Tat Uptake by MDDC With Anti-α5β1 and Anti-αvβ3 Monoclonal Antibodies or With Their Natural Ligands FN or VN To verify whether uptake of native Tat by MDDC follows a specific receptor-mediated endocytic pathway, experiments were carried out with specific monoclonal antibodies or competitor ligands directed against the integrin receptors α5β1 and αvβ3. These receptors were chosen among the several receptors binding Tat on different cell types, since they are highly expressed by activated endothelial cells and KS cells that proliferate, migrate and adhere in the presence of Tat and this is mediated by the binding of the RGD region of Tat to the α5β1 and αvβ3 integrins. As shown in FIG. 3A, B, Tat uptake by MDDC is inhibited by both anti-α5β1 and anti-αvβ3 monoclonal antibodies and the block is complete in the presence of both antibodies (FIG. 3A, B). The natural ligands for these receptors, namely FN and VN, block Tat uptake in a similar fashion (FIG. 4A, B). Thus, α5β1 and αvβ3 integrins mediate Tat entry in MDDC. This pathway of uptake is predominant at picomolar-nanomolar concentrations of the protein, whereas at higher Tat concentrations block of Tat entry is still evident but is not complete (FIGS. 3A and B). This indicates that MDDC use at least two pathways for Tat uptake, the first one occurring at low Tat concentrations (picomolar-nanomolar) is an integrin-mediated endocytosis, whereas at higher Tat concentration a low affinity cell surface interaction is also present.

EXAMPLE 4

Active Tat is Efficiently Taken Up in a Dose- and Time-Dependent Fashion By Both MDM and MDDC But Not By Monocytes Since MDDC derive from monocytes and since monocytes and MDM are known to efficiently present antigens to lymphocytes, uptake of active Tat from these cells was analysed and compared to that of MDDC from the same donors. Monocytes were purified from peripheral blood and induced to differentiate to MDDC or MDM (as described in FIG. 1 and FIG. 5). As shown in FIG. 5, monocytes took up active Tat only at the highest doses (45% and 67% at 1,000 and 10,000 ng/ml, respectively) with evidence of binding of the protein to cell surface (19% and 33%, respectively, on non-permeabilized cells). MDM took up Tat more efficiently than monocytes, with staining detectable at relatively low doses (32% and 43% at 10 ng/ml and 100 ng/ml, respectively) up to the highest dose of Tat tested (72% at 10,000 ng/ml) when surface binding of the protein (30% on non-permeabilized cells) was observed. MDDC from the same donor took up Tat more efficiently with specific staining detected already at the lowest dose tested (0.1 ng/ml) than monocytes and MDM both at 10 min and 30 min (22% and 13%, respectively). At the highest dose (1000 ng/ml) 80% and 73% of MDDC were positive after 10 and 30 min of exposure to Tat, respectively. At all the doses of the protein MDDC and MDM took up Tat markedly more efficiently than monocytes. Since both MDDC and MDM differentiate from monocytes, these data indicate that cell differentiation provides the cells with specific Tat protein targeting and uptake mechanisms.

EXAMPLE 5

Inhibition of the Uptake of Active Tat by Peptides Encompassing the Basic Region and the RGD Domain of the HIV-1 Tat Protein To verify which domain of Tat is responsible for the uptake of the biologically active protein, blocking experiments were performed by preincubating MDDC with the Tat peptides (15 mers) spanning the N-terminal region (1-15 (SEQ ID NO:38) plus 6-20 (SEQ ID NO:40)), cysteine-rich region (21-35 (SEQ ID NO:46) plus 26-40 (SEQ ID NO:48)), the basic region (46-60 (SEQ ID NO:56) plus 51-65 (SEQ ID NO:58)), RGD region (66-80 (SEQ ID NO:64) plus 71-85 (SEQ ID NO:66))(FIG. 6, panel A and B). Peptides spanning the N-terminal and cysteine-rich region did not affect the uptake of Tat at any of the doses tested (0.1-1,000 ng/ml) (FIG. 7, panel A). Peptides spanning the basic region markedly reduced the uptake of Tat at high doses (100 and 1000 ng/ml), but did not affect the uptake of lower concentrations (0.1-10 ng/ml) of the biologically active Tat protein. Conversely, peptides spanning the RGD region abolished the uptake of Tat at doses up to 10 ng/ml, and markedly reduced it at 100 and 1000 ng/ml. Of note, the combination of the Tat peptides 46-60 (SEQ ID NO:56) and 66-80 (SEQ ID NO:64) abolished the uptake of biologically active Tat both at 10 and 1000 ng/ml dose ((FIG. 7, panel B and C). Under the same experimental conditions, a longer Tat peptide spanning both the N terminal and cysteine regions (1-38 (SEQ ID NO:103)) (FIG. 6, panel C) did not affect the uptake of biologically active Tat, while Tat peptide 21-58 (SEQ ID NO:104), spanning both cysteine and basic regions, markedly reduced the uptake of Tat at 100 and 1000 ng/ml, and the Tat peptide 57-102 (SEQ ID NO:106) spanning the RGD region abolished the uptake of Tat at doses below 100 ng/ml ((FIG. 7, panel D). The Tat peptide 47-86 (SEQ ID NO:105), spanning both the basic and RGD regions, abolished the uptake of Tat at doses under 100 ng/ml and strongly reduced it at 1000 ng/ml ((FIG. 7, panel D). Thus, the blocking of α5β1 and αvβ3 integrins by peptides encompassing the RGD motif abolishes the uptake of picomolar-nanomolar (0.1 -0.10 ng/ml) concentrations of biologically active Tat, while the uptake of higher (nano- to micromolar, 10 -1,000 ng/ml) concentrations of Tat is mediated by the basic region of Tat via interaction with heparin-bound proteoglycans. Of relevance, a combination of peptides encompassing both the basic and the RGD region determines the complete abolishment of Tat uptake at any of the doses tested by interfering with both the pathways of binding and internalization of biologically active Tat protein. Thus, while these data demonstrate that both domains are needed for optimal Tat uptake, they also indicate that the RGD region is key for efficient (i.e., at low concentrations) and selective {(i.e., cell types expressing α5β1 and αvβ3 integrins, such as MDDC and activated EC (see below)} Tat uptake, whereas the basic region participates in the uptake only at high Tat concentrations, and lacks specificity of targeting since it occurs with any cell type.

EXAMPLE 6

Uptake of Active Tat by Primary Endothelial Cells Before and After Cell Activation With Inflammatory-Cytokines To analyze the uptake of active Tat by endothelial cells, HUVEC were or not activated with inflammatory cytokines and used in uptake studies with rhodaminated Tat protein.

After rhodamination Tat was active since it was still capable of promoting KS cell proliferation at the same concentration range as unlabelled Tat. This indicates that the attachment of the fluorescent label did not compromise its biological function. Cells were exposed to a wide range of Tat concentrations. In addition, to be consistent with uptake inhibition experiments (see below), cells were preincubated at 40° C. for 2 h with medium without fetal calf serum. This preincubation does not affect the subsequent uptake of rhodaminated Tat. With rhodaminated Tat, the uptake and translocation of the protein to the nucleus or nucleoli of activated HUVEC (IC-HUVEC) became detectable within 15 minutes of incubation with 10 ng/ml rhodaminated Tat (FIG. 8). The intracellular Tat activity increased in a dose-dependent (FIG. 8) and time-dependent manner (FIGS. 9 and 10). Rhodaminated BSA or buffer (negative controls) showed little or no uptake (FIG. 8, 9, 10).

To verify these data with cold active Tat, experiments were repeated by intracellular staining and FACS analysis (FIG. 11, 12). Uptake of native Tat was much more efficient by IC-HUVEC as compared to non activated cells (FIG. 11) and doses as low as 0.01 ng/ml of Tat were taken up very rapidly by the cells in a dose- and time-dependent fashion with kinetics similar or identical to those of MDDC (FIG. 12). No staining was observed with non-permeabilized cells indicating that all or most of the Tat was taken up by the cells. Thus, MDDC, IC-HUVEC and MDM possess specific mechanisms to take up Tat very efficiently.

EXAMPLE 7

Inhibition of Uptake of Active Tat by Unlabelled Protein

To verify whether the uptake of rhodaminated Tat protein by IC-HUVEC was occurring via a specific and saturable pathway(s), IC-HUVEC were incubated with 1 µg/ml unlabelled Tat prior to incubation with rhodaminated Tat at concentrations ranging from 10 ng/ml to 1 µg/ml. This procedure almost totally inhibited the uptake of rhodaminated Tat (FIG. 13 and Table II) with fluorescence levels comparable to those of the negative control (BSA). This indicates that uptake of Tat protein by IC-HUVEC is specific and saturable, suggesting that a receptor(s) is involved in this process.

TABLE II

Inhibition of uptake of 100 ng/ml and 1 µg/ml rhodaminated active Tat by IC-HUVEC after preincubation of the cells with 1 µg/ml of unlabelled Tat

| Preincubation | Incubation with Rhodaminated Tat | Uptake of Rhodaminated Tat |
| --- | --- | --- |
| Serum free medium | 100 ng/ml | +++ |
| 1 µg/ml unlabelled Tat | 100 ng/ml | +/− |
| Serum free medium | 1 µg/ml | ++++ |
| 1 µg/ml unlabelled Tat | 1 µg/ml | +/− |

IC-HUVEC were preincubated for 2 h with serum free medium in the absence or presence of 1 µg/ml unlabelled active Tat and then incubated with 100 ng/ml or 1 µg/ml rhodaminated Tat for 60 minutes. Tat uptake was visualized by fluorescence microscopy as described in the legend to FIG. 6. Negative controls (+/− uptake) were preincubation with serum free medium, followed by incubation with rhodaminated BSA.

EXAMPLE 8

Inhibition of the Uptake of Picomolar Concentrations (10 to 100 ng/ml) of Active Tat By Monoclonal Antibodies Directed Against the α5β1 and αvβ3 Integrins or By Their Ligands FN and VN To determine whether Tat uptake by IC-HUVEC was mediated by the same integrins identified with MDDC, inhibition experiments were performed by preincubating IC-HUVEC with the physiological ligands for these receptors, FN or VN, or by preincubating the cells with monoclonal antibodies directed against the RGD binding regions of the α5β1 and αvβ3 receptors. The cells were then incubated with rhodaminated Tat at concentrations ranging from 10 ng/ml to 1 µg/ml.

The uptake and nuclear localization of 10 ng/ml of rhodaminated Tat was inhibited by prior treatment of the cells with FN or VN both employed at 100 ng/ml (Table III). Similarly, uptake of 10 to 100 ng/ml of Tat was inhibited by prior treatment of the cells with monoclonal antibodies directed against the RGD binding regions of both the FN receptor, α5β1, and the VN receptor, αvβ3 (FIG. 14,15). The intensity of cellular fluorescence was reduced to the levels seen with negative controls (FIG. 12, 13). These results indicate that uptake of picomolar concentrations of Tat is mediated by the same integrins recognized with MDDC. In contrast, no inhibition was observed by prior incubation of IC-HUVEC with monoclonal antibodies directed against the factor VIII, used as negative control (FIG. 14,15), thus indicating that inhibition of Tat uptake by anti-integrin antibodies was specific.

TABLE III

Inhibition of uptake of 10 ng/ml rhodaminated active Tat by IC-HUVEC by preincubation of the cells with an excess of FN or VN

| Preincubation | Uptake of Rhodaminated Tat |
| --- | --- |
| Serum free medium | ++++ |
| 100 ng/ml FN | +/− |
| 100 ng/ml VN | +/− |

IC-HUVEC were preincubated for 2 h with serum free medium in the absence or in the presence of human FN or VN (Roche, Monza, Italy), and then incubated with 10 ng/ml rhodaminated Tat for 60 minutes. Tat uptake was visualized by fluorescence microscopy as described in the legend to FIG. 8. Negative controls (+/− uptake) were preincubation with serum free medium, followed by incubation with rhodaminated BSA.

EXAMPLE 9

Figure 17A:
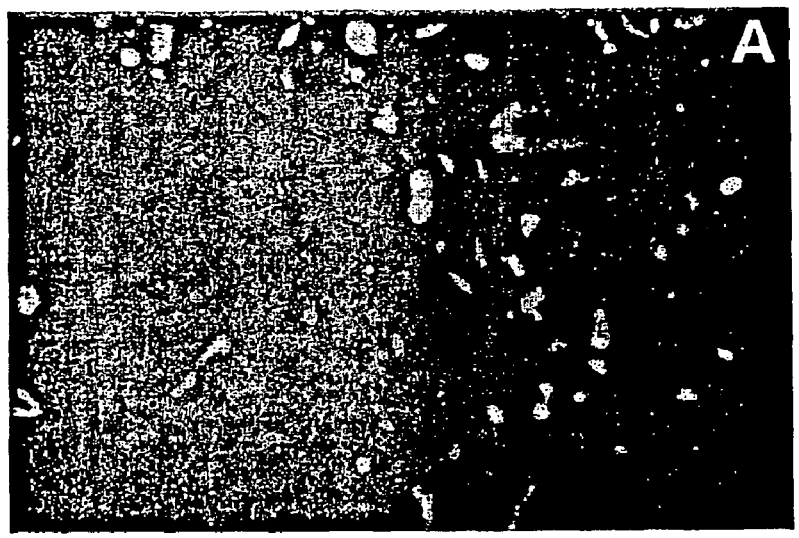
FIG. 17. Uptake of 1 µg/ml rhodaminated Tat is not inhibited by anti-integrin antibodies when cells are incubated with Tat for 60 minutes, as illustrated in FIG. 17A, FIG. 17B and FIG. 17C.
Figure 17B:
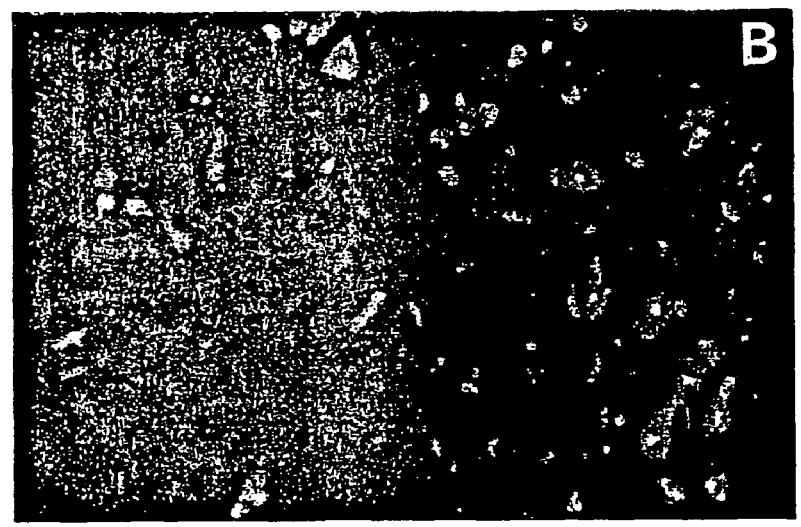
Figure 17C:
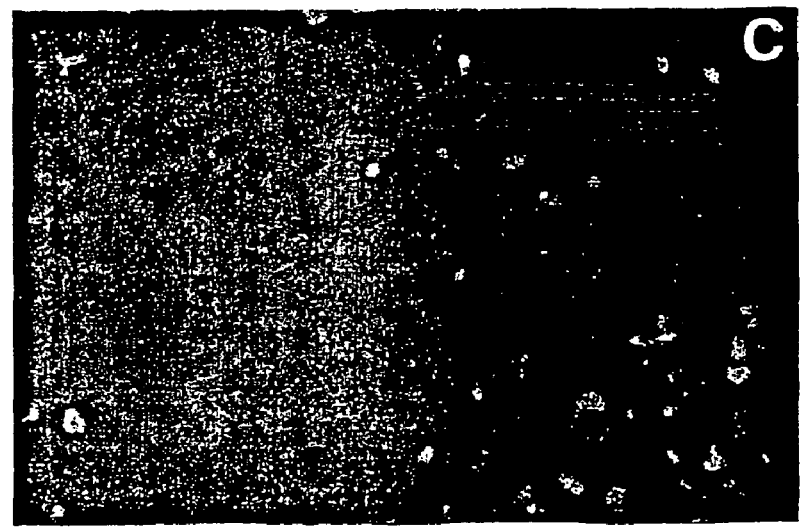

Uptake of 1 µg/ml of Active Tat is Only Partially Mediated By Integrin Receptors To determine the involvement of integrins in the uptake of higher (nanomolar-micromolar) concentrations of active Tat, IC-HUVEC were incubated with 1 g/ml rhodaminated Tat. A very intense fluorescence signal was seen in the cells within 15 minutes (FIG. 8 panel D, FIG. 10 panel A and FIG. 16 panel B). At this time of incubation, prior treatment of the cells with monoclonal antibodies against α5β1 (FIG. 16 panel C) or αvβ3 (FIG. 16 panel D) showed some inhibition of Tat uptake, but lower than that observed with 10 or 100 ng/ml of Tat. When IC-HUVEC were incubated with 1 µg/ml of rhodaminated Tat for longer periods of time (60 minutes), prior treatment of the cells with the anti-α5β1 or anti αvβ3 monoclonal antibodies did not inhibit Tat uptake (FIG. 17). These results indicated that, at this concentration and periods of incubation of Tat, the integrin-dependent uptake is saturated and another pathway of Tat uptake is predominant.

EXAMPLE 10

Tat Domains Mediating Uptake of Active Tat

To verify which domain of Tat is responsible for the uptake of picomolar-nanomolar versus micromolar concentrations of the protein, blocking experiments were performed by pre-incubating IC-HUVEC with the Tat peptides spanning the RGD region (Tat 65-80) and the basic region (Tat 46-60) (Table-IV). The Tat peptide 11-24 was used as a negative control. When rhodaminated Tat was added to the cells uptake of picomolar concentrations of Tat was inhibited by the Tat peptide 65-80 but not by Tat 46-60 or 11-24 (Table IV). In contrast, at high concentrations of extracellular Tat (1 μg/ml) uptake was not inhibited by Tat 65-80 while the Tat 46-60 had some inhibitory effects. This confirms that uptake of picomolar-nanomolar concentrations of Tat is mediated by Tat RGD region interacting with the α5β1 and αvβ3 integrins. In contrast, uptake of high (nano- to micromolar) concentrations of Tat is mediated by Tat basic region via interaction with heparin-bound proteoglycans. Thus, the RGD region is key for efficient Tat uptake, whereas the basic region participates in uptake of high Tat concentrations, however it lacks specificity of targeting since it occurs with any cell type.

TABLE IV

Tat domains mediating uptake of active Tat

| Competitor | Rhodaminated Tat (ng/ml) | Fluorescence intensity |
|---|---|---|
| Buffer | 0 | − |
| Buffer | 10 | ++ |
| (11-24) Tat | 10 | ++ |
| (46-60) Tat | 10 | ++ |
| (65-80) Tat | 10 | − |
| Buffer | 100 | +++ |
| (11-24) Tat | 100 | +++ |
| (46-60) Tat | 100 | +++ |
| (65-80) Tat | 100 | −/+ |
| Buffer | 1000 | ++++ |
| (11-24) Tat | 1000 | ++++ |
| (46-60) Tat | 1000 | ++ |
| (65-80) Tat | 1000 | +++ |

IC-HUVEC were incubated on a rotating device for 2 h at 4° C. with an excess (10 μg/ml) of (11-24)Tat, (46-60)Tat or (65-80)Tat in serum free medium. Peptide resuspension buffer (PBS-0.1% BSA) was employed as a negative control. After preincubation with competitor peptides, rhodaminated Tat was added to the cells at 10, 100 and 1000 ng/ml and cells were kept for 15' at 37° C. in a CO₂ incubator. Cells were then fixed in ice-cold acetone-methanol (1:1). The uptake and the cellular distribution of Tat were observed and photographed using fluorescence microscopy, as described in the legend to FIG. 8.

EXAMPLE 11

Active But Not Oxidized and Inactivated Tat Induces MDDC Activation and Maturation To evaluate the effect of the active Tat protein on MDDC activation and maturation, the surface expression of MHC, HLA-ABC and HLA-DR and of the costimulatory molecules CD40, CD80, CD86 and CD83 was analyzed by flow cytometry on cells cultured for 18 h in the presence of the protein, complete medium, reconstitution buffer, or LPS (positive control). Experimental data obtained with 10 different donors indicated that Tat induces a dose-dependent enhancement of the expression of MHC and co-stimulatory molecules in the absence of any cellular toxicity (Table V, panel A). A marked increase of the mean fluorescence intensity (MFI) was observed for HLA-ABC (3/6 donors, average 0.37%), for HLA-DR (10/10, average 49%), for CD40 (6/10, average 35%), for CD80 (8/8, average 50%), for CD83 (9/10, average 164%) and for CD86 (10/10, average 140%). Reconstitution buffer or medium alone did not change the expression levels of the molecules analyzed. Of note, oxidation and inactivation of Tat (Table I) markedly reduced the capacity of the protein to upregulate MHC and costimulatory molecules on MDDC (Table V, panel B). Thus, only active Tat promotes the activation and maturation of MDDC.

TABLE V

Active (A) but not oxidized and inactivated (B) Tat enhances the expression of HLA and costimulatory molecules on MDDC

A.

| | Donor Code | Medium (MFI) | Buffer (MFI) | % increase vs control Tat μg/ml | | | |
|---|---|---|---|---|---|---|---|
| | | | | 1 | 5 | 20 | LPS |
| HLA-ABC | B 19 | 392 | 332 | 55.4 | 55.7 | 78.3 | 74.0 |
| | B 24 | 291 | 309 | 6.1 | 49.2 | 49.2 | 140.9 |
| | B 26 | 304 | 297 | −4.0 | −4.7 | 15.8 | 32.6 |
| | B 38 | 130 | 127 | 31.5 | 54.3 | 63.8 | 168.5 |
| | B 53 | 276 | 272 | −8.5 | −6.3 | 2.2 | 48.9 |
| | B 55 | 251 | 259 | 2.7 | 11.2 | 13.9 | 9.2 |
| HLA-DR | B 19 | 145 | 192 | 1.0 | −1.0 | 27.1 | 84.8 |
| | B 24 | 164 | 143 | 11.9 | 60.8 | 10.5 | 48.8 |
| | B 26 | 175 | 177 | 15.8 | 23.2 | 60.5 | 60.6 |
| | B 38 | 464 | 366 | 62.3 | 98.1 | 94.5 | 85.6 |
| | B 40 | 1040 | 1127 | 27.9 | 38.9 | 34.6 | 58.9 |
| | B 43 | 415 | 408 | 18.6 | 27.7 | ND | ND |
| | B 44 | 687 | 692 | 5.1 | 11.3 | 31.4 | ND |
| | B 45 | 847 | 797 | 14.3 | 23.7 | 40.4 | ND |
| | B 53 | 471 | 493 | 11.0 | 30.8 | 94.7 | 94.5 |
| | B 55 | 313 | 303 | 38.6 | 47.2 | 46.9 | 30.7 |
| CD40 | B 19 | 53 | 51 | 23.5 | 21.6 | 19.6 | 77.4 |
| | B 24 | 60 | 58 | 19.0 | 36.2 | 41.4 | 103.3 |
| | B 26 | 42 | 43 | 4.7 | 11.6 | 16.3 | 45.2 |
| | B 38 | 70 | 62 | 45.2 | 62.9 | 95.2 | 64.3 |
| | B 40 | 85 | 76 | 38.2 | 59.2 | 60.5 | 76.5 |
| | B 43 | 48 | 48 | −2.1 | −4.2 | −6.3 | ND |
| | B 44 | 69 | 68 | 2.9 | 16.2 | 14.7 | ND |
| | B 45 | 87 | 76 | 1.3 | 15.8 | 18.4 | ND |
| | B 53 | 82 | 80 | 20.0 | 38.8 | 52.5 | 75.6 |
| | B 55 | 34 | 36 | 5.6 | 22.2 | 38.9 | 14.7 |
| CD80 | B 19 | 8 | 8 | 62.5 | 50.0 | 37.5 | 350.0 |
| | B 24 | 16 | 16 | 12.5 | 37.5 | 43.8 | 143.8 |
| | B 26 | 10 | 9 | 44.4 | 22.2 | 44.4 | 90.0 |
| | B 38 | 21 | 19 | 68.4 | 84.2 | 100.0 | 109.5 |
| | B 40 | 27 | 23 | 43.5 | 73.9 | 69.6 | 63.0 |
| | B 43 | 9 | 8 | 12.5 | 25.0 | 25.0 | ND |
| | B 44 | 18 | 18 | 0.0 | 11.1 | 27.8 | ND |
| | B 45 | 21 | 21 | 0.0 | 23.8 | 52.4 | ND |
| CD83 | B 19 | 7 | 6 | 66.7 | 100.0 | 166.7 | 442.9 |
| | B 24 | 9 | 7 | 57.1 | 257.1 | 128.6 | 200.0 |
| | B 26 | 8 | 9 | 0.0 | −11.1 | 55.6 | 62.5 |
| | B 38 | 5 | 6 | 33.3 | 150.0 | 233.3 | 520.0 |
| | B 40 | 12 | 10 | 100.0 | 190.0 | 310.0 | 233.3 |
| | B 43 | 8 | 9 | 0.0 | 11.1 | 22.2 | ND |
| | B 44 | 9 | 13 | −23.1 | −38.5 | 7.7 | ND |
| | B 45 | 7 | 10 | −30.0 | 0.0 | 90.0 | ND |
| | B 53 | 3 | 6 | 0.0 | 33.3 | 150.0 | 433.3 |
| | B 55 | 6 | 5 | 40.0 | 180.0 | 480.0 | ND |
| CD86 | B 19 | 81 | 76 | 82.9 | 76.3 | 69.7 | 133.3 |
| | B 24 | 35 | 41 | 17.1 | 48.8 | 7.3 | 77.1 |
| | B 26 | 128 | 129 | 4.7 | 25.6 | 48.1 | 55.5 |
| | B 38 | 95 | 103 | 129.2 | 220.8 | 266.7 | 288.0 |
| | B 40 | 25 | 24 | 68.0 | 95.1 | 88.3 | 144.0 |
| | B 43 | 75 | 74 | 16.2 | 35.1 | 41.9 | ND |
| | B 44 | 70 | 75 | −4.0 | 26.7 | 80.0 | ND |
| | B 45 | 51 | 50 | 44.0 | 70.0 | 166.0 | ND |
| | B 53 | 15 | 14 | 35.7 | 85.7 | 535.7 | 693.3 |
| | B 55 | 37 | 40 | 72.5 | 80.0 | 97.5 | 32.4 |

B.

| | Medium (MFI) | Buffer (MFI) | Tat (% increase vs control) | |
|---|---|---|---|---|
| HLA-DR | 313 | 303 | 46.9 | Native |
| | | | 10.6 | Oxidized |
| CD40 | 34 | 36 | 38.9 | Native |
| | | | 8.3 | Oxidized |

TABLE V-continued

Active (A) but not oxidized and inactivated (B) Tat enhances the
expression of HLA and costimulatory molecules on MDDC

| CD83 | 6  | 5  | 480.0 | Native   |
|------|----|----|-------|----------|
|      |    |    | 40.0  | Oxidized |
| CD86 | 37 | 40 | 97.5  | Native   |
|      |    |    | 15.0  | Oxidized |

% increase of HLA-DR or CD antigens expression induced by Tat or LPS as compared to buffer or medium, respectively.
Cells were exposed for 18 h to native or oxidized and inactivated Tat, reconstitution buffer, complete medium, or LPS (10 μg/ml), stained with the following fluorochrome-conjugated monoclonal antibodies: FITC- or PE-conjugated IgG isotypes, FITC-conjugated anti-CD14 and -HLA-DR (Becton-Dickinson), FITC-conjugated anti-CD40, -CD80, -CD83, PE-conjugated anti-CD86 (Pharmingen, San Diego, CA) and then analyzed by flow cytometry. In panel A the expression of the surface molecules on MDDC from 10 different donors is reported as the percentage increase of the mean fluorescence intensity (MFI) as compared to the MFI of cells incubated with Tat buffer (for Tat) or medium (for LPS). Data with oxidized versus native Tat (20 μg/ml) from a representative donor are shown in panel B. MDDC cultured with LPS were used as the positive control for the induction of HLA and costimulatory molecules.
MDDC cultured in presence of native or oxidized Tat were always viable, not differing from those treated with medium or reconstitution buffer (data not shown).

EXAMPLE 12

Native But Not Oxidized and Inactivated Tat Activates MDDC and Enhances the Production of Th-1 Type Cytokines and β-chemokines by MDDC To evaluate the effects of active Tat on DC activation, the production of the cytokines IL-12 and TNF-α, known to activate immune cells and to induce Th-1 type responses (Romagnani 1997), and of the β-chemokines RANTES, MIP-1α and MIP-1β, that are known mediators of immune responses (Moser 2001), was assessed by ELISA in the supernatants of cells cultured for 18 h with the protein, reconstitution buffer (negative control) or LPS (positive control) (FIG. 18). Incubation with active Tat induced a dose-dependent increase of the levels of IL-12 and TNFα, reaching, at the highest dose of Tat, an increase of 23-fold ($p<0.02$) for IL-12 and 20-fold ($p<0.03$) for TNF-α as compared to cells treated with buffer alone. Similarly, Tat markedly enhanced, in a dose-dependent fashion, the production of RANTES (10-fold, $p<0.02$), MIP-1α (97-fold, $p<0.005$) 0.005) and MIP-1β (15-fold, $p<0.01$). The reconstitution buffer had no effects, whereas LPS (positive control) markedly enhanced the production of both cytokines and β-chemokines.

In contrast to the effects of native Tat protein, oxidized and inactivated Tat did not increase the production of IL-12 or TNF-α. Thus, only native and active Tat increases the production and secretion of Th-1 cytokines and β chemokines by MDDC.

EXAMPLE 13

Active Tat Increases Allogeneic Presentation by MDDC

To evaluate the effect of Tat on the antigen presenting capacity of MDDC, cells were exposed to the Tat protein, reconstitution buffer, complete medium or LPS (positive control), and cultured with allogeneic PBL at serial cell to cell ratios (FIG. 19). This assay was chosen because, although not specific for a given antigen, it provides adequate information on the overall antigen presenting function of MDDC. Untreated MDDC induced some levels of proliferation of allogeneic lymphocytes, depending on the number of APC used. However, the proliferative response of allogeneic PBL was significantly enhanced by MDDC pulsed with Tat (3.3-fold, $p<0.01$, at the highest DC/PBL ratio), reaching levels similar to those induced by LPS (3.8-fold, $p<0.005$ at the same cell to cell ratio). In contrast, no enhancement of allogeneic lymphocyte proliferation was observed by treatment of MDDC with reconstitution buffer (FIG. 19). Thus, native Tat increases DC presentation function.

EXAMPLE 14

Active Tat Enhances the Presentation of Heterologous Antigens by MDDC and Specific T Cell Responses The effect of active Tat on the antigen-specific presenting capacity of MDDC was evaluated by transiently treating the cells with the protein, reconstitution buffer or complete medium, and culturing them together with autologous lymphocytes in the presence of the recall antigen TT. As shown in FIG. 20, untreated MDDC induced TT-specific proliferation of autologous lymphocytes in 2 out of the 3 donors analyzed (S.I. 15.4 and 7.3, respectively) and this effect was enhanced by their treatment with active Tat (S.I. 27.9 and 12.5, respectively), but not with reconstitution buffer (S.I. 13 and 5.9, respectively). Tat-treated MDDC did not induce lymphocyte proliferation to TT in the subject who did not respond to it. Thus, Tat can boost specific T cell responses to other antigens.

EXAMPLE 15

Immunization of Mice With Biologically Active Tat Combined With SIV Gag+MALP-2 Mucosal Adjuvant Induces Stronger Anti-Gag Humoral and Cellular Immune Responses as Compared to Vaccination with Gag+MALP-2

Because of its potent adjuvant activity, as indicated by the effects on MDDC activities, biologically active Tat is expected to increase both mucosal and systemic immune response to a nominal antigen when co-administered mucosally. To this aim, Balb/c mice (arm 2 in FIG. 21) received 2 intradermal priming with 10 μg of SIV Gag protein mixed together with biologically active Tat (10 μg) followed by 2 intranasal boosting with Tat+Gag+Malp-2. In these animals the levels, determined by Elisa, of the anti-Gag antibodies induced were higher (arm 2 in FIG. 22) than those detected in the animals immunized with Gag alone (arm 1 in FIGS. 21 and 22). More importantly, Th-1 type T cell immune responses were induced, including CTL responses as determined in a classical 5 h $^{51}$chromium release assay measuring the killing of p815 murine mastocytoma cells pulsed with a pools of Gag peptides (Targets) for 34 h prior to the addition to effector cells (splenocytes cultured for 6 days with pools of Gag peptides in the presence of exogenous IL-2). Both humoral and cellular immune responses were stronger than those induced in the control group immunized as above but without Tat (FIG. 23). Thus, immunization with a nominal antigen together with biologically active Tat generated a better immune response as compared to that of mice immunized with the nominal antigen alone. In particular, substantially higher titers of serum IgG and CTL responses to the nominal antigen were found. Similarly, enhancement of mucosal immune response (i.e., secretory IgA from lung and vaginal lavage) by biologically active Tat is foreseen.

Prophetic Example 16

Systemic immunization of monkeys with biologically active Tat expressed by a vector DNA alone or combined with DNA expressing other HIV antigens increases Th-1 responses against other antigens and confers a better control of infection upon virus challenge.

Systemic immunization of monkeys with the Tat-DNA expressing vector alone or associated with DNA expressing other antigens is expected to induce a T cell immune response and IFNγ Elispot (Th-1 type) against itself and to increase Th-1 responses against other antigens as compared to vaccination with other antigens in the absence of Tat. Furthermore, the association of Tat with other HIV antigens such as Env, Gag and Pol is expected to provide better protection than vaccination with Tat alone upon challenge with the pathogenic SHIV89.6P.

In particular, intramuscular immunization (3 inoculations in 6 weeks time period) of juvenile rhesus monkeys (Macaca mulatta) with DNA of HIV-1 tat (0.5 mg) alone or associated with HIV-1 env and $SIV_{mac239}$ gag DNA (0.5 mg each) followed by 2 intramuscular boosts with either biologically active Tat protein (25 µg) and ISCOMs alone or associated with 25 µg of HIV-1 Env and 25 µg of $SIV_{mac239}$ Gag proteins, is expected to generate a specific Th-1 immune response, including induction of specific antibodies, lymphoproliferative responses and CTL assessed by Elispot for IFNγ, IL-2 and IL-4 to biologically active Tat protein and/or peptides thereof alone, or to biologically active Tat protein and/or peptides thereof and to HIV-1 Env and $SIV_{mac239}$ Gag proteins and/or peptides thereof.

Further, given the immunodominance of Env and Gag/Pol antigens as compared to Tat and the inherent adjuvanticity of Tat itself, it is predicted that immunization with the latter will need to be performed at least twice prior to initiation of vaccination with the former antigens to obtain a comparable immune response to all immunogens. Thus, it is foreseen that vaccination (9 inoculations in 36 weeks time period) of juvenile rhesus monkeys (Macaca mulatta) with DNA of HIV-1 tat (0.5 mg) alone or associated (starting from the 3rd inoculation) with 0.5 mg each of HIV-1 env and $SIV_{mac239}$ gag/pol DNA (7 inoculations in 30 weeks time period) followed by 2 intramuscular boosts with either biologically active Tat protein (25 µg) and ISCOMs alone or associated with 25 µg each of HIV-1 Env and of $SIV_{mac239}$ Gag/Pol proteins and ISCOMs will generate a stronger and broader (as compared to the former and shorter immunization schedule) specific immune response to all the vaccine antigens, especially in terms of CTL responses, as assessed by Elispot for IFNγ, IL-2 and IL4 to biologically active Tat protein and/or peptides thereof alone, or to biologically active Tat protein and/or peptides thereof and to HIV-1 Env and $SIV_{mac239}$ Gag proteins and/or peptides thereof.

Finally it is foreseen that vaccination against Tat, Env and Gag/Pol will confer better control of infection, as compared to animals vaccinated with Tat or Gag/Pol alone, upon intravenous challenge with SHIV 89.6P.

REFERENCES

Addo, M. M., et al. *Proc. Natl. Acad. Sci. USA* 98:1781, 2001.
Albini, A., et al. *Proc. Natl. Acad. Sci. USA* 92:4838, 1995.
Albini, A., et al. *Nat. Med.* 2:1371, 1996.
Albini, A., et al. *Proc. Natl. Acad. Sci. USA*. 95:13153, 1998a.
Albini, A., et al. *J. Biol. Chem.* 273:15895, 1998b.
Allen, T. M., et al. *Nature* 407:386, 2000.
Arya, S. K., et al. *Science* 229:69, 1985.
Badou, A., et al. *J. Virol.* 74:10551, 2000.
Banchereau, J., and R. M. Steinman. *Nature* 392:245, 1998.
Barillari, G., et al. *J. Immunol.* 149:3727, 1992.
Barillari, G., et al. *Proc. Natl. Acad. Sci. USA* 90:7941, 1993.
Barillari, G., et al. *J. Immunol.* 163:1929, 1999a.
Barillari, G., et al. *Blood* 94:663, 1999b.
Bell, D., et al. *Adv. Immunol.* 72:255, 1999.
Benelli, R., et al. *AIDS* 12:261, 1998.
Benjouad, A., et al. *FEBS Lett.* 319:119, 1993.
Boykins, R. A., et al. *J. Immunol.* 163:15, 1999.
Cafaro, A., et al. *Nat. Med.* 5:643, 1999.
Cafaro, A., et al. *J. Med. Primatol.* 29:193, 2000.
Cafaro, A., et al. *Vaccine* 19:2862, 2001.
Chang, H. C., et al. *AIDS* 11:1421, 1997.
Chang, H-K., et al. *J. Biomed. Sci.* 2:189, 1995.
Chirmule, N., et al. *J. Virol.* 69:492, 1995.
Cohen, S. S., et al. *Proc. Natl. Acad. Sci. USA* 96:10842, 1999.
Derossi, D., et al. *Trends Cell. Biol.* 8:84, 1998.
Ensoli, B., et al. *Nature* 345:84, 1990.
Ensoli, B., et al. *J. Virol.* 67:277, 1993.
Ensoli, B., et al. *Nature* 371:674, 1994.
Fanales-Belasio, E., et al. *J. Immunol.* 159:2203, 1997.
Fawell, S., et al. *Proc. Natl. Acad. Sci. USA* 91:664, 1994.
Felber, B. K., and G. N. Paviakis. *Science* 239:184, 1988.
Fiorelli, V., et al. *J. Immunol.* 162:1165, 1999.
Fisher, A. G., et al. *Nature* 320:367, 1986.
Frankel, A. D., and C. O. Pabo. *Cell* 55:1189, 1988.
Frankel, A. D., et al. *Proc. Natl. Acad. Sci. USA* 86:7397, 1989.
Friedman-Kien, A. E. *J. Am. Acad. Dermatol.* 5:468, 1981.
Froebel, K. S., et al. *AIDS Res. Hum. Retroviruses* 10 suppl. 2:S83, 1994.
Gallo, R. C. *Proc. Natl. Acad. Sci. USA* 96:8324, 1999.
Ganju, R. K., et al. *J. Virol.* 72:6131, 1998.
Goldstein, G., et al. *Vaccine* 18:2789, 2000.
Gutheil, W. G., et al. *Proc. Natl. Aced. Sci. USA* 91:6594, 1994.
Huang, L., et al. *J. Virol.* 72:8952, 1998.
Ito, M., et al. *AIDS Res. Hum. Retroviruses* 14:845, 1998.
Kim, D. T., et al. *J. Immunol.* 159:1666, 1997.
Kolson, D. L., et al. *AIDS Res. Hum. Retroviruses* 9:677, 1993.
Lafrenie, R. M., et al. *J. Immunol.* 157:974, 1996.
Li, C. J., et al. *Science* 268:429, 1995.
Li, C. J., et al. *Proc. Natl. Acad. Sci. USA* 94:8116, 1997.
Mann, D. A., and A. D. Frankel. EMBO J. 10:1733, 1991.
Masood, R., et al. *Biochem. Biophys. Res. Commun.* 202:374, 1994.
McCloskey, T. W., et al. *J. Immunol* 158:1014, 1997.
Micheletti, F., et al. *Eur. J. Immunol.* 29:2579, 1999.
Milani, D., et al. *J. Biol. Chem.* 271:22961, 1996.
Mitola, S., et al. *J. Virol.* 74:344, 2000.
Mitola, S., et al. *Blood* 90:1365, 1997.
Morini, M., et al. *Biochem. Biophys. Res. Commun.* 273:267, 2000.
Moser, B., and P. Loetscher. *Nat. Immunol.* 2:123, 2001.
Moy, P., et al. *Mol. Biotechnol.* 6:105, 1996.
Osterhaus, A D., et al. *Vaccine* 17:2713, 1999.
Ott, M., et al. *Science* 275:1481, 1997.
Pauza, C. D., et al. *Proc. Natl. Aced. Sci. USA* 97:3515, 2000.
Pittis, M. G., et al. *Viral. Immunol.* 9:169, 1996.
Pober, J. S. In «Endothelial cell», Una S. Ryan (ed.) C. R. C. Press Inc., Boca Raton, Florida, 1998.
Poggi, A., et al. *J. Biol. Chem.* 273:7205, 1998.
Purvis, S. F., et al. *AIDS Res. Hum. Retroviruses* 11:443, 1995.
Raines, E. W., and R. Ross. *J. Cell. Biol.* 116:533, 1992.
Re, M. C., et al. *J. Acquir. Immune Defic. Syndr. Hum. Retrovirol.* 10:408, 1995.
Reiss, P., et al. *J. Med. Virol.* 30:163, 1990.

Rodman, T. C., et al. *Proc. Natl. Acad. Sci. USA* 90:7719, 1993.
Romagnani, S. *Immunol. Today* 18:263, 1997.
Rubartelli, A., et al. *Eur. J. Immunol* 27:1893, 1997.
Rusnati, M., et al. *J. Biol. Chem.* 273:16027, 1998.
Sabatier, J. M., et al. *J. Virol.* 65:961, 1991.
Safai, B., et al. *Ann. Intern. Med.* 103:744, 1985.
Samaniego, F., et al. *Am. J. Pathol.* 152:433, 1998.
Secchiero, P., et al. *J. Immunol.* 162:2427, 1999.
Speiser, P. P. *Methods Find Exp. Clin. Pharmacol* 13:337, 1991
Subramanyam, M., et al. *J. Immunol.* 150:2544, 1993.
Takeuchi, H., et al. *Adv. Drug Deliv. Rev.* 47:39, 2001
Tyagi, M., et al. *J. Biol. Chem.* 276:3254, 2001.
van Baalen, C. A., et al. *J. Gen. Virol.* 78:1913, 1997.
Venet, A., et al. *J. Immunol.* 148:2899, 1992.
Viscidi, R. P., et al. *Science* 246:1606, 1989.
Vogel, B. E., et al. *J. Cell. Biol.* 121:461, 1993.
Weeks, B. S., et al. *J. Biol. Chem.* 268:5279, 1993.
Wender, P. A., et al. *Proc. Natl. Acad. Sci. USA* 97:13003, 2000.
Westendorp, M. O., et al. *Nature* 375:497, 1995.
Wrenger, S., et al. *FEBS Lett.* 383:145, 1996.
Wrenger, S., et al. *J. Biol. Chem.* 272:30283, 1997.
Wu, M. X. and S. F. Schlossman. *Proc. Natl. Acad. Sci. USA* 94:13832, 1997.
Zagury, D., et al. *Proc. Natl. Acad. Sci. USA* 95:3851, 1998.
Zagury, J. F., et al. *J. Hum. Virol.* 1:282, 1998.
Zauli, G., et al. *Cancer Res.* 53:4481, 1993.
Zauli, G., et al. *J. Acquir. Immune Defic. Syndr. Hum. Retrovirol.* 10:306, 1995a.
Zauli, G., et al. *Blood* 86:3823, 1995b.
Zocchi, M. R., et al. *AIDS* 11:1227, 1997.

The invention claimed is:

1. A composition comprising an isolated, native, substantially monomeric, biologically active HIV Tat protein, or an isolated fragment or isolated derivative thereof, wherein the HIV Tat protein, fragment, or derivative,
   (i) contains the RGD domain of an HIV-1 Tat protein;
   (ii) has adjuvant activity; and
   (iii) is bound to
       an antigen of a pathogen that is not HIV, where said pathogen is a virus, Mycobacterium tuberculosis, Listeria, Streptococcus, Staphylococcus, pneumococcus, Clostridium tetani, Mycobacterium, meningococcus, Helicobacter, Salmonella, Vibrio cholerae, Candida, or Plasmodium.

2. The composition of claim 1, wherein the HIV Tat protein, fragment, or derivative is fused to the antigenic molecule.

3. The composition of claim 1, wherein the HIV Tat protein, fragment, or derivative is chemically crosslinked to the antigenic molecule.

4. The composition of claim 1, wherein the HIV Tat protein, fragment, or derivative is associated with a support particle containing the antigenic molecule.

5. The composition of claim 4, wherein the support particle is a microparticle, nanoparticle, liposome, or particulated delivery system.

6. The composition of claim 1, wherein the HIV Tat protein, fragment, or derivative is of HIV-1 or HIV-2.

7. The composition of claim 6 comprising said HIV Tat protein, wherein the HIV Tat protein comprises the amino acid sequence of SEQ ID NO:2.

8. The composition of claim 6 comprising said isolated HIV Tat fragment, wherein the HIV Tat fragment comprises the amino acid sequence of SEQ ID NO:4, 6, 8, 10, 12, 14, 16 or 18.

9. The composition of claim 6 comprising said isolated HIV Tat derivative, wherein the HIV Tat derivative comprises the amino acid sequence of SEQ ID NO:96; SEQ ID NO:98; or SEQ ID NO:100.

10. The composition of claim 1 comprising said isolated HIV Tat fragment or derivative.

11. The composition of claim 1, wherein the RGD domain is selected from the group consisting of amino acid residues 73-86 (SEQ ID NO:4), amino acid residues 74-84 (SEQ ID NO:6), amino acid residues 75-83 (SEQ ID NO:8), amino acid residues 76-82 (SEQ ID NO:10), amino acid residues 77-81 (SEQ ID NO:12), amino acid residues 77-82 (SEQ ID NO:14), amino acid residues 77-83 (SEQ ID NO:16), and amino acid residues 76-83 (SEQ ID NO:18), of HTLV-IIIB, clone BH-10.

12. The composition of claim 1, wherein the HIV Tat protein, fragment, or derivative selectively targets, binds or enters an antigen presenting cell expressing $\alpha 5\beta 1$ and/or $\alpha v\beta 3$ integrins.

13. The composition of claim 12, wherein the antigen presenting cell is a dendritic cell, endothelial cell, or macrophage.

14. The composition of claim 12, wherein the HIV Tat protein, fragment, or derivative further induces the maturation or an antigen presenting function of the antigen presenting cell.

15. The composition of claim 1, further comprising a therapeutic molecule selected from the group consisting of an anti-inflammatory drug, anti-angiogenic molecule, and cytotoxic anti-tumor drug.

16. The composition of claim 1, wherein the antigenic molecule is the antigen of the pathogen that is not HIV.

17. The composition of claim 16, wherein the pathogen is a virus.

18. A method for inducing an immune response, comprising administering to a subject the composition of claim 16, wherein said immune response is against said pathogen, and wherein the HIV Tat protein, fragment, or derivative is administered in an amount effective for the HIV Tat protein, fragment, or derivative to act as an adjuvant.

19. The composition of claim 1 that is a fusion protein comprising:
a first amino acid sequence of said HIV Tat protein, fragment, or derivative; and
a second amino acid sequence, said second amino acid sequence being of said antigenic molecule.

20. The composition of claim 16, wherein the virus is a herpesvirus, a hepatitis virus, an influenza virus, a varicella, an Epstein Barr virus, a human herpesvirus-8, a cytomegalovirus, or a papillomavirus.

21. The method of claim 18, wherein the HIV Tat protein, fragment, or derivative is fused to the antigenic molecule.

22. The method of claim 18, wherein the HIV Tat protein, fragment, or derivative is chemically crosslinked to the antigenic molecule.

23. The method of claim 18, wherein the HIV Tat protein, fragment, or derivative is associated with a support particle containing the antigenic molecule.

24. The method of claim 23, wherein the support particle is a microparticle, nanoparticle, liposome, or particulated delivery system.

25. The method of claim 18, wherein the HIV Tat protein, fragment, or derivative is of HIV-1 or HIV-2.

26. The method of claim 25, wherein the composition comprises said HIV Tat protein, and wherein the HIV Tat protein comprises the amino acid sequence of SEQ ID NO:2.

27. The method of claim 25, wherein the composition comprises said isolated HIV Tat fragment, and wherein the HIV Tat fragment comprises the amino acid sequence of SEQ ID NO:4, 6, 8, 10, 12, 14, 16 or 18.

28. The method of claim 25, wherein the composition comprises said isolated HIV Tat derivative, and wherein the HIV Tat derivative comprises the amino acid sequence of SEQ ID NO:96, 98 or 100.

29. The method of claim 18, wherein the composition comprises said isolated HIV Tat fragment or derivative.

30. The method of claim 18, wherein the RGD domain is selected from the group consisting of amino acid residues 73-86 (SEQ ID NO:4), amino acid residues 74-84 (SEQ ID NO:6), amino acid residues 75-83 (SEQ ID NO:8), amino acid residues 76-82 (SEQ ID NO:10), amino acid residues 77-81 (SEQ ID NO:12), amino acid residues 77-82 (SEQ ID NO:14), amino acid residues 77-83(SEQ ID NO:16), and amino acid residues 76-83 (SEQ ID NO:18), of HTLV-IIIB, clone BH-10.

31. The method of claim 18, wherein the HIV Tat protein, fragment, or derivative selectively targets, binds or enters an antigen presenting cell expressing $\alpha 5\beta 1$ and/or $\alpha v\beta 3$ integrins.

32. The method of claim 31, wherein the antigen presenting cell is a dendritic cell, endothelial cell, or macrophage.

33. The method of claim 31, wherein the HIV Tat protein, fragment, or derivative further induces the maturation or an antigen presenting function of the antigen presenting cell.

34. The method of claim 18, wherein the pathogen is a virus.

35. The method of claim 34, wherein the virus is a herpesvirus, a hepatitis virus, an influenza virus, a varicella, an Epstein Barr virus, a human herpesvirus-8, a cytomegalovirus, or a papillomavirus.

36. The method of claim 18, 26, or 34, wherein the subject is a human.

37. The method of claim 21 or 30, wherein the subject is a human.

* * * * *

SEQUENCE LISTING

```
<160> NUMBER OF SEQ ID NOS: 106

<210> SEQ ID NO 1
<211> LENGTH: 261
<212> TYPE: DNA
<213> ORGANISM: Aids-associated retrovirus

<400> SEQUENCE: 1
atggagccag tagatcctag actagagccc tggaagcatc caggaagtca gcctaaaact    60
gcttgtacca attgctattg taaaaagtgt tgctttcatt gccaagtttg tttcataaca   120
aaagccttag gcatctccta tggcaggaag aagcggagac agcgacgaag acctcctcaa   180
ggcagtcaga ctcatcaagt ttctctatca aagcagccca cctcccaatc ccgaggggac   240
ccgacaggcc cgaaggaatg a                                             261

<210> SEQ ID NO 2
<211> LENGTH: 86
<212> TYPE: PRT
<213> ORGANISM: Aids-associated retrovirus

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 3
<211> LENGTH: 42
<212> TYPE: DNA
<213> ORGANISM: Aids-associated retrovirus

<400> SEQUENCE: 3
cccacctccc aatcccgagg ggacccgaca ggcccgaagg aa                       42
```

```
<210> SEQ ID NO 4
<211> LENGTH: 14
<212> TYPE: PRT
<213> ORGANISM: Aids-associated retrovirus

<400> SEQUENCE: 4

Pro Thr Ser Gln Ser Arg Gly Asp Pro Thr Gly Pro Lys Glu
1               5                   10

<210> SEQ ID NO 5
<211> LENGTH: 33
<212> TYPE: DNA
<213> ORGANISM: Aids-associated retrovirus

<400> SEQUENCE: 5
acctcccaat cccgagggga cccgacaggc ccg                              33

<210> SEQ ID NO 6
<211> LENGTH: 11
<212> TYPE: PRT
<213> ORGANISM: Aids-associated retrovirus

<400> SEQUENCE: 6

Thr Ser Gln Ser Arg Gly Asp Pro Thr Gly Pro
1               5                   10

<210> SEQ ID NO 7
<211> LENGTH: 27
<212> TYPE: DNA
<213> ORGANISM: Aids-associated retrovirus

<400> SEQUENCE: 7
tcccaatccc gagggaccc gacaggc                                      27

<210> SEQ ID NO 8
<211> LENGTH: 9
<212> TYPE: PRT
<213> ORGANISM: Aids-associated retrovirus

<400> SEQUENCE: 8

Ser Gln Ser Arg Gly Asp Pro Thr Gly
1               5

<210> SEQ ID NO 9
<211> LENGTH: 21
<212> TYPE: DNA
<213> ORGANISM: Aids-associated retrovirus

<400> SEQUENCE: 9
caatcccgag gggacccgac a                                           21

<210> SEQ ID NO 10
<211> LENGTH: 7
<212> TYPE: PRT
<213> ORGANISM: Aids-associated retrovirus

<400> SEQUENCE: 10

Gln Ser Arg Gly Asp Pro Thr
1               5

<210> SEQ ID NO 11
<211> LENGTH: 15
<212> TYPE: DNA
<213> ORGANISM: Aids-associated retrovirus
```

```
<400> SEQUENCE: 11
tcccgagggg acccg                                                          15

<210> SEQ ID NO 12
<211> LENGTH: 5
<212> TYPE: PRT
<213> ORGANISM: Aids-associated retrovirus

<400> SEQUENCE: 12

Ser Arg Gly Asp Pro
1               5

<210> SEQ ID NO 13
<211> LENGTH: 18
<212> TYPE: DNA
<213> ORGANISM: Aids-associated retrovirus

<400> SEQUENCE: 13
tcccgagggg acccgaca                                                       18

<210> SEQ ID NO 14
<211> LENGTH: 6
<212> TYPE: PRT
<213> ORGANISM: Aids-associated retrovirus

<400> SEQUENCE: 14

Ser Arg Gly Asp Pro Thr
1               5

<210> SEQ ID NO 15
<211> LENGTH: 21
<212> TYPE: DNA
<213> ORGANISM: Aids-associated retrovirus

<400> SEQUENCE: 15
tcccgagggg acccgacagg c                                                   21

<210> SEQ ID NO 16
<211> LENGTH: 7
<212> TYPE: PRT
<213> ORGANISM: Aids-associated retrovirus

<400> SEQUENCE: 16

Ser Arg Gly Asp Pro Thr Gly
1               5

<210> SEQ ID NO 17
<211> LENGTH: 24
<212> TYPE: DNA
<213> ORGANISM: Aids-associated retrovirus

<400> SEQUENCE: 17
caatcccgag gggacccgac aggc                                                24

<210> SEQ ID NO 18
<211> LENGTH: 8
<212> TYPE: PRT
<213> ORGANISM: Aids-associated retrovirus

<400> SEQUENCE: 18

Gln Ser Arg Gly Asp Pro Thr Gly
1               5
```

<210> SEQ ID NO 19
<211> LENGTH: 48
<212> TYPE: DNA
<213> ORGANISM: Aids-associated retrovirus

<400> SEQUENCE: 19
tgtaccaatt gctattgtaa aaagtgttgc tttcattgcc aagtttgt           48

<210> SEQ ID NO 20
<211> LENGTH: 16
<212> TYPE: PRT
<213> ORGANISM: Aids-associated retrovirus

<400> SEQUENCE: 20

Cys Thr Asn Cys Tyr Cys Lys Lys Cys Cys Phe His Cys Gln Val Cys
1               5                   10                  15

<210> SEQ ID NO 21
<211> LENGTH: 42
<212> TYPE: DNA
<213> ORGANISM: Aids-associated retrovirus

<400> SEQUENCE: 21
ggcaggaaga agcggagaca gcgacgaaga cctcctcaag gc           42

<210> SEQ ID NO 22
<211> LENGTH: 14
<212> TYPE: PRT
<213> ORGANISM: Aids-associated retrovirus

<400> SEQUENCE: 22

Gly Arg Lys Lys Arg Arg Gln Arg Arg Pro Pro Gln Gly
1               5                   10

<210> SEQ ID NO 23
<211> LENGTH: 30
<212> TYPE: DNA
<213> ORGANISM: Aids-associated retrovirus

<400> SEQUENCE: 23
ttcataacaa aagccttagg catctcctat           30

<210> SEQ ID NO 24
<211> LENGTH: 10
<212> TYPE: PRT
<213> ORGANISM: Aids-associated retrovirus

<400> SEQUENCE: 24

Phe Ile Thr Lys Ala Leu Gly Ile Ser Tyr
1               5                   10

<210> SEQ ID NO 25
<211> LENGTH: 60
<212> TYPE: DNA
<213> ORGANISM: Aids-associated retrovirus

<400> SEQUENCE: 25
atggagccag tagatcctag actagagccc tggaagcatc caggaagtca gcctaaaact           60

<210> SEQ ID NO 26
<211> LENGTH: 20
<212> TYPE: PRT
<213> ORGANISM: Aids-associated retrovirus

```
<400> SEQUENCE: 26

Met Glu Pro Val Asp Pro Arg Leu Glu Pro Trp Lys His Pro Gly Ser
1               5                   10                  15

Gln Pro Lys Thr
            20

<210> SEQ ID NO 27
<211> LENGTH: 60
<212> TYPE: DNA
<213> ORGANISM: Aids-associated retrovirus

<400> SEQUENCE: 27
atggagccag tagatcctag actagagccc tggaagcatc caggaagtca gcctaaaact      60

<210> SEQ ID NO 28
<211> LENGTH: 20
<212> TYPE: PRT
<213> ORGANISM: Aids-associated retrovirus

<400> SEQUENCE: 28

Met Glu Pro Val Asp Pro Arg Leu Glu Pro Trp Lys His Pro Gly Ser
1               5                   10                  15

Gln Pro Lys Thr
            20

<210> SEQ ID NO 29
<211> LENGTH: 42
<212> TYPE: DNA
<213> ORGANISM: Aids-associated retrovirus

<400> SEQUENCE: 29
tggaagcatc caggaagtca gcctaaaact gcttgtacca at                        42

<210> SEQ ID NO 30
<211> LENGTH: 14
<212> TYPE: PRT
<213> ORGANISM: Aids-associated retrovirus

<400> SEQUENCE: 30

Trp Lys His Pro Gly Ser Gln Pro Lys Thr Ala Cys Thr Asn
1               5                   10

<210> SEQ ID NO 31
<211> LENGTH: 60
<212> TYPE: DNA
<213> ORGANISM: Aids-associated retrovirus

<400> SEQUENCE: 31
gcttgtacca attgctattg taaaaagtgt tgctttcatt gccaagtttg tttcataaca      60

<210> SEQ ID NO 32
<211> LENGTH: 20
<212> TYPE: PRT
<213> ORGANISM: Aids-associated retrovirus

<400> SEQUENCE: 32

Ala Cys Thr Asn Cys Tyr Cys Lys Lys Cys Cys Phe His Cys Gln Val
1               5                   10                  15

Cys Phe Ile Thr
            20
```

<210> SEQ ID NO 33
<211> LENGTH: 45
<212> TYPE: DNA
<213> ORGANISM: Aids-associated retrovirus

<400> SEQUENCE: 33
gtttgtttca taacaaaagc cttaggcatc tcctatggca ggaag            45

<210> SEQ ID NO 34
<211> LENGTH: 15
<212> TYPE: PRT
<213> ORGANISM: Aids-associated retrovirus

<400> SEQUENCE: 34

Val Cys Phe Ile Thr Lys Ala Leu Gly Ile Ser Tyr Gly Arg Lys
1               5                   10                  15

<210> SEQ ID NO 35
<211> LENGTH: 60
<212> TYPE: DNA
<213> ORGANISM: Aids-associated retrovirus

<400> SEQUENCE: 35
ggcccgaagg aacagaagaa gaaggtggag agagagacag agacagatcc ggtccatcag    60

<210> SEQ ID NO 36
<211> LENGTH: 20
<212> TYPE: PRT
<213> ORGANISM: Aids-associated retrovirus

<400> SEQUENCE: 36

Gly Pro Lys Glu Gln Lys Lys Lys Val Glu Arg Glu Thr Glu Thr Asp
1               5                   10                  15

Pro Val His Gln
            20

<210> SEQ ID NO 37
<211> LENGTH: 45
<212> TYPE: DNA
<213> ORGANISM: Aids-associated retrovirus

<400> SEQUENCE: 37
atggagccag tagatcctag actagagccc tggaagcatc cagga            45

<210> SEQ ID NO 38
<211> LENGTH: 15
<212> TYPE: PRT
<213> ORGANISM: Aids-associated retrovirus

<400> SEQUENCE: 38

Met Glu Pro Val Asp Pro Arg Leu Glu Pro Trp Lys His Pro Gly
1               5                   10                  15

<210> SEQ ID NO 39
<211> LENGTH: 45
<212> TYPE: DNA
<213> ORGANISM: Aids-associated retrovirus

<400> SEQUENCE: 39
cctagactag agccctggaa gcatccagga agtcagccta aaact            45

```
<210> SEQ ID NO 40
<211> LENGTH: 15
<212> TYPE: PRT
<213> ORGANISM: Aids-associated retrovirus

<400> SEQUENCE: 40

Pro Arg Leu Glu Pro Trp Lys His Pro Gly Ser Gln Pro Lys Thr
1               5                   10                  15

<210> SEQ ID NO 41
<211> LENGTH: 45
<212> TYPE: DNA
<213> ORGANISM: Aids-associated retrovirus

<400> SEQUENCE: 41
tggaagcatc caggaagtca gcctaaaact gcttgtacca attgc              45

<210> SEQ ID NO 42
<211> LENGTH: 15
<212> TYPE: PRT
<213> ORGANISM: Aids-associated retrovirus

<400> SEQUENCE: 42

Trp Lys His Pro Gly Ser Gln Pro Lys Thr Ala Cys Thr Asn Cys
1               5                   10                  15

<210> SEQ ID NO 43
<211> LENGTH: 45
<212> TYPE: DNA
<213> ORGANISM: Aids-associated retrovirus

<400> SEQUENCE: 43
agtcagccta aaactgcttg taccaattgc tattgtaaaa agtgt              45

<210> SEQ ID NO 44
<211> LENGTH: 15
<212> TYPE: PRT
<213> ORGANISM: Aids-associated retrovirus

<400> SEQUENCE: 44

Ser Gln Pro Lys Thr Ala Cys Thr Asn Cys Tyr Cys Lys Lys Cys
1               5                   10                  15

<210> SEQ ID NO 45
<211> LENGTH: 45
<212> TYPE: DNA
<213> ORGANISM: Aids-associated retrovirus

<400> SEQUENCE: 45
gcttgtacca attgctattg taaaaagtgt tgctttcatt gccaa              45

<210> SEQ ID NO 46
<211> LENGTH: 15
<212> TYPE: PRT
<213> ORGANISM: Aids-associated retrovirus

<400> SEQUENCE: 46

Ala Cys Thr Asn Cys Tyr Cys Lys Lys Cys Cys Phe His Cys Gln
1               5                   10                  15

<210> SEQ ID NO 47
<211> LENGTH: 45
<212> TYPE: DNA
<213> ORGANISM: Aids-associated retrovirus
```

```
<400> SEQUENCE: 47
tattgtaaaa agtgttgctt tcattgccaa gtttgtttca taaca          45

<210> SEQ ID NO 48
<211> LENGTH: 15
<212> TYPE: PRT
<213> ORGANISM: Aids-associated retrovirus

<400> SEQUENCE: 48

Tyr Cys Lys Lys Cys Cys Phe His Cys Gln Val Cys Phe Ile Thr
1               5                   10                  15

<210> SEQ ID NO 49
<211> LENGTH: 45
<212> TYPE: DNA
<213> ORGANISM: Aids-associated retrovirus

<400> SEQUENCE: 49
tgctttcatt gccaagtttg tttcataaca aaagccttag gcatc           45

<210> SEQ ID NO 50
<211> LENGTH: 15
<212> TYPE: PRT
<213> ORGANISM: Aids-associated retrovirus

<400> SEQUENCE: 50

Cys Phe His Cys Gln Val Cys Phe Ile Thr Lys Ala Leu Gly Ile
1               5                   10                  15

<210> SEQ ID NO 51
<211> LENGTH: 45
<212> TYPE: DNA
<213> ORGANISM: Aids-associated retrovirus

<400> SEQUENCE: 51
gtttgtttca taacaaaagc cttaggcatc tcctatggca ggaag           45

<210> SEQ ID NO 52
<211> LENGTH: 15
<212> TYPE: PRT
<213> ORGANISM: Aids-associated retrovirus

<400> SEQUENCE: 52

Val Cys Phe Ile Thr Lys Ala Leu Gly Ile Ser Tyr Gly Arg Lys
1               5                   10                  15

<210> SEQ ID NO 53
<211> LENGTH: 45
<212> TYPE: DNA
<213> ORGANISM: Aids-associated retrovirus

<400> SEQUENCE: 53
aaagccttag gcatctccta tggcaggaag aagcggagac agcga           45

<210> SEQ ID NO 54
<211> LENGTH: 15
<212> TYPE: PRT
<213> ORGANISM: Aids-associated retrovirus

<400> SEQUENCE: 54

Lys Ala Leu Gly Ile Ser Tyr Gly Arg Lys Lys Arg Arg Gln Arg
1               5                   10                  15
```

<210> SEQ ID NO 55
<211> LENGTH: 45
<212> TYPE: DNA
<213> ORGANISM: Aids-associated retrovirus

<400> SEQUENCE: 55
tcctatggca ggaagaagcg gagacagcga cgaagacctc ctcaa					45

<210> SEQ ID NO 56
<211> LENGTH: 15
<212> TYPE: PRT
<213> ORGANISM: Aids-associated retrovirus

<400> SEQUENCE: 56

Ser Tyr Gly Arg Lys Lys Arg Arg Gln Arg Arg Pro Pro Gln
1               5                   10                  15

<210> SEQ ID NO 57
<211> LENGTH: 45
<212> TYPE: DNA
<213> ORGANISM: Aids-associated retrovirus

<400> SEQUENCE: 57
aagcggagac agcgacgaag acctcctcaa ggcagtcaga ctcat					45

<210> SEQ ID NO 58
<211> LENGTH: 15
<212> TYPE: PRT
<213> ORGANISM: Aids-associated retrovirus

<400> SEQUENCE: 58

Lys Arg Arg Gln Arg Arg Pro Pro Gln Gly Ser Gln Thr His
1               5                   10                  15

<210> SEQ ID NO 59
<211> LENGTH: 45
<212> TYPE: DNA
<213> ORGANISM: Aids-associated retrovirus

<400> SEQUENCE: 59
cgaagacctc ctcaaggcag tcagactcat caagtttctc tatca					45

<210> SEQ ID NO 60
<211> LENGTH: 15
<212> TYPE: PRT
<213> ORGANISM: Aids-associated retrovirus

<400> SEQUENCE: 60

Arg Arg Pro Pro Gln Gly Ser Gln Thr His Gln Val Ser Leu Ser
1               5                   10                  15

<210> SEQ ID NO 61
<211> LENGTH: 45
<212> TYPE: DNA
<213> ORGANISM: Aids-associated retrovirus

<400> SEQUENCE: 61
ggcagtcaga ctcatcaagt ttctctatca aagcagccca cctcc					45

<210> SEQ ID NO 62
<211> LENGTH: 15
<212> TYPE: PRT
<213> ORGANISM: Aids-associated retrovirus -continued

```
<400> SEQUENCE: 62

Gly Ser Gln Thr His Gln Val Ser Leu Ser Lys Gln Pro Thr Ser
1               5                   10                  15

<210> SEQ ID NO 63
<211> LENGTH: 45
<212> TYPE: DNA
<213> ORGANISM: Aids-associated retrovirus

<400> SEQUENCE: 63
caagtttctc tatcaaagca gcccacctcc caatcccgag gggac          45

<210> SEQ ID NO 64
<211> LENGTH: 15
<212> TYPE: PRT
<213> ORGANISM: Aids-associated retrovirus

<400> SEQUENCE: 64

Gln Val Ser Leu Ser Lys Gln Pro Thr Ser Gln Ser Arg Gly Asp
1               5                   10                  15

<210> SEQ ID NO 65
<211> LENGTH: 45
<212> TYPE: DNA
<213> ORGANISM: Aids-associated retrovirus

<400> SEQUENCE: 65
aagcagccca cctcccaatc ccgagcggac ccgacaggcc cgaag          45

<210> SEQ ID NO 66
<211> LENGTH: 15
<212> TYPE: PRT
<213> ORGANISM: Aids-associated retrovirus

<400> SEQUENCE: 66

Lys Gln Pro Thr Ser Gln Ser Arg Gly Asp Pro Thr Gly Pro Lys
1               5                   10                  15

<210> SEQ ID NO 67
<211> LENGTH: 45
<212> TYPE: DNA
<213> ORGANISM: Aids-associated retrovirus

<400> SEQUENCE: 67
cagcctcgag gggacccgac aggcccgaag gaacagaaga agaag          45

<210> SEQ ID NO 68
<211> LENGTH: 15
<212> TYPE: PRT
<213> ORGANISM: Aids-associated retrovirus

<400> SEQUENCE: 68

Gln Pro Arg Gly Asp Pro Thr Gly Pro Lys Glu Gln Lys Lys Lys
1               5                   10                  15

<210> SEQ ID NO 69
<211> LENGTH: 27
<212> TYPE: DNA
<213> ORGANISM: Aids-associated retrovirus

<400> SEQUENCE: 69
gcttgtacca attgctattg taaaaag                              27
```

```
<210> SEQ ID NO 70
<211> LENGTH: 9
<212> TYPE: PRT
<213> ORGANISM: Aids-associated retrovirus

<400> SEQUENCE: 70

Ala Cys Thr Asn Cys Tyr Cys Lys Lys
1               5

<210> SEQ ID NO 71
<211> LENGTH: 27
<212> TYPE: DNA
<213> ORGANISM: Aids-associated retrovirus

<400> SEQUENCE: 71
tattgtaaaa agtgttgctt tcattgc                                      27

<210> SEQ ID NO 72
<211> LENGTH: 9
<212> TYPE: PRT
<213> ORGANISM: Aids-associated retrovirus

<400> SEQUENCE: 72

Tyr Cys Lys Lys Cys Cys Phe His Cys
1               5

<210> SEQ ID NO 73
<211> LENGTH: 27
<212> TYPE: DNA
<213> ORGANISM: Aids-associated retrovirus

<400> SEQUENCE: 73
tgctttcatt gccaagtttg tttcata                                      27

<210> SEQ ID NO 74
<211> LENGTH: 9
<212> TYPE: PRT
<213> ORGANISM: Aids-associated retrovirus

<400> SEQUENCE: 74

Cys Phe His Cys Gln Val Cys Phe Ile
1               5

<210> SEQ ID NO 75
<211> LENGTH: 27
<212> TYPE: DNA
<213> ORGANISM: Aids-associated retrovirus

<400> SEQUENCE: 75
gtttgtttca taacaaaagc cttaggc                                      27

<210> SEQ ID NO 76
<211> LENGTH: 9
<212> TYPE: PRT
<213> ORGANISM: Aids-associated retrovirus

<400> SEQUENCE: 76

Val Cys Phe Ile Thr Lys Ala Leu Gly
1               5

<210> SEQ ID NO 77
<211> LENGTH: 27
<212> TYPE: DNA
<213> ORGANISM: Aids-associated retrovirus
```

<400> SEQUENCE: 77
aaagccttag gcatctccta tggcagg                                              27

<210> SEQ ID NO 78
<211> LENGTH: 9
<212> TYPE: PRT
<213> ORGANISM: Aids-associated retrovirus

<400> SEQUENCE: 78

Lys Ala Leu Gly Ile Ser Tyr Gly Arg
1               5

<210> SEQ ID NO 79
<211> LENGTH: 27
<212> TYPE: DNA
<213> ORGANISM: Aids-associated retrovirus

<400> SEQUENCE: 79
tcctatggca ggaagaagcg gagacag                                              27

<210> SEQ ID NO 80
<211> LENGTH: 9
<212> TYPE: PRT
<213> ORGANISM: Aids-associated retrovirus

<400> SEQUENCE: 80

Ser Tyr Gly Arg Lys Lys Arg Arg Gln
1               5

<210> SEQ ID NO 81
<211> LENGTH: 27
<212> TYPE: DNA
<213> ORGANISM: Aids-associated retrovirus

<400> SEQUENCE: 81
aagcggagac agcgacgaag acctcct                                              27

<210> SEQ ID NO 82
<211> LENGTH: 9
<212> TYPE: PRT
<213> ORGANISM: Aids-associated retrovirus

<400> SEQUENCE: 82

Lys Arg Arg Gln Arg Arg Arg Pro Pro
1               5

<210> SEQ ID NO 83
<211> LENGTH: 27
<212> TYPE: DNA
<213> ORGANISM: Aids-associated retrovirus

<400> SEQUENCE: 83
cgaagacctc ctcaaggcag tcagact                                              27

<210> SEQ ID NO 84
<211> LENGTH: 9
<212> TYPE: PRT
<213> ORGANISM: Aids-associated retrovirus

<400> SEQUENCE: 84

Arg Arg Pro Pro Gln Gly Ser Gln Thr
1               5

```
<210> SEQ ID NO 85
<211> LENGTH: 27
<212> TYPE: DNA
<213> ORGANISM: Aids-associated retrovirus

<400> SEQUENCE: 85
ggcagtcaga ctcatcaagt ttctcta                                          27

<210> SEQ ID NO 86
<211> LENGTH: 9
<212> TYPE: PRT
<213> ORGANISM: Aids-associated retrovirus

<400> SEQUENCE: 86

Gly Ser Gln Thr His Gln Val Ser Leu
1               5

<210> SEQ ID NO 87
<211> LENGTH: 27
<212> TYPE: DNA
<213> ORGANISM: Aids-associated retrovirus

<400> SEQUENCE: 87
caagtttctc tatcaaagca gcccacc                                          27

<210> SEQ ID NO 88
<211> LENGTH: 9
<212> TYPE: PRT
<213> ORGANISM: Aids-associated retrovirus

<400> SEQUENCE: 88

Gln Val Ser Leu Ser Lys Gln Pro Thr
1               5

<210> SEQ ID NO 89
<211> LENGTH: 27
<212> TYPE: DNA
<213> ORGANISM: Aids-associated retrovirus

<400> SEQUENCE: 89
aagcagccca cctcccaatc ccgaggg                                          27

<210> SEQ ID NO 90
<211> LENGTH: 9
<212> TYPE: PRT
<213> ORGANISM: Aids-associated retrovirus

<400> SEQUENCE: 90

Lys Gln Pro Thr Ser Gln Ser Arg Gly
1               5

<210> SEQ ID NO 91
<211> LENGTH: 27
<212> TYPE: DNA
<213> ORGANISM: Aids-associated retrovirus

<400> SEQUENCE: 91
caatcccgag gggacccgac aggcccg                                          27

<210> SEQ ID NO 92
<211> LENGTH: 9
<212> TYPE: PRT
<213> ORGANISM: Aids-associated retrovirus
```

```
<400> SEQUENCE: 92

Gln Ser Arg Gly Asp Pro Thr Gly Pro
1               5

<210> SEQ ID NO 93
<211> LENGTH: 27
<212> TYPE: DNA
<213> ORGANISM: Aids-associated retrovirus

<400> SEQUENCE: 93
ccgacaggcc cgaaggaaca gaagaag                                           27

<210> SEQ ID NO 94
<211> LENGTH: 9
<212> TYPE: PRT
<213> ORGANISM: Aids-associated retrovirus

<400> SEQUENCE: 94

Pro Thr Gly Pro Lys Glu Gln Lys Lys
1               5

<210> SEQ ID NO 95
<211> LENGTH: 261
<212> TYPE: DNA
<213> ORGANISM: Aids-associated retrovirus

<400> SEQUENCE: 95
atggagccag tagatcctag actagagccc tggaagcatc caggaagtca gcctaaaact      60
gctggtacca attgctattg taaaaagtgt tgctttcatt gccaagtttg tttcataaca     120
aaagccttag gcatctccta tggcaggaag aagcggagac agcgacgaag acctcctcaa     180
ggcagtcaga ctcatcaagt ttctctatca aagcagccca cctcccaatc ccgaggggac     240
ccgacaggcc cgaaggaatg a                                               261

<210> SEQ ID NO 96
<211> LENGTH: 86
<212> TYPE: PRT
<213> ORGANISM: Aids-associated retrovirus

<400> SEQUENCE: 96

Met Glu Pro Val Asp Pro Arg Leu Glu Pro Trp Lys His Pro Gly Ser
1               5                   10                  15

Gln Pro Lys Thr Ala Gly Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 97
<211> LENGTH: 261
<212> TYPE: DNA
<213> ORGANISM: Aids-associated retrovirus
```

```
<400> SEQUENCE: 97
atggagccag tagatcctag actagagccc tggaagcatc caggaagtca gcctaaaact    60
gcttgtacca attgctattg taaaaagtgt tgctttcatt gccaagtttg tttcataaca   120
aacgccttag gcatctccta tggcaggaag aagcggagac agcgacgaag acctcctcaa   180
ggcagtcaga ctcatcaagt ttctctatca aagcagccca cctcccaatc ccgaggggac   240
ccgacaggcc cgaaggaatg a                                             261

<210> SEQ ID NO 98
<211> LENGTH: 86
<212> TYPE: PRT
<213> ORGANISM: Aids-associated retrovirus

<400> SEQUENCE: 98
```

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Thr Ala Leu Gly Ile Ser Tyr Gly
        35                  40                  45

Arg Lys Lys Arg Arg Gln Arg Arg Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

```
<210> SEQ ID NO 99
<211> LENGTH: 402
<212> TYPE: DNA
<213> ORGANISM: Aids-associated retrovirus

<400> SEQUENCE: 99
atggagacac ccttgaaggc gccagagagc tcattaaagt cctgcaacga gccctttttca    60 cgcacttcag agcaggatgt ggccactcaa gaattggcca gacaagggga ggaaatcctc   120
tctcagctat accgaccccct agaaacatgc aataactcat gctattgtaa gcgatgctgc   180
taccattgtc agatgtgttt tctaaacaag gggctcggga tatgttatga acgaaagggc   240
agacgaagaa ggactccaaa gaaaactaag actcatcgag gggacccgtc tcctacacca   300
gacaaatcca tatccacaag gaccggggac agccagccaa cgaagaaaca gaagaagacg   360
gtggaagcaa cggtggagac agatactggc cctggccgat ag                      402

<210> SEQ ID NO 100
<211> LENGTH: 133
<212> TYPE: PRT
<213> ORGANISM: Aids-associated retrovirus

<400> SEQUENCE: 100
```

Met Glu Thr Pro Leu Lys Ala Pro Glu Ser Ser Leu Lys Ser Cys Asn
1               5                   10                  15

Glu Pro Phe Ser Arg Thr Ser Glu Gln Asp Val Ala Thr Gln Glu Leu
            20                  25                  30

Ala Arg Gln Gly Glu Glu Ile Leu Ser Gln Leu Tyr Arg Pro Leu Glu
        35                  40                  45

Thr Cys Asn Asn Ser Cys Tyr Cys Lys Arg Cys Cys Tyr His Cys Gln
    50                  55                  60

```
Met Cys Phe Leu Asn Lys Gly Leu Gly Ile Cys Tyr Glu Arg Lys Gly
 65                  70                  75                  80

Arg Arg Arg Arg Thr Pro Lys Lys Thr Lys Thr His Arg Gly Asp Pro
                 85                  90                  95

Ser Pro Thr Pro Asp Lys Ser Ile Ser Thr Arg Thr Gly Asp Ser Gln
            100                 105                 110

Pro Thr Lys Lys Gln Lys Lys Thr Val Glu Ala Thr Val Glu Thr Asp
        115                 120                 125

Thr Gly Pro Gly Arg
        130
```

<210> SEQ ID NO 101
<211> LENGTH: 390
<212> TYPE: DNA
<213> ORGANISM: Aids-associated retrovirus

<400> SEQUENCE: 101

```
atggagacac ccttgaaggc gccagagagc tcattaaagt cctgcaacga gcccttttca    60
cgcacttcag agcaggatgt ggccactcaa gaattggcca gacaagggga ggaaatcctc   120
tctcagctat accgacccct agaaacatgc aataactcat gctattgtaa gcgatgctgc   180
taccattgtc agatgtgttt tctaaacaag gggctcggga tatgttatga acgaaagggc   240
agacgaagaa ggactccaaa gaaaactaag actcatccgt ctcctacacc agacaaatcc   300
atatccacaa ggggggacag ccagccaacg aagaaacaga agaagacggt ggaagcaacg   360
gtggagacag atactggccc tggccgatag                                    390
```

<210> SEQ ID NO 102
<211> LENGTH: 129
<212> TYPE: PRT
<213> ORGANISM: Aids-associated retrovirus

<400> SEQUENCE: 102

```
Met Glu Thr Pro Leu Lys Ala Pro Glu Ser Ser Leu Lys Ser Cys Asn
 1               5                  10                  15

Glu Pro Phe Ser Arg Thr Ser Glu Gln Asp Val Ala Thr Gln Glu Leu
             20                  25                  30

Ala Arg Gln Gly Glu Glu Ile Leu Ser Gln Leu Tyr Arg Pro Leu Glu
        35                  40                  45

Thr Cys Asn Asn Ser Cys Tyr Cys Lys Arg Cys Cys Tyr His Cys Gln
    50                  55                  60

Met Cys Phe Leu Asn Lys Gly Leu Gly Ile Cys Tyr Glu Arg Lys Gly
 65                  70                  75                  80

Arg Arg Arg Arg Thr Pro Lys Lys Thr Lys Thr His Pro Ser Pro Thr
                 85                  90                  95

Pro Asp Lys Ser Ile Ser Thr Arg Gly Asp Ser Gln Pro Thr Lys Lys
            100                 105                 110

Gln Lys Lys Thr Val Glu Ala Thr Val Glu Thr Asp Thr Gly Pro Gly
        115                 120                 125

Arg
```

<210> SEQ ID NO 103
<211> LENGTH: 38
<212> TYPE: PRT
<213> ORGANISM: AIDS-associated retrovirus

```
-continued

<400> SEQUENCE: 103

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe
        35

<210> SEQ ID NO 104
<211> LENGTH: 38
<212> TYPE: PRT
<213> ORGANISM: AIDS-associated retrovirus

<400> SEQUENCE: 104

Ala Cys Thr Asn Cys Tyr Cys Lys Lys Cys Cys Phe His Cys Gln Val
1               5                   10                  15

Cys Phe Ile Thr Lys Ala Leu Gly Ile Ser Tyr Gly Arg Lys Lys Arg
            20                  25                  30

Arg Gln Arg Arg Arg Pro
        35

<210> SEQ ID NO 105
<211> LENGTH: 40
<212> TYPE: PRT
<213> ORGANISM: AIDS-associated retrovirus

<400> SEQUENCE: 105

Tyr Gly Arg Lys Lys Arg Arg Gln Arg Arg Arg Pro Pro Gln Gly Ser
1               5                   10                  15

Gln Thr His Gln Val Ser Leu Ser Lys Gln Pro Thr Ser Gln Ser Arg
            20                  25                  30

Gly Asp Pro Thr Gly Pro Lys Glu
        35                  40

<210> SEQ ID NO 106
<211> LENGTH: 46
<212> TYPE: PRT
<213> ORGANISM: AIDS-associated retrovirus

<400> SEQUENCE: 106

Arg Pro Pro Gln Gly Ser Gln Thr His Gln Val Ser Leu Ser Lys Gln
1               5                   10                  15

Pro Thr Ser Gln Ser Arg Gly Asp Pro Thr Gly Pro Lys Glu Gln Lys
            20                  25                  30

Lys Lys Val Glu Arg Glu Thr Glu Thr Asp Pro Val His Gln
        35                  40                  45
```